US009528133B2

(12) United States Patent
Kambourakis et al.

(10) Patent No.: US 9,528,133 B2

(45) Date of Patent: Dec. 27, 2016

(54) COMPOSITIONS AND METHODS FOR PRODUCING CHEMICALS AND DERIVATIVES THEREOF

(71) Applicant: SYNTHETIC GENOMICS, INC., La Jolla, CA (US)

(72) Inventors: Spiros Kambourakis, San Diego, CA (US); Benjamin M. Griffin, San Diego, CA (US); Kevin V. Martin, Solana Beach, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/222,453

(22) Filed: Mar. 21, 2014

(65) Prior Publication Data

US 2014/0206047 A1 Jul. 24, 2014

Related U.S. Application Data

(63) Continuation-in-part of application No. 14/033,300, filed on Sep. 20, 2013.

(60) Provisional application No. 61/704,408, filed on Sep. 21, 2012.

(51) Int. Cl.

| | |
|---|---|
| ***C12P 7/58*** | (2006.01) |
| ***C12P 7/42*** | (2006.01) |
| ***C12P 17/04*** | (2006.01) |
| ***C07D 309/30*** | (2006.01) |
| ***C07D 307/33*** | (2006.01) |
| ***C12N 15/52*** | (2006.01) |

(52) U.S. Cl.

CPC ............... *C12P 7/58* (2013.01); *C07D 307/33* (2013.01); *C07D 309/30* (2013.01); *C12N 15/52* (2013.01)

(58) Field of Classification Search

None

See application file for complete search history.

(56) References Cited

U.S. PATENT DOCUMENTS

| | | | |
|---|---|---|---|
| 3,184,479 | A | 5/1965 | Matter |
| 3,203,963 | A | 8/1965 | Hales et al. |
| 3,326,944 | A | 6/1967 | Lew |
| 5,298,411 | A | 3/1994 | Sogabe et al. |
| 7,385,081 | B1 | 6/2008 | Gong |
| 7,411,078 | B2 | 8/2008 | Miura et al. |
| 8,242,292 | B2 | 8/2012 | Yutaka et al. |
| 8,530,186 | B2 | 9/2013 | Ito et al. |
| 2010/0075381 | A1 | 3/2010 | Ito et al. |
| 2011/0124065 | A1 | 5/2011 | Moon et al. |
| 2011/0183382 | A1 | 7/2011 | Schmalisch et al. |
| 2012/0264179 | A1 | 10/2012 | Burgard et al. |
| 2014/0171683 | A1 | 6/2014 | Sieber et al. |
| 2014/0295508 | A1 | 10/2014 | Yoshikuni et al. |
| 2015/0152452 | A1 | 6/2015 | Kalum et al. |

FOREIGN PATENT DOCUMENTS

| | | | |
|---|---|---|---|
| EP | 2 683 815 | B1 | 5/2015 |
| GB | 957 985 | | 5/1964 |
| WO | WO 2010/072902 | A1 | 7/2010 |
| WO | WO 2011/043661 | A1 | 4/2011 |
| WO | WO 2013/049711 | A1 | 4/2013 |
| WO | WO 2013/151428 | A1 | 10/2013 |
| WO | WO 2013/183610 | A1 | 12/2013 |

OTHER PUBLICATIONS

Chica et al. Curr Opin Biotechnol. Aug. 2005;16(4):378-84.*

Sen et al. Appl Biochem Biotechnol. Dec. 2007;143(3):212-23.*

International Search Report issued on Sep. 8, 2015, regarding PCT/US2015/021848.

Heuts et al.: *"Discovery, characterization, and kinetic analysis of an alditol oxidase from Streptomyces coelicolor"*; J. Biol. Chem, Jul. 13, 2007, vol. 28, pp. 20283-20291.

PubChem. Glucuronic Acid (CID 23677976) Feb. 5, 2008 [retrieved Dec. 1, 2013]. Available on the internet: <URL:http://pubchem.ncbi.nlm.nih.gov/summary/summary.cgi?cid=23677976&loc=ec_rcs>.

International Search Report regarding PCT/US2013/061036.

Aden. A. et al.: *"Top Value Added Chemicals From Biomass Volume I—Results of Screening for Potential Candidates from Sugars and Synthesis Gas"*; DOE National Renewable Enrgy Lab, Aug. 2004, DOE/GO 102004-1993; 76 pages.

De Jong, E. et al.: *"Furandicarboxylic Acid(FDCA), A Versatile Building Block for a Very Interesting Class of Polyesters"*; American Chemical Society, Aug. 6, 2012, pp. 1-13.

(Continued)

*Primary Examiner* — Christian Fronda

(74) *Attorney, Agent, or Firm* — DLA Piper LLP (US)

(57) ABSTRACT

The present invention provides methods for producing a product of one or more enzymatic pathways. The pathways used in the methods of the invention involve one or more conversion steps such as, for example, an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid Step 7b); and an enzymatic conversion of 5-ketocluconate into 4,6-dihydroxy 2,5-diketo hexanoate (2,5-DDH) (Step 16). In some embodiments the methods of the invention produce 2,5-furandicarboxylic acid (FDCA) as a product. The methods include both enzymatic and chemical conversions as steps. Various pathways are also provided for converting glucose into 5-dehdyro-4-deoxy-glucarate (DDG), and for converting glucose into 2,5-furandicarboxylic acid (FDCA). The methods also involve the use of engineered enzymes that perform reactions with high specificity and efficiency. Additional products that can be produce include metabolic products such as, but not limited to, guluronic acid, L-iduronic acid, idaric acid, glucaric acid. Any of the products can be produced using glucose as a substrate or using any intermediate in any of the methods or pathways of the invention.

20 Claims, 20 Drawing Sheets

(56) References Cited

OTHER PUBLICATIONS

Tong,Xinli et al.: *"Biomass into chemicals: Conversion of sugars to furan derivatives by catalytic processes"*; Applied Catalysis A: General, 385 (2010); pp. 1-13.
Wikipedia: *"2,5-Furandicarboxylic acid"*; Wikipedia—The Free Encyclopedia, Aug. 3, 2012, 5 pgs, http://en.wikipedia.org/wiki/2,5-Furandicarboxylic_acid.
Dirkx et al.: *"The oxidation of gluconic acid with platinum on carbon as catalyst"*; J. Catalysis, 1981, vol. 67, 1981, pp. 14-20.
Extended European Search Report issued on May 16, 2016, regarding EP 13 83 8235.
McKinlay et al.: *"A genomic perspective on the potential of Actinobacillus succinogenes for industrial succinate production"*; BMC Genomics, vol. 11, 2010, pp. 1(680)-16(695).
Takase et al.: *"Molecular identification of unsaturated uronate reductase prerequisite for alginate metabolism in Spingomonas*sp. A1"; Biochimica et Biophysica Acta, vol. 1804, 2010, pp. 1925-1936.
Gandini et al.: Furans in Polymer Chemistry; Prog. Polym. Sci., 1997, 22, 1203-1379.
Otera et al.: *"Esterification: Methods, Reactions, and Applications"*, Second Edition. Chapter 1. 2010 Wiley-VCH Verlag GmbH & Co. KGaA. Published Online Feb. 2, 2010.
Palmer et al.: *"Evolution of Enzymatic Activities in the Enolase Superfamily: Partitioning of Reactive Intermediates by(D)-Glucarate Dehydratase from Pseudomonas putida"*; Biochemistry. Oct. 1998, 13;37(41):14350-7.

* cited by examiner

5-KGA L-Iduronic L-Idaric DDG

Scheme 6

COMPOSITIONS AND METHODS FOR PRODUCING CHEMICALS AND DERIVATIVES THEREOF

CROSS-REFERENCE TO RELATED APPLICATIONS

This application is a continuation-in-part of U.S. application Ser. No. 14/033,300, filed Sep. 20, 2013, which claims the benefit of priority under 35 U.S.C. §119(e) of U.S. provisional application Ser. No. 61/704,408, filed Sep. 21, 2012, which are each hereby incorporated by reference in their entireties, including all tables, figures, and claims.

INCORPORATION OF SEQUENCE LISTING

The material in the accompanying Sequence Listing is hereby incorporated by reference into this application. The accompanying sequence listing text file, name SGI1660-2_txt, was created on Mar. 21, 2014 and is 190 KB. The file can be assessed using Microsoft Word on a computer that uses Windows OS.

BACKGROUND OF THE INVENTION

In recent years, an increasing effort has been devoted to identify new and effective ways to use renewable feedstocks for the production of organic chemicals. Among a plethora of downstream chemical processing technologies, the conversion of biomass-derived sugars to value-added chemicals is considered very important. In particular, six-carboned carbohydrates, i.e. hexoses such as fructose and glucose, are widely recognized the most abundant monosaccharides existing in nature, therefore can be suitably and economically used as the chemical feedstocks.

The production of furans and furan derivatives from sugars has attracted increasing attention in chemistry and in catalysis studies, and is believed to have the potential to provide one of the major routes to achieving sustainable energy supply and chemicals production. Indeed, dehydration and/or oxidation of the sugars available within biorefineries with integrated biomass conversion processes can lead to a large family of products including a wide range of furans and furan derivatives.

Among the furans having the most commercial values, furan-2,5-dicarboxylic acid (also known as 2,5-furandicarboxylic acid, hereinafter abbreviated as FDCA) is a valuable intermediate with various uses in several industries including pharmaceuticals, pesticides, antibacterial agents, fragrances, agricultural chemicals, as well as in a wide range of manufacturing applications of polymer materials, e.g. bioplastic resins. As such, FDCA is considered a green alternative of terephthalic acid (TPA), a petroleum-based monomer that is one of the largest-volume petrochemicals produced yearly worldwide. In fact, the US Department of Energy has identified FDCA as one of the top 12 priority compounds made from sugars into a value-added chemical for establishing the "green" chemistry of the future, and as such, it has been named one of the "sleeping giants" of the renewable intermediate chemicals (Werpy and Petersen, *Top Value Added Chemicals from Biomass*. US Department of Energy, Biomass, Vol 1, 2004).

Although various methods have been proposed for commercial scale production of FDCA (for review, see, e.g., Tong et al., *Appl. Catalysis A: General,* 385, 1-13, 2010), the main industrial synthesis of FDCA currently relies on a chemical dehydration of hexoses, such as glucose or fructose, to the intermediate 5-hydroxymethylfurfural (5-HMF), followed by a chemical oxidation to FDCA. However, it has been reported that current FDCA production processes via dehydration are generally nonselective, unless immediately upon their formation, the unstable intermediate products can be transformed to more stable materials. Thus, the primary technical barrier in the production and use of FDCA is the development of an effective and selective dehydration process from biomass-derived sugars.

It is therefore desirable to develop methods for production of this highly important compound, as well as many other chemicals and metabolites, by alternative means that not only would substitute renewable for petroleum-based feedstocks, but also use less energy and capital-intensive technologies. In particular, the selective control of sugar dehydration could be a very powerful technology, leading to a wide range of additional, inexpensive building blocks.

SUMMARY OF THE INVENTION

The present invention provides methods for producing a product of one or more enzymatic pathways. The pathways used in the methods of the invention involve one or more conversion steps such as, for example, an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid Step 7b); and an enzymatic conversion of 5-ketogluconate into 4,6-dihydroxy 2,5-diketo hexanoate (2,5-DDH) (Step 16); an enzymatic conversion of 1,5-gluconolactone to gulurono-lactone (Step 19). In some embodiments the methods of the invention produce 2,5-furandicarboxylic acid (FDCA) as a product. The methods can include both enzymatic and chemical conversions as steps. Various pathways are also provided for converting glucose or fructose or sucrose or galactose into 5-dehydro-4-deoxy-glucarate (DDG), and for converting the same sugars into FDCA. The methods can also involve the use of engineered enzymes that perform reactions with high specificity and efficiency.

In a first aspect the invention provides a method for producing a product of an enzymatic or chemical pathway from a starting substrate. The pathway can contain any one or more of the following conversion steps: an enzymatic conversion of guluronic acid into D-glucarate (Step 7); an enzymatic conversion of 5-ketogluconate (5-KGA) into L-Iduronic acid (Step 15); an enzymatic conversion of L-Iduronic acid into Idaric acid (Step 7b); and an enzymatic conversion of 5-ketocluconate into 4,6-dihydroxy 2,5-diketo hexanoate (2,5-DDH) (Step 16); an enzymatic conversion of 1,5-gluconolactone to gulurono-lactone (Step 19).

In one embodiment the product of the enzymatic pathway is 5-dehydro-4-deoxy-glucarate (DDG). In various embodiments the substrate of the method can be glucose, and the product can 5-dehydro-4-deoxy-glucarate (DDG). The method can involve the steps of the enzymatic conversion of D-glucose to 1,5-gluconolactone (Step 1); the enzymatic conversion of 1,5-gluconolactone to gulurono-lactone (Step 19); the enzymatic conversion of gulurono-lactone to guluronic acid (Step 1B); the enzymatic conversion of guluronic acid to D-glucarate (Step 7); and the enzymatic conversion of D-glucarate to 5-dehydro-4-deoxy-glucarate (DDG) (Step 8).

In another method of the invention the substrate is glucose and the product is DDG, and the method involves the steps of: the conversion of D-glucose to 1,5-gluconolactone (Step 1); the conversion of 1,5-gluconolactone to gluconic acid (Step 1a); the conversion of gluconic acid to 5-ketogluconate (5-KGA) (Step 14); the conversion of 5-ketogluconate (5-KGA) to L-Iduronic acid (Step 15); the conversion of L-Iduronic acid to Idaric acid (Step 7b); and the conversion of Idaric acid to DDG (Step 8a).

In another method of the invention the substrate is glucose and the product is DDG and the method involves the steps of the conversion of D-glucose to 1,5-gluconolactone (Step 1); the conversion of 1,5-gluconolactone to gluconic acid (Step 1a); the conversion of gluconic acid to 5-ketogluconate (5-KGA) (Step 14); the conversion of 5-ketogluconate (5-KGA) to 4,6-dihydroxy 2,5-diketo hexanoate (2,5-DDH) (Step 16); the conversion of 4,6-dihydroxy 2,5-diketo hexanoate (2,5-DDH) to 4-deoxy-5-threo-hexosulose uronate (DTHU) (Step 4); and the conversion of 4-deoxy-5-threo-hexosulose uronate (DTHU) to DDG (Step 5).

In another method of the invention the substrate is glucose and the product is DDG, and the method involves the steps of: the conversion of D-glucose to 1,5-gluconolactone (Step 1); the conversion of 1,5-gluconolactone to gluconic acid (Step 1a); the conversion of gluconic acid to 5-ketogluconate (5-KGA) (Step 14); the conversion of 5-ketogluconate (5-KGA) to L-Iduronic acid (Step 15); the conversion of L-Iduronic acid to 4-deoxy-5-threo-hexosulose uronate (DTHU) (Step 7B); and the conversion of 4-deoxy-5-threo-hexosulose uronate (DTHU) to DDG (Step 5).

Any of the methods disclosed herein can further involve the step of converting the DDG to 2,5-furan-dicarboxylic acid (FDCA). Converting the DDG to FDCA in any of the methods can involve contacting DDG with an inorganic acid to convert the DDG to FDCA.

In another aspect the invention provides a method for synthesizing derivatized (esterified) FDCA. The method involves contacting DDG with an alcohol, an inorganic acid at a temperature in excess of 60 C to form derivatized FDCA. In different embodiments the alcohol is methanol, butanol or ethanol.

In another aspect the invention provides a method for synthesizing a derivative of FDCA. The method involves contacting DDG with an alcohol, an inorganic acid, and a co-solvent to produce a derivative of DDG; optionally purifying the derivative of DDG; and contacting the derivative of DDG with an inorganic acid to produce a derivative of FDCA. The inorganic acid can be sulfuric acid and the alcohol can be ethanol or butanol. In various embodiments the co-solvent can be any of THF, acetone, acetonitrile, an ether, butyl acetate, an dioxane, chloroform, methylene chloride, 1,2-dichloroethane, a hexane, toluene, and a xylene.

In one embodiment in the derivative of DDG is di-ethyl DDG and the derivative of FDCA is di-ethyl FDCA, and in another embodiment the derivative of DDG is di-butyl DDG and the derivative of FDCA is di-butyl FDCA.

In another aspect the invention provides a method for synthesizing FDCA. The method involves contacting DDG with an inorganic acid in a gas phase.

In another aspect the invention provides a method for synthesizing FDCA. The method involves contacting DDG with an inorganic acid at a temperature in excess of 120 C.

In another aspect the invention provides a method for synthesizing FDCA. The method involves contacting DDG with an inorganic acid under anhydrous reaction conditions.

DETAILED DESCRIPTION OF THE INVENTION

Figure 1:
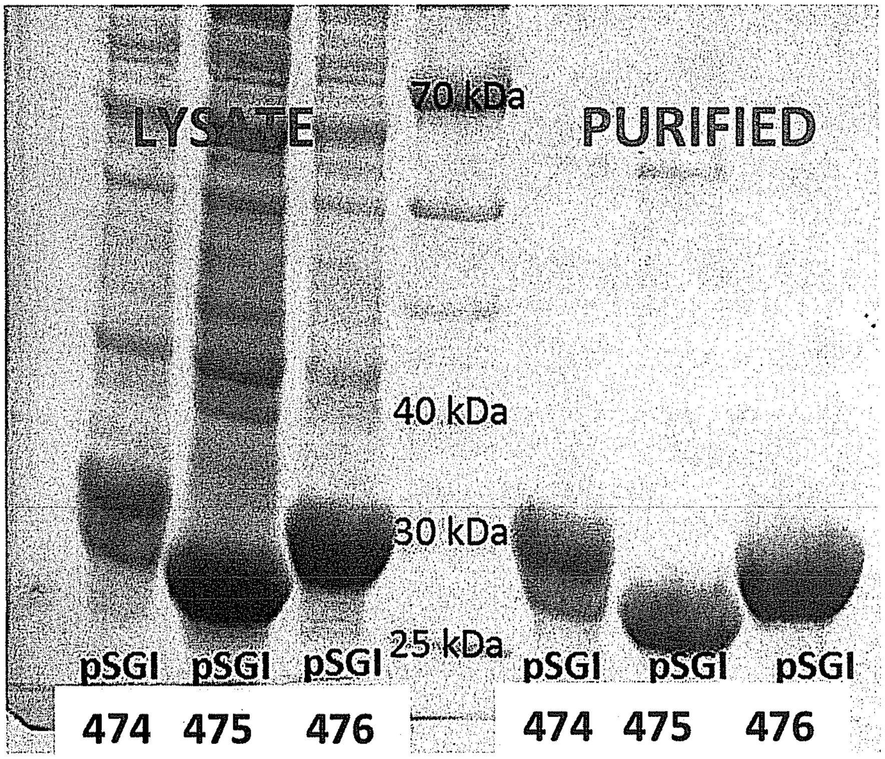
FIG. 1 is a electrophoretic gel of crude lysates and purified enzymes of proteins 474, 475, and 476.

The present invention provides methods for producing a product of an enzymatic pathway. The methods can comprise the enzymatic conversion of a substrate into a product. By utilizing the enzymatic and chemical pathways of the invention it is possible to synthesize a wide variety of products in a highly efficient and economical manner. One product that can be produced by the methods and pathways of the invention is 2,5-furanyl dicarboxylic acid (FDCA), which can be produced at commercial scales according to the invention. The methods can comprise one or more enzymatic and/or chemical substrate-to-product conversion steps disclosed herein. In some embodiments the enzymes utilized perform enzymatic conversion steps using activities unknown for the enzymes. These novel activities can therefore be employed in the invention to perform the conversion steps and perform a substrate to product conversion as part of a enzymatic and/or chemical pathway. Any of the products of any of the pathways disclosed herein (e.g., DDG, iduronic acid, idaric acid, glucaric acid, FDCA, etc.) can be produced on a commercial scale. i.e. in quantities of at least 1 gram or at least 10 grams or at least 100 grams or at least 1 kg in a single bioreactor or reaction vessel, as disclosed herein.

The pathways of the invention are comprised of any one or more of the steps disclosed herein. It is understood that a step of a pathway of the invention can involve the forward reaction or the reverse reaction, i.e., the substrate A being converted into product B, while in the reverse reaction substrate B is converted into product A. In the methods both the forward and the reverse reactions are described as the step unless otherwise noted.

The methods involve producing a product of a pathway, which can be an enzymatic pathway. The methods involve one or more enzymatic and/or chemical conversion steps, which convert a substrate to a product. Steps that can be included in the methods include, for example, any one or more of: an enzymatic conversion of guluronic acid into D-glucarate (Step 7); an enzymatic conversion of L-Iduronic acid to 4-deoxy-5-threo-hexosulose uronate (DTHU) (17); an enzymatic conversion of 5-ketogluconate (5-KGA) into L-Iduronic acid (Step 15); an enzymatic conversion of L-Iduronic acid into Idaric acid Step 7B); and an enzymatic conversion of 5-ketocluconate into 4,6-dihydroxy 2,5-diketo hexanoate (2,5-DDH) (Step 16); an enzymatic conversion of 1,5-gluconolactone to gulurono-lactone (Step 19). Any one or more of the aforementioned steps can be included in a method or pathway of the invention. An enzymatic step or pathway is a step or pathway that requires an enzyme as a catalyst in the reaction to make the step proceed. Chemical steps can be performed without an enzyme as a catalyst in the reaction. Any one or more of the steps recited in the methods can be an enzymatic step. In some embodiments every step of the pathway is an enzymatic step, while in other embodiments one or more steps in the pathway is a chemical step.

In some embodiments any of the methods can include a step involving the addition of the substrate of the reaction to a reaction mix containing the enzyme that performs the conversion. Thus the method of converting guluronic acid into D-glucarate (step 7) can involve the addition of guluronic acid as starting substrate to the reaction mix; the enzymatic conversion of L-iduronic acid to Idaric acid (7B) can involve the addition of L-Iduronic acid as starting substrate to the reaction mix; the enzymatic conversion of L-Iduronic acid to 4-deoxy-5-threo-hexosulose uronate (DTHU) (17) can involve the addition of L-iduronic acid as starting substrate to the reaction mix. Any of the methods can involve a step of adding glucose, fructose, galactose, sucrose, or mannose or another mono- or di-saccharide to the reaction mixture. Another step that can be included in any of the methods is a step of purifying from the reaction mixture a reaction product. Thus, a step of purifying glucaric acid/D-glucarate or L-Iduronic acid/iduronate, or Idaric acid, or 2,5-diketo hexanedioic/DKHA can be included in any of the methods described herein. Any of the methods disclose can include a step of isolating or purifying DDG or FDCA from the reaction mixture. And any of the methods can involve a step of adding an enzyme that performs any one or more of the steps described herein to the reaction mixture. A reaction mixture is a mixture of at least one substrate and at least one enzyme and involves the conversion of at least one substrate into a least one enzyme product. Any of the methods can involve a step of adding an isolated enzyme to a reaction mix, the enzyme performing a substrate to product conversion step of a pathway of the invention, and the isolated enzyme being at least 10% purified or at least 20% purified or at least 25% purified or at least 50% purified or at least 70% purified or at least 80% purified or at least 90%, all w/w.

Since many sugars can be converted into other sugars any of the methods or pathways of the invention can involve the use of glucose, sucrose, fructose or galactose as the starting substrate. Thus, in any pathway or reaction disclosed herein where glucose is the starting substrate it is understood that fructose or sucrose or galactose or mannose or another starting substrate can also be a starting substrate for that pathway or reaction. In some embodiments the sugar is converted into glucose which then enters the pathway but in other embodiments the pathway begins with fructose or sucrose or galactose or mannose or another mono- or di-saccharide.

The reactions of the invention can occur in a lysate of cells or a cell-free lysate that contains one or more enzymes that perform the enzymatic conversion, but can also occur in a reaction mixture containing components added by the user to form a reaction mixture, or can contain components purified from a cell lysate, or may be contained in a whole cell biocatalyst. The reaction can also occur in a mix made of purified components that have been combined, such as in a mix where the substrate and enzyme were combined to form the reaction mix. The reactions can occur in an in vitro reaction or can occur in a recombinant cell, and therefore the product(s) can be harvested by lysing the cells or by collecting from the culture medium. The reactions can occur in a laboratory container or reaction vessel such as, for example, a centrifuge tube, a test tube, a vial, a beaker, or a glass or metal or plastic container or reactor, a fermenter or fermentation vessel or bioreactor, an algae pond, any of which can be small scale or large scale. Any of the organisms described herein can be utilized as host cells to produce the product of a step or pathway of the invention. The organisms can also be used to produce one or more enzymes of the invention for use in a method of the invention. Various types of organisms can be used. Examples include: bacteria of the family Acetobacteraceae (e.g. bacteria of the genus *Acetobacter, Acidiphilium, Gluconobacter, Gluconoacetobacter*), or bacteria of the family Pseudomonadaceae (e.g., genus *Azotobacter, Pseudomonas*), or bacteria of the family Enterobacteriacea (e.g., of the genus *Escherichia* (e.g., *E. coli*), *Klebsiella*). Yeast can also be used for these purposes such as yeast of the genera *Saccharomyces, Ashbya, Kluveromyces, Lachancea, Zygosaccharomyces, Candida, Pichia, Arxula* or *Trichosporon* or *Blastobotrys*. Cyanobacteria can also be used such as those of the genus *Cyanothece* (e.g. *Cyanothece* strains ATCC 51142, PCC 7424, PCC 7425, PCC 7822, PCC 8801, PCC 8802), or *Microcystis* or

*Synechococcus* (e.g., strains elongatus PCC 7942, PCC 7002, PCC 6301, CC9311, CC9605, CC9902, JA-2-3B'a(2-13), JA-3-3Ab, RCC307, WH 7803, WH 8102) or *Synechocystis*, or *Thermosynechococcus*. Thus the present invention provides recombinant host cells comprising a recombinant nucleic acid of one or more of SEQ ID NOs: 4-6, 20-32, 36-38, 47-54, 56, 62-66, 69-70, 72, and 79-84 or a codon-optimized sequence of any of SEQ ID NOs: 1-84. The host cells can also contain a vector of the invention described herein. A "codon optimized" sequence refers to changes in the codons of a sequence to those preferentially used in a particular organism so that the encoded protein is efficiently expressed in the organism carrying the sequence. The recombinant nucleic acid sequence can be comprised on a vector, as disclosed herein.

In various embodiments the methods of the invention are methods of converting glucose or fructose or sucrose or galactose to DDG, or glucose or fructose or sucrose or galactose to FDCA, or glucose or fructose or sucrose or galactose to DTHU or DEHU, or for converting DDG to FDCA. The methods can involve converting the starting substrate in the method into the product. The starting substrate is the chemical entity considered to begin the method and the product is the chemical entity considered to be the final end product of the method. Intermediates are those chemical entities that are created in the method (whether transiently or permanently) and that are present in the reaction pathway between the starting substrate and the product. In various embodiments the methods and pathways of the invention have about four or about five intermediates or 4-5 intermediates, or about 3 intermediates, or 3-5 intermediates, or less than 6 or less than 7 or less than 8 or less than 9 or less than 10 or less than 15 or less than 20 intermediates, meaning these values not counting the starting substrate or the final end product.

The invention provides methods of producing FDCA and/or DDG, from glucose or fructose or sucrose or galactose that have high yields. The theoretical yield is the amount of product that would be formed if the reaction went to completion under ideal conditions. In different embodiments the methods of the invention produce DDG from glucose, fructose, or galactose with a theoretical yield of at least 50% molar, or at least 60% molar or at least 70% molar, or at least 80% molar, at least 90% molar or at least 95% molar or at least 97% molar or at least 98% molar or at least 99% molar, or a theoretical yield of 100% molar. The methods of the invention also can provide product with a carbon conservation of at least 80% or at least 90% or at least 95% or at least 97% or at least 98% or at least 99% or 100%, meaning that the particular carbon atoms present in the initial substrate are present in the end product of the method at the recited percentage. In some embodiments the methods produce DDG and/or FDCA from glucose or fructose or sucrose or galactose via dehydration reactions.

Example Synthesis Routes

The invention also provides specific pathways for synthesizing and producing a desired product. Any of the following described routes or pathways can begin with glucose or fructose or sucrose or galactose or mannose and flow towards a desired product. In some embodiments D-glucose is the starting substrate and the direction of the pathway towards any intermediate or final product of the pathway is considered to be in the downstream direction, while the opposite direction towards glucose is considered the upstream direction. It will be realized that routes or pathways can flow in either the downstream or upstream direction. While glucose is used as an example starting substrate for pathways described herein, it is also understood that sucrose, fructose, galactose, or mannose or any intermediate in any of the pathways can also be the starting substrate in any method of the invention, and DDG, DTHU, FDCA, or any intermediate in any of the routes or pathways of the invention can be the final end product of a method of the invention. The disclosed methods therefore include any one or more steps disclosed in any of the routes or pathways of the invention for converting any starting substrate or intermediate into any end product or intermediate in the disclosed routes or pathways using one or more of the steps in the disclosed routes or pathways. Thus, for example the methods can be methods for converting glucose or fructose or sucrose or galactose or mannose to DDG, or to guluronic acid, or to galactarate, or to DTHU, or to DEHU, or to guluronic acid, or to iduronic acid, or to idaric acid, or to glucaric acid, or for converting galactarate to DDG, or for converting guluronic acid to D-glucarate, or for converting 5-KGA to L-Iduronic acid, or for converting L-Iduronic acid to Idaric acid, or for converting 5-KGA to 2,5-DDH or DTHU, or for converting DHG to DEHU. In these embodiments the methods utilize the steps disclosed in the methods and pathways of the invention from starting substrate to the relevant end product. One or more of the steps can also be utilized in methods flowing in the "opposite" or upstream direction from the pathways disclosed herein.

Figure 2A:
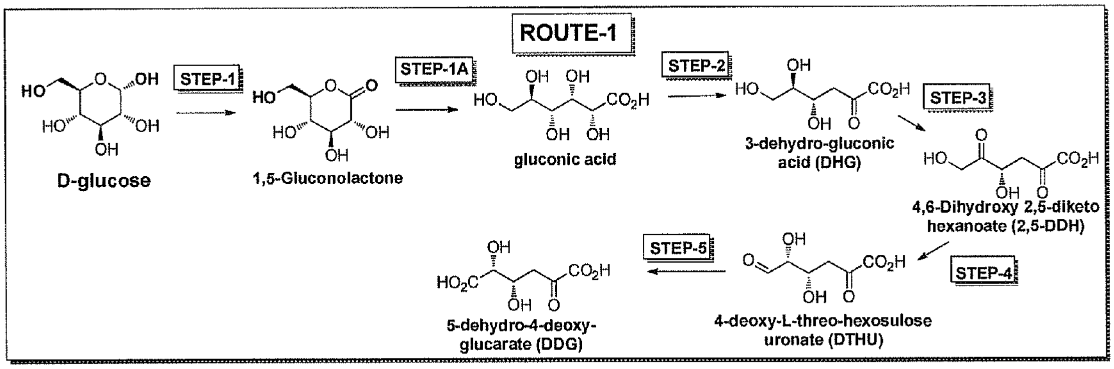
FIGS. 2*a-h* is a schematic illustration of the pathways of Routes 1, 2, 2A, 2C, 2D, 2E, 2F, respectively.

Route 1 is illustrated in FIG. 2*a*. Route 1 converts D-glucose (or any intermediate in the pathway) into 5-dehydro-4-deoxy-glucarate (DDG) via an enzymatic pathway via a series of indicated steps. Route 1 converts D-glucose into DDG via a pathway having 1,5-gluconolactone, gluconic acid, 3-dehydro-gluconic acid (DHG), 4,6-dihydroxy 2,5-diketo hexanoate (2,5-DDH), and 4-deoxy-L-threo-hexosulose uronate (DTHU) as intermediates and DDG as the final end product. For any of the pathways additional intermediates not shown can also be present. The steps are the enzymatic conversion of D-glucose to 1,5-gluconolactone (Step 1); the enzymatic conversion of 1,5-gluconolactone to gluconic acid (Step 1A); the enzymatic conversion of gluconic acid to 3-dehydro-gluconic acid (DHG) (Step 2); the enzymatic conversion of 3-dehydro-gluconic acid (DHG) to 4,6-dihydroxy 2,5-diketo hexanoate (2,5-DDH) (Step 3); the enzymatic conversion of 4,6-dihydroxy 2,5-diketo hexanoate (2,5-DDH) to 4-deoxy-L-threo-hexosulose uronate (DTHU) (Step 4); and the enzymatic conversion of 4-deoxy-L-threo-hexosulose uronate (DTHU) to 5-dehydro-4-deoxy glucarate (DDG) (Step 5). Route 1 also comprises sub-routes where the glucose or any intermediate in the pathway as a substrate is converted into any other downstream intermediate as final product, and each substrate to product sub-route is considered disclosed as if each is set forth herein in full.

Figure 2B:
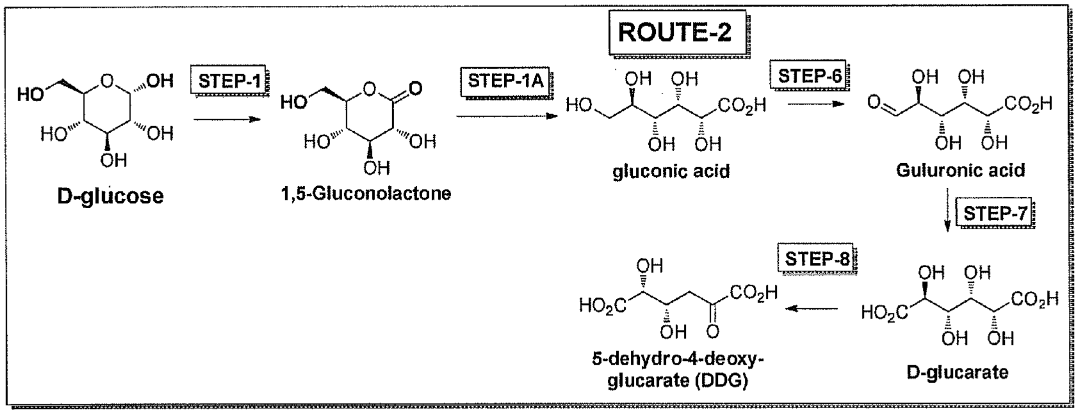

Route 2 is illustrated in FIG. 2*b* and converts D-glucose into DDG. The steps in the Route 2 pathway are the enzymatic conversion of D-glucose into 1,5-gluconolactone (Step 1); the enzymatic conversion of 1,5-gluconolactone to gluconic acid (Step 1A); the enzymatic conversion of gluconic acid to guluronic acid (Step 6); the enzymatic conversion of guluronic acid to D-glucarate (Step 7); the enzymatic conversion of D-glucarate to DDG (Step 8). Route 2 also comprises sub-routes where glucose or any intermediate in the pathway as substrate is converted into any other downstream intermediate as final product, and each sub-route is considered disclosed as if each is set forth herein in full. For example in some embodiments the methods comprise steps for the conversion of glucose or gluconic acid as substrate into guluronic acid or D-glucarate as product using one or more of the steps described in Route 2.

Figure 2C:
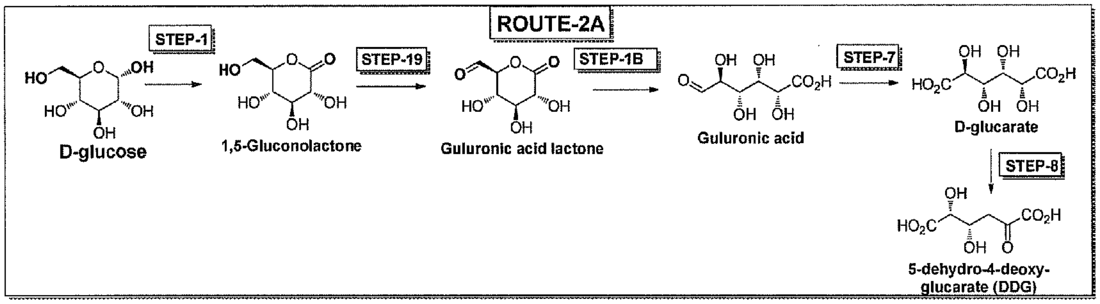

Route 2A is illustrated in FIG. 2*c*. The steps in Route 2A are the enzymatic conversion of D-glucose to 1,5-glucono-lactone (Step 1); the enzymatic conversion of 1,5-glucono-lactone to guluronic acid lactone (Step 19); the enzymatic conversion of guluronic acid lactone to guluronic acid (Step 1B); the enzymatic conversion of guluronic acid to D-glucarate (Step 7); the enzymatic conversion of D-glucarate to 5-dehydro-4-deoxy-glucarate (DDG) (Step 8). Route 2A also comprises sub-routes where glucose or any intermediate in the pathway as starting substrate is converted into any other downstream intermediate as final end product, and each sub-route is considered disclosed as if each is set forth herein in full. For example in some embodiments the methods comprise steps for the conversion of glucose or guluronic acid lactone as substrate into glucarate or DDG as product using one or more of the steps described in Route 2A.

Figure 2D:
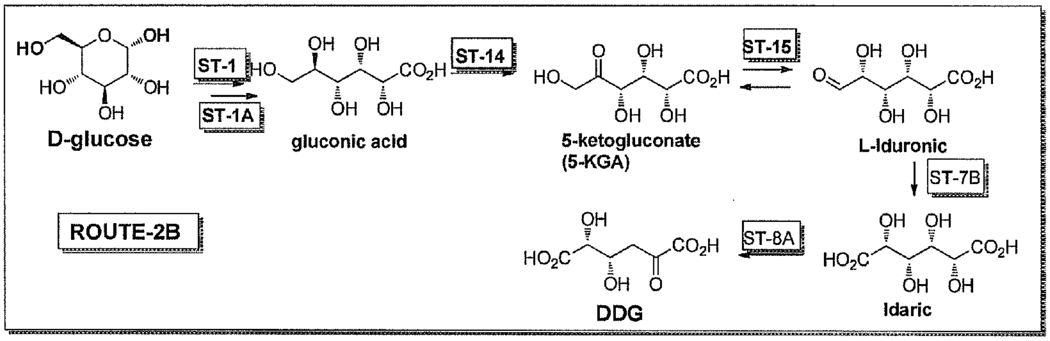

Route 2B is illustrated in FIG. 2*d*. The steps in Route 2B are the enzymatic conversion of D-glucose into gluconic acid (Steps 1 and 1A); the enzymatic conversion of gluconic acid into 5-ketogluconate (5-KGA) (Step 14); the enzymatic conversion of 5-KGA into L-Iduronic acid (Step 15); the enzymatic conversion of L-Iduronic acid into Idaric acid (Step 7B); the enzymatic conversion of Idaric acid into DDG (Step 8A). Route 2B also comprises sub-routes where glucose or any intermediate in the pathway as starting substrate is converted into any other downstream intermediate as final end product, and each sub-route is considered disclosed as if each is set forth herein in full. For example in some embodiments the methods comprise steps for the conversion of glucose or 5-KGA as substrate into iduronic acid or idaric acid as product using one or more of the steps described in Route 2B.

Figure 2E:
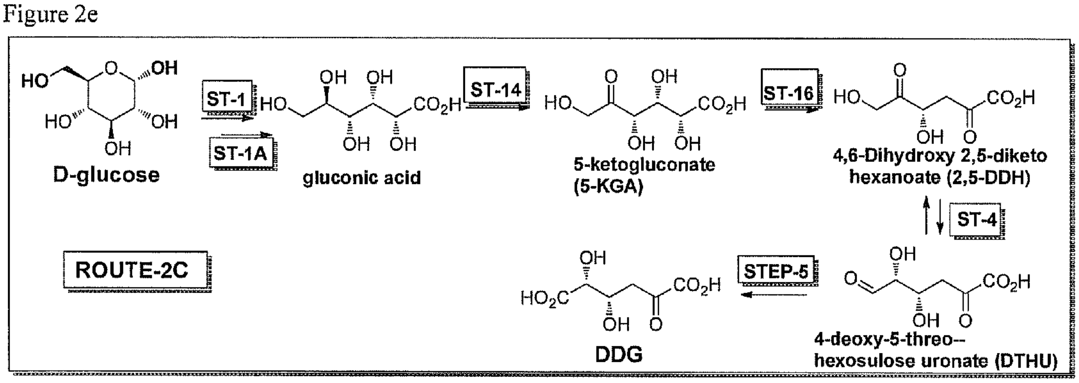

Route 2C is illustrated in FIG. 2*e*. The steps in Route 2C are the enzymatic conversion of D-glucose to gluconic acid (Steps 1 and 1A); the enzymatic conversion of gluconic acid to 5-ketogluconate (5-KGA) (Step 14); the enzymatic conversion of 5-KGA to 4,6-dihydroxy 2,5-diketo hexanoate (2,5-DDH) (Step 16); the enzymatic conversion of 4,6-dihydroxy 2,5-diketo hexanoate (2,5-DDH) to 4-deoxy-5-threo-hexosulose uronate (DTHU) (Step 4); the enzymatic conversion of DTHU to DDG (Step 5). Route 2C also comprises sub-routes where glucose or any intermediate in the pathway as starting substrate is converted into any other downstream intermediate as final end product, and each sub-route is considered disclosed as if each is set forth herein in full. For example in some embodiments the methods comprise steps for the conversion of glucose or gluconic acid as substrate into 2,5-DDH or DTHU using one or more steps described in Route 2C.

Figure 2F:
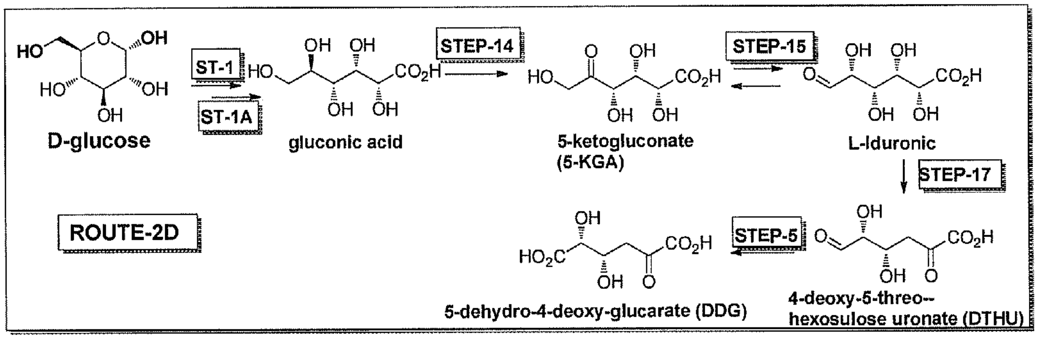

Route 2D is illustrated in FIG. 2*f*. The steps in Route 2D are the enzymatic conversion of D-glucose to gluconic acid (Steps 1 and 1A); the enzymatic conversion of gluconic acid to 5-ketogluconate (5-KGA) (Step 14); the enzymatic conversion of 5-KGA to Iduronic acid (Step 15); the enzymatic conversion of L-Iduronic acid to DTHU (Step 17); the enzymatic conversion of DTHU to DDG (Step 5). Route 2D also comprises sub-routes where glucose or any intermediate in the pathway as starting substrate is converted into any other downstream intermediate as final end product, and each sub-route is considered disclosed as if each is set forth herein in full. For example in some embodiments the methods comprise steps for the conversion of glucose or 5-KGA as substrate into L-iduronic acid or DTHU using one or more of the steps described in Route 2D.

Figure 2G:
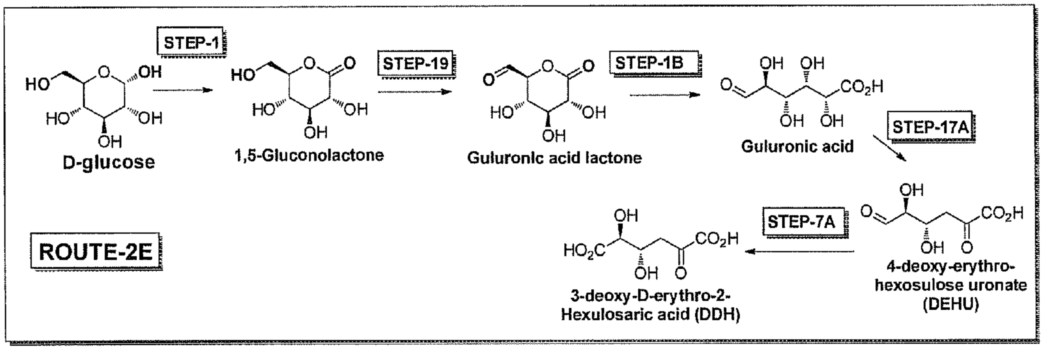

Route 2E is illustrated in FIG. 2*g*. The steps in Route 2D are the enzymatic conversion of D-glucose to 1,5-glucono-lactone (Step 1); the enzymatic conversion of 1,5-glucono-lactone to guluronic acid lactone (Step 19); the enzymatic conversion of guluronic acid lactone to guluronic acid (Step 1B); the enzymatic conversion of guluronic acid to 4-deoxy-erythro-hexosulose uronate (DEHU) (Step 17A); the enzymatic conversion of DEHU to 3-deoxy-D-erythro-2-hexylosaric acid (DDH) (Step 7A). Route 2E also comprises sub-routes where glucose or any intermediate in the pathway as starting substrate is converted into any other downstream intermediate as final end product, and each sub-route is considered disclosed as if each is set forth herein in full. For example in some embodiments the methods comprise steps for the conversion of glucose as substrate into guluronic acid or DEHU using one or more of the steps described in Route 2E.

Figure 2H:
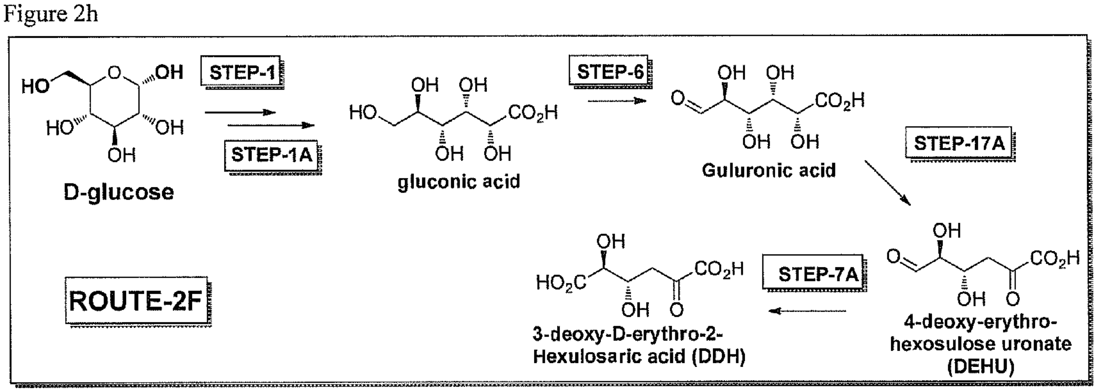

Route 2F is illustrated in FIG. 2*h*. The steps in Route 2F are the enzymatic conversion of D-glucose to gluconic acid (Steps 1 and 1A); the enzymatic conversion of gluconic acid to guluronic acid (Step 6); the enzymatic conversion of guluronic acid to 4-deoxy-erythro-hexosulose uronate (DEHU) (Step 17A); the enzymatic conversion of DEHU to 3-deoxy-D-erythro-2-hexulosaric acid (DDH) (Step 7A). Route 2F also comprises sub-routes where glucose or gluconic acid or any intermediate in the pathway as starting substrate is converted into guluronic acid or DDH or any other downstream intermediate as final end product using one or more of the steps of Route 2F, and each sub-route is considered disclosed as if each is set forth herein in full.

Figure 3A:
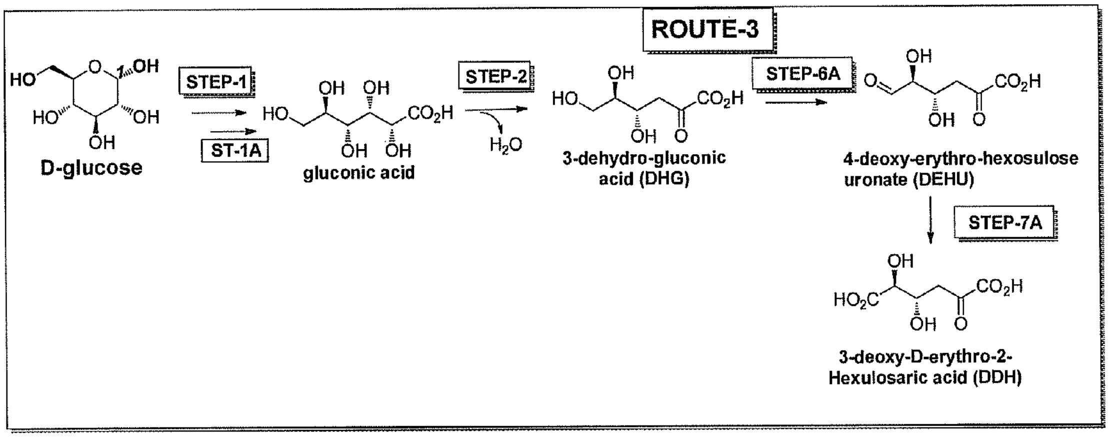
FIGS. 3*a-c* present a schematic illustration of the pathways of Routes 3, 4, and 5, respectively.

Route 3 is illustrated in FIG. 3*a*. The steps in Route 3 are the enzymatic conversion of D-glucose to gluconic acid (Steps 1 and 1A); the enzymatic conversion of gluconic acid to 3-dehydro-gluconic acid (DHG) (Step 2); the enzymatic conversion of DHG to 4-deoxy-erythro-hexosulose uronate (DEHU) (Step 6A); the enzymatic conversion of DEHU to DDG (Step 7A). Route 3 also comprises sub-routes where glucose or fructose or sucrose or galactose or any intermediate in the pathway as starting substrate is converted into gluconic acid or DDH any other downstream intermediate of Route 3 as final end product using one or more of the steps of Route 3, and each sub-route is considered disclosed as if each is set forth herein in full.

Figure 3B:
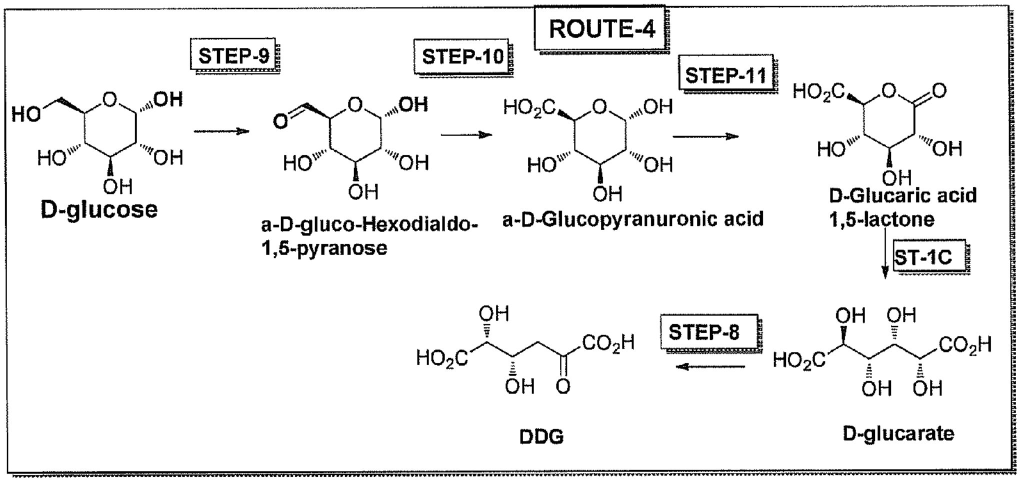

Route 4 is illustrated in FIG. 3*b*. The steps in Route 4 are the enzymatic conversion of D-glucose to a-D-gluco-hexodialdo-1,5-pyranose (Step 9); the enzymatic conversion of a-D-gluco-hexodialdo-1,5-pyranose to a-D-glucopyranuronic acid (Step 10); the enzymatic conversion of a-D-glucopyranuronic acid to D-glucaric acid 1,5-lactone (Step 11); the enzymatic conversion of D-glucaric acid 1,5-lactone to D-glucarate (Step 1C); the enzymatic conversion of D-glucarate to DDG (Step 8). Route 4 also comprises sub-routes where glucose or any intermediate in the pathway as starting substrate is converted into glucarate or DDG or any other downstream intermediate as final end product using one or more of the steps of Route 4, and each sub-route is considered disclosed as if each is set forth herein in full.

Figure 3C:
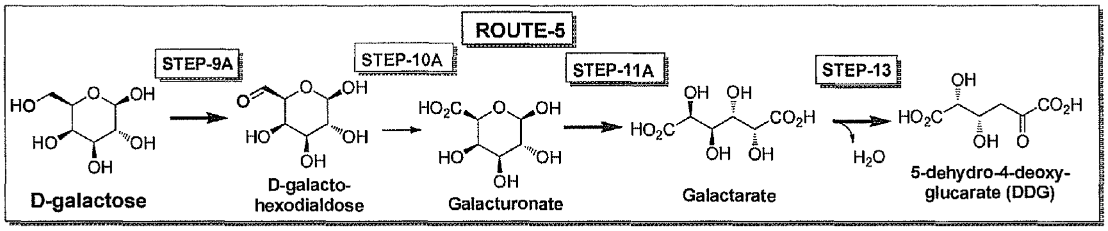

Route 5 is illustrated in FIG. 3*c*. The steps in Route 5 are the enzymatic conversion of D-galactose to D-galacto-hexodialdose (Step 9A); the enzymatic conversion of D-galacto-hexodialdose to galacturonate (Step 10A); the enzymatic conversion of galacturonate to galactarate (Step 11A); the enzymatic conversion of galactarate to DDG (Step 13). Route 5 also comprises sub-routes where galactose or any intermediate in the pathway as starting substrate is converted into any other downstream intermediate as final product, and each sub-route is considered disclosed as if each is set forth herein in full. For example in some embodiments the methods comprise steps for the conversion of galactose or another substrate into galacturonate or galactarate using the steps described in Route 5.

In various other embodiments the invention provides a method of producing a product of an enzymatic and/or chemical pathway from a starting substrate that involves performing Step 1, followed by Step 19, followed by Step 1B to produce a guluronic acid product. Optionally the pathway can continue with Step 7 to produce glucarate. In another embodiment the method involves performing Steps 1 and 1A followed by Step 14, followed by Step 15 to produce Iduronic acid. Optionally the method can continue with Step 7B to produce an Idaric acid product or with Step 17 to produce DTHU. In another embodiment the method involves performing Steps 1 and 1A, followed by Step 14 followed by Step 16 to produce a 2,5-DDH product. In another embodiment the method involves performing Step 1 followed by Step 19 to produce guluronic acid lactone.

The Enzymatic Steps

There are disclosed a wide variety of enzymes (and nucleic acids that encode the enzymes) that can perform the steps of the methods outlined herein. The enzymes utilized in the enzymatic steps of the invention can be proteins or polypeptides. In addition to the families and classes of enzymes disclosed herein for performing the steps of the invention, homologs having a sequence identity to any enzyme or nucleic acid or to any of SEQ ID NOs 1-84, disclosed herein will also be useful in the invention. Enzymes and nucleic acids that are homologs of SEQ ID NOs: 1-84 have a sequence identity of at least 40% or at least 50% or at least 60% or at least 70% or at least 80% or at least 90% or at least 95% or at least 97% or at least 98% or at least 99% to any nucleic acid or enzyme of SEQ ID NO: 1-84, or to a member of an enzyme class disclosed herein. Percent sequence identity or homology with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent identity or homology. Homology or identity at the nucleotide or amino acid sequence level may be determined using methods known in the art, including but not limited to BLAST (Basic Local Alignment Search Tool) analysis using the algorithms employed by the programs blastp, blastn, blastx, tblastn and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. Alternatively a functional fragment of any of the enzymes or nucleic acids encoding such enzymes or of any enzyme or nucleic acid of SEQ ID NOs 1-84 disclosed herein may also be used. The term "functional fragment" refers to a polypeptide that has an amino-terminal and/or carboxy-terminal deletion and/or internal deletion (which can be replaced to form a chimeric protein), where the remaining amino acid sequence has at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the corresponding positions in the reference sequence, and/or that retains about 75%, 80%, 85%, 90%, 91%, 92%, 93%, 94%, 95%, 96%, 97%, 98%, 99%, or 100% of the activity of the full-length polypeptide. The EC numbers provided use the enzyme nomenclature of the Nomenclature Committee of the International Union of Biochemistry and Molecular Biology. In other embodiments the functional fragment retains the requirement of the presence of a co-factor necessary for the activity of a protein or protein encoded by SEQ ID NO:1-84.

Also disclosed is an expression vector having a sequence of SEQ ID NO: 4-6, 20-32, 36-38, 47-54, 56, 62-66, 69-70, 72, and 79-84. The vector can be a bacterial, yeast, or algal vector. Vectors designed for expression of a gene can also include a promoter active in the organism carrying the vector and operably linked to the sequence of the invention. The vector can contain a promoter or expression control sequence operatively linked to a sequence of SEQ ID NOs: 4-6, 20-32, 36-38, 47-54, 56, 62-66, 69-70, 72, and 79-84 or a codon-optimized sequence of any of them. A "promoter" refers to a nucleic acid sequence capable of binding RNA polymerase to initiate transcription of a gene in a 5' to 3' ("downstream") direction. A sequence is "operably linked" to a promoter when the binding of RNA polymerase to the promoter is the proximate cause of said gene's transcription.

Step 1—Conversion (oxidation or dehydrogenation) of glucose to 1,5-gluconolactone. This step can be performed with various enzymes, such as those of the family oxygen dependent glucose oxidases (EC 1.1.3.4) or NAD(P)-dependent glucose dehydrogenases (EC 1.1.1.118, EC 1.1.1.119). *Gluconobacter oxydans* has been shown to efficiently oxidize glucose to gluconic acid and 5-ketogluconate (5-KGA) when grown in a fermentor. Enzymes of the family of soluble and membrane-bound PQQ-dependent enzymes (EC 1.1.99.35 and EC 1.1.5.2) found in *Gluconobacter* and other oxidative bacteria can be used. Quinoprotein glucose is another enzyme that is useful in performing this step. The specific enzyme selected will be dependent on the desired reaction conditions and necessary co-factors that will be present in the reaction, which are illustrated in Table 1.

Step 1A—Conversion (e.g., hydrolysis) of 1,5-gluconolactone to gluconate. This step can be performed chemically in aqueous media and the rate of hydrolysis is dependent on pH (Shimahara, K, Takahashi, T., *Biochim. Biophys. Acta* (1970), 201, 410). Hydrolysis is faster in basic pH (e.g. pH 7.5) and slower in acid pH. Many microorganisms also contain specific 1,5-glucono lactone hydrolases, and a few of them have been cloned and characterized (EC 3.1.1.17; Shinagawa, E *Biosci. Biotechnol. Biochem.* 2009, 73, 241-244).

Step 1B—Conversion of Guluronic acid lactone to guluronic acid. The chemical hydrolysis of guluronic acid lactone can be done by a spontaneous reaction in aqueous solutions. An enzyme capable of catalyzing this hydrolysis is identified amongst the large number of lactonases (EC 3.1.1. XX and more specifically 3.1.1.17, 3.1.1.25).

Step 2—Conversion of gluconic acid to 3-dehydro gluconic acid (DHG): Several enzymes, such as gluconate dehydratases, can be used in the dehydration of gluconic acid to dehydro gluconic acid (DHG). Examples include those belonging to the gluconate dehydratase family (EC 4.2.1.39). A specific example of such a dehydratase has been shown to dehydrate gluconate (Kim, S. Lee, S. B. *Biotechnol. Bioprocess Eng.* (2008), 13, 436). Particular examples of enzymes from this family and their cloning are shown in Example 1.

Step 3: Conversion of 3-dehydro-gluconic acid (DHG) to 4,6-dihydroxy 2,5-diketo hexanoate (2,5-DDH). Enzymes, 2-dehydro-3-deoxy-D-gluconate 5-dehydrogenase (or DHG dehydrogenases) (EC 1.1.1.127) for performing this conversion have been described.

Step 4: Conversion of 4,6-dihydroxy 2,5-diketo hexanoate (2,5-DDH) to 4-deoxy-L-threo-hexosulose uronate (DTHU). Enzymes of the family EC 5.3.1.12 can be used in this step, and Step 15 shows that five such enzymes were cloned and shown to have activity for the dehydration of 5-KGA. These enzymes will also show activity towards 2,5-DDH and DTHU.

Step 5: Conversion of DTHU to 5-dehydro-4-deoxy-glucarate (DDG). DDG can be produced from the chemical or enzymatic oxidation of DTHU, for example with a mild chemical catalyst capable of oxidizing aldehydes in the presence of alcohols. Aldehyde oxidases can be used to catalyze this oxidation. Oxidative bacteria such as *Acetobacter* and *Gluconobacter* (Hollmann et al *Green Chem.* 2011, 13, 226) will be useful in screening. Enzymes of the following families can perform this reaction: aldehyde oxidase EC1.2.3.1, aldehyde ferredoxin oxidoreductase (EC1.2.7.5), and in all the families of EC1.2.1.-XX. Enzymes of the family of uronate dehydrogenases (EC 1.1.1.203) (e.g. see Step 7) will also have this activity. Other enzymes with both alcohol and aldehyde oxidation activity can be used, including enzymes in the alditol oxidase family (see Steps 19 and 6). Other broad substrate oxidases include soluble and membrane bound PQQ-dependent alcohol/aldehyde oxidases. More specifically soluble periplasmic PQQ oxidases enzymes and their homologs belonging into Type I (EC 1.1.9.1) and II (EC 1.1.2.8) families as well as membrane bound PQQ oxidases belonging into EC 1.1.5.X families are useful. In other embodiments aldehyde dehydrogenases/oxidases that act on DTHU can be used.

Step 5 can also be performed using a dehydrogenase from acetic acid bacteria such *Gluconobacter* and *Acetobacter* and *Gluconoacetobacter*, and others. Whole cell activity is identified by screening microorganisms for the oxidation of DTHU. The activity is identified and one or more of the enzymes is cloned. Enzymes with uronate dehydrogenase activity described in Step-7 and 7B are also screened and found to have this activity. A library of soluble periplasmic and membrane bound PQQ-dependent enzymes is also cloned and several enzymes are found having this activity. Some of the enzymes found to have the activity are NAD(P)- or PQQ-dependent dehydrogenases, but others are FAD-dependent aldehyde dehydrogenases. SEQ ID NO: 71-72 are examples of NADP-dependent dehydrogenases, and any one or a combination of them can be used to perform Step 5. SEQ ID NOs: 73-84 are examples of suitable PQQ-dependent dehydrogenases and any one or any combination of them can be used to perform Step 5.

Steps 6 and 6A: Conversion of gluconic acid to guluronic acid (6) and conversion of 3-dehydro-gluconic acid (DHG) to 4-deoxy-5-erythro-hexosulose uronate (DEHU) (6A). The enzymes described in Step 5 are useful for these conversions. Other useful enzymes include NAD(P)-dependent dehydrogenases in the EC 1.1.1.XX families and more specifically glucuronate dehydrogenase (EC 1.1.1.19), glucuronolactone reductase (EC 1.1.1.20). In addition, a large number $O_2$-dependent alcohol oxidases with broad substrate range including sugars will be useful (EC 1.1.3.XX), including sorbitol/mannitol oxidases (EC 1.1.3.40), hexose oxidases (EC 1.1.3.5), alcohol oxidases (EC 1.1.3.13) and vanillin oxidase (EC 1.1.3.38). PQQ-dependent enzymes and enzymes present in oxidative bacteria can also be used for these conversions.

Steps 7 and 7B: Conversion of guluronic acid to D-glucaric acid (7) and conversion of L-Iduronic acid to Idaric acid (7B). These steps can be accomplished with enzymes of the family of uronate dehydrogenases (EC 1.1.1.203) or the oxidases, as described herein. Examples of uronate dehydrogenases include SEQ ID NO: 1-6, and any one or any combination of them can be used to perform Steps 7 and 7B.

Step 7A: Conversion of 4-deoxy-5-erythro-hexosulose uronate (DEHU) to 3-deoxy-D-erythro-2-hexylosaric acid (DDH). The same enzymes described in Step 5 will be useful for performing this conversion. Similar to Step 5, for steps 7 and 7B enzymes are identified having the stated activity, which are NAD(P)- or PQQ-dependent dehydrogenases, but others are FAD-dependent aldehyde dehydrogenases. Examples of NADP-dependent gluconate-5-dehydrogenases include SEQ NO: 71-72 and examples of PQQ-dependent dehydrogenases include SEQ ID NO: 73-84, and any one or any combination of them can be used to perform steps 7 and 7B.

Steps 8 and 8A: Conversion of D-glucaric acid to 5-dehydro-4-deoxy-glucarate (DDG) (Step 8) and conversion of Idaric acid to DDG (Step 8A). Enzymes of the family of glucarate dehydratases (EC 4.2.1.40) can be used to perform these steps. Enzymes of this family have been cloned and have been shown to efficiently convert glucarate to DDG. Two D-glucarate dehydratases (EC 4.2.1.40) were cloned as shown in the Table of cloned glucarate dehydratases below. Both enzymes showed very high activity for the dehydration of Glucarate to DDG using the semicarbazide assay, as described in Step 2.

Cloned glucarate dehydratases

| Organism | pSGI (Vector) | Gene ID | WT/SYN |
|---|---|---|---|
| *E. coli* | 353 (pET28) | P0AES2 | WT |
| *Pseudomonas* (SGI) | 244 | #8114 | WT |

Step 9 and 9A: Conversion of D-glucose to α-D-gluco-hexodialdo-1,5-pyranose (9) and conversion of D-galactose to D-galacto-hexodialdose (9A). Oxidases such as those of the galactose oxidase family (EC 1.1.3.9) can be used in this step. Mutant galactose oxidases are also engineered to have activity on glucose and have been described (Arnold, F. H. et al *ChemBioChem,* 2002, 3(2), 781). Step 9A can be performed with enzymes of the class EC 1.1.3.9.

Step 10: Conversion of α-D-gluco-hexodialdo-1,5-pyranose to α-D-glucopyranuronic acid (step 10) and D-galacto-hexodialdose to galacturonate (10A). This step can be performed using an enzyme of the family of aldehyde dehydrogenases. Also an enzyme identified from those of Step 5 will be useful for both of these conversions.

Step 11 and 11A: Conversion of α-D-glucopyranuronic acid to glucuronic acid 1,5-lactone. Aldehyde dehydrogenases and oxidases as described in Step 5 will be useful in performing this step. Uronate dehydrogenases described in Steps 7 and 7B can also be useful in performing this step. Step-11A is the conversion of galacturonate to galactarate. The uronate dehydrogenase (EC 1.1.1.203), for example those described in Steps 7 and 7B, will be useful in performing this step.

Step 12: Conversion of fructose to glucose. Glucose and fructose isomerases (EC 5.3.1.5) will be useful in performing this step.

Step 13: Conversion of galactarate to 5-dehydro-4-deoxy-D-glucarate (DDG). Enzymes of the family of galactarate dehydrogenases (EC 4.2.1.42) can be used to perform this step, and additional enzymes can be engineered for performing this step.

Step 14: Conversion of gluconate to 5-ketogluconate (5-KGA). A number of enzymes of the family of NAD(P)-dependent dehydrogenases (EC1.1.1.69) have been cloned and shown to have activity for the oxidation of gluconate or the reduction of 5KGA. For example, the NADPH-dependent gluconate 5-dehydrogenase from *Gluconobacter* (Expasy P50199) was synthesized for optimal expression in *E. coli* as shown herein and was cloned in pET24 (pSGI-383). The enzyme was expressed and shown to have the required activities. Additional enzymes useful for performing this step include those of the family of PQQ-dependent enzymes present in *Gluconobacter* (Peters, B. et al. *Appl. Microbiol Biotechnol*., (2013), 97, 6397), as well as the enzymes described in Step 6. Enzymes from these families can also be used to synthesize 5KGA from gluconate.

Step 15: Conversion of 5-KGA to L-Iduronic acid. This step can be performed with various enzymes from different isomerase families, as further described in Example 4. Examples include isomerases of SEQ ID NOs: 7-19 or a homolog having at least 70% sequence identity to an isomerase of SEQ ID NOs: 7-19; or by an isomerase encoded by a nucleic acid of SEQ ID NOs: 20-32 or a homolog of any of them.

Step 16: Conversion of 5-KGA to (4S)-4,6-dihydroxy 2,5-diketo hexanoate (2,5-DDH). This dehydration can be performed with enzymes in the gluconate dehydratase family (EC 4.2.3.39), such as those described in Example 5 or Step 17. Examples of gluconate dehydratases that can be used for Step 16 include SEQ ID NOs 33-35 (encoded by SEQ ID NOs: 36-38, and any one or any combination of them can be used to perform Step 16, or homologs thereof.

Step 17 and 17A: L-Iduronate to 4-deoxy-5-threo-hexosulose uronate (DTHU) and Guluronate to 4-deoxy-erythro-5-hexosulose uronate (DEHU).

Enzymes of the family of dehydratases are identified that can be used in the performance of this step. Enzymes from the families of gluconate or glucarate dehydratases will have the desired activity for performing these steps. Furthermore, many dehydratases of the family (EC 4.2.1.X) will be useful in the performance of these steps. In particular, enzymes that dehydrate 1,2-dyhydroxy acids to selectively produce 2-keto-acids will be useful, such as enzymes of the families: EC 4.2.1.6 (galactonate dehydratase), EC 4.2.1.8 (mannonate dehydratase), EC 4.2.1.25 (arabonate dehydratase), EC 4.2.1.39 (gluconate dehydratase), EC 4.2.1.40 (glucarate dehydratase), EC 4.2.1.67 (fuconate dehydratase), EC 4.2.1.82 (xylonate dehydratase), EC 4.2.1.90 (rhamnonate dehydratase) and dihydroxy acid dehydratases (4.2.1.9). Since known enzyme selectivity is the production of an alpha-keto acid the identified enzymes will produce DEHU and DTHU, respectively, as the reaction products Step 19: Conversion of 1,5-gluconolactone to guluronic acid lactone. This step can be performed by enzymes of the family of alditol oxidases (EC 1.1.3.41) or the enzymes described in Step 6. Examples of alditol oxidases that can be used for Step 19 include SEQ ID NOs 39-54 or a homolog of any of them, or by an alditol oxidase encoded by a nucleic acid of SEQ ID NOs: 47-54 or a homolog of any of them; and any one or any combination of them can be used to perform Step 19. Methods of Converting DDG to FDCA and of making esterified DDG and FDCA The present invention also provides novel methods of converting DDG to FDCA and FDCA esters. Esters of FDCA include diethyl esters, dibutyl esters, and other esters. The methods involve converting DDG into a DDG ester by contacting DDG with an alcohol, an inorganic acid, and optionally a co-solvent to produce a derivative of DDG. The alcohol can be methanol, ethanol, propanol, isopropanol, butanol, isobutanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, dimethyl sulfoxide, dimethylformamide, polyethylene glycol, methyl isobutyl ketone, or any C1-C20 alcohol. The inorganic acid can be sulfuric acid, phosphoric acid, perchloric acid, nitric acid, hydrochloric acid, hydrofluoric acid, hydroboromic acid and hydriodic acid. The co-solvent can be any of or any mixture of THF, acetone, acetonitrile, an ether, butyl acetate, an dioxane, chloroform, methylene chloride, 1,2-dichloroethane, a hexane, toluene, and a xylene. Any combination of the alcohols, inorganic acids, and co-solvents can be utilized in the reactions. The esterified DDG can then be converted into esterified FDCA, for example by contacting it with an acid catalyst.

DDG Purification

DDG purification for dehydration or esterification was performed by acidifying the DDG, e.g., by lowering the pH of the reaction with the addition of conc HCl to pH~2.5. At this pH proteins and any residual glucarate precipitate are removed by filtration and the mixture is lyophilized to give a white powder consisting of DDG and the reaction salts. The mixture can be lyophilized at neutral pH after the enzymes have been removed by filtration. Without further purification the DDG can then be dehydrated to give 2,5-FDCA, or be esterified to dibutyl-DDG (or di-ethyl DDG) prior to dehydration. One or more steps of purifying or esterifying DDG can be added to any of the methods and pathways disclosed herein that produce DDG. Other methods for purifying DDG from the aqueous mixture can also be used. These include separations using membranes or ion exchange resins that capture salts or DDG etc.

The invention therefore provides a method of purifying DDG that involves acidifying DDG in a solution, filtering the solution through a filter membrane, and removing water from the solution (e.g., by lyophilization ro spray drying). The solution with the DDG can be acidified to a pH of 2.5-3.5 or pH of 3.0-4.0 or pH of 3.5-4.5 or pH of 4.0-5.0 or pH of 4.5-5.5 or pH of 5.0-6.0 or pH of 5.5-6.5 or pH of 6.0-7.0 or pH of 6.5-7.5 or pH of 7.0-8.0 or pH of 7.5-8.5 or pH of about 8. The amount of water removed can be greater than 80% or greater than 85% or greater than 87% of the water or greater than 90% of the water or greater than 95% of the water or greater than 97% or greater than 98% or greater than 99% of the water from the solvent comprising the DDG. Yields of greater than 25% or 30% or 35% or 40% or 45% molar can be obtained. In one embodiment the method does not involve a step of ion exchange chromatography.

Methods for Synthesizing FDCA and FDCA Derivatives

The invention also provides various methods of synthesizing FDCA. One method for synthesizing FDCA involves contacting DDG with an alcohol, an inorganic acid at a high temperature to form FDCA. The alcohol can be any alcohol (e.g., any of those described above), and examples include (but are not limited to) methanol, ethanol, propanol, and butanol. Diols can also be used. The high temperature can be a temperature greater than 70° C. or greater than 80° C. or greater than 90° C. or greater than 100° C. or greater than 110° C. or greater than 120° C. or greater than 130° C. or greater than 140° C. or greater than 150° C. to form FDCA. Reaction yields of greater than 20% or greater than 30% or greater than 35% or greater than 40% can be achieved.

The invention also provides methods for synthesizing derivatives of FDCA. The methods involve contacting a derivative of DDG with an inorganic acid to produce a derivative of FDCA. The inorganic acid can be, for example, sulfuric acid, or any inorganic acid such as those described above. Optionally, the derivative of DDG can be purified prior to contacting it with the second inorganic acid. Nonlimiting examples of derivatives of DDG or FDCA include, but are not limited to, methyl DDG, ethyl DDG, propyl DDG, butyl DDG, isobutyl DDG, di-methyl DDG, di-ethyl DDG, di-propyl DDG, di-butyl DDG. The derivative of FDCA produced can be, but is not limited to, methyl FDCA, ethyl FDCA, propyl FDCA, butyl FDCA, di-methyl FDCA, di-ethyl FDCA, di-propyl FDCA, di-butyl FDCA, and isobutyl FDCA. The derivate of FDCA produced corresponds to the derivative of DDG used in the method. The derivative of FDCA can then be de-esterified to produce FDCA. The method can also be conducted in the gas phase, e.g., using the parameters described below.

Another method for synthesizing FDCA or derivatives of FDCA involves contacting DDG or derivatives of DDG (any described herein) with an inorganic acid in a gas phase, which can be done with a short residence time, e.g., of less than 10 seconds or less than 8 seconds, or less than 6 seconds or less than 5 seconds or less than 4 seconds or less than 3 seconds or less than 2 seconds or less than 1 second. The residence time refers to the time that the sample is present in the reaction zone of the high temperature flow through reactor. The method can also be conducted at high temperatures, for example at temperatures greater than 150° C., greater than 200° C., greater than 250° C., greater than 300° C. or greater than 350° C. Yields of greater than 25% or greater than 30% or greater than 40% or greater than 45% or greater than 50% molar are obtainable. Another method for synthesizing FDCA involves contacting DDG with an inorganic acid at a temperature in excess of 80° C. or 90° C. or 100° C. or 110° C. or 120° C. Another method for synthesizing FDCA involves contacting DDG with an inorganic acid under anhydrous reaction conditions. In various embodiments the anhydrous conditions can be established by lyophilizing the DDG in any method of synthesizing FDCA disclosed herein so that the DDG contains less than 10% or less than 9% or less than 8% or less than 7% or less than 6% or less than 5% or less than 4% or less than 3% water or less than 2% water, by weight.

The methods of the invention for synthesizing FDCA and its derivatives as described herein provide a significantly higher yield than has been available. In different embodiments molar yields of FDCA (v. DDG) can be obtained of greater than 10% or greater than 15% or greater than 20% or greater than 25% or greater than 30% or greater than 35% or greater than 40% or greater than 45% or greater than 50% or greater than 60% or greater than 65% or from about 40% to about 70%, or from about 45% to about 65%, or from about 50% to about 60%.

EXAMPLES

Example 1

Step 2, Gluconic Acid to 3-dehydro-gluconic acid (DHG)

Enzymes with natural activity for the dehydration of gluconate are useful in the invention (EC 4.2.1.39). Three enzymes from this family were cloned as shown in Table 1. Enzyme pSGI-365 was cloned and shown to be a dehydratase with broad substrate range having strong activity for the dehydration of gluconate (Kim, S. Lee, S. B. *Biotechnol. Bioprocess Eng.* 2008, 13, 436).

TABLE 1

Enzymes used in this experiment and identity homology. All expressed in *P. fluorescens*

| Organism | pSGI (Vector) | Gene ID | WT/ SYN | Expression Host |
|---|---|---|---|---|
| *Achromobacter* | 365 (pRANGER) | E3HJU7 | Syn | *P. fluorescens* |
| *Achromobacter* | 359 (pRANGER) | #0385 | wt | *P. fluorescens* |
| *Acinetobacter* | 360 (pRANGER) | #0336 | wt | *P. fluorescens* |

| | 359_Achromob | 365_E3HJU7 |
|---|---|---|
| pSGI-360_Acinetobacter (SGI) | 78 | 79 |
| pSGI-359_Achromobacter (SGI) | | 95 |
| pSGI-365 *Acromobacter* | | |

Figure 4:
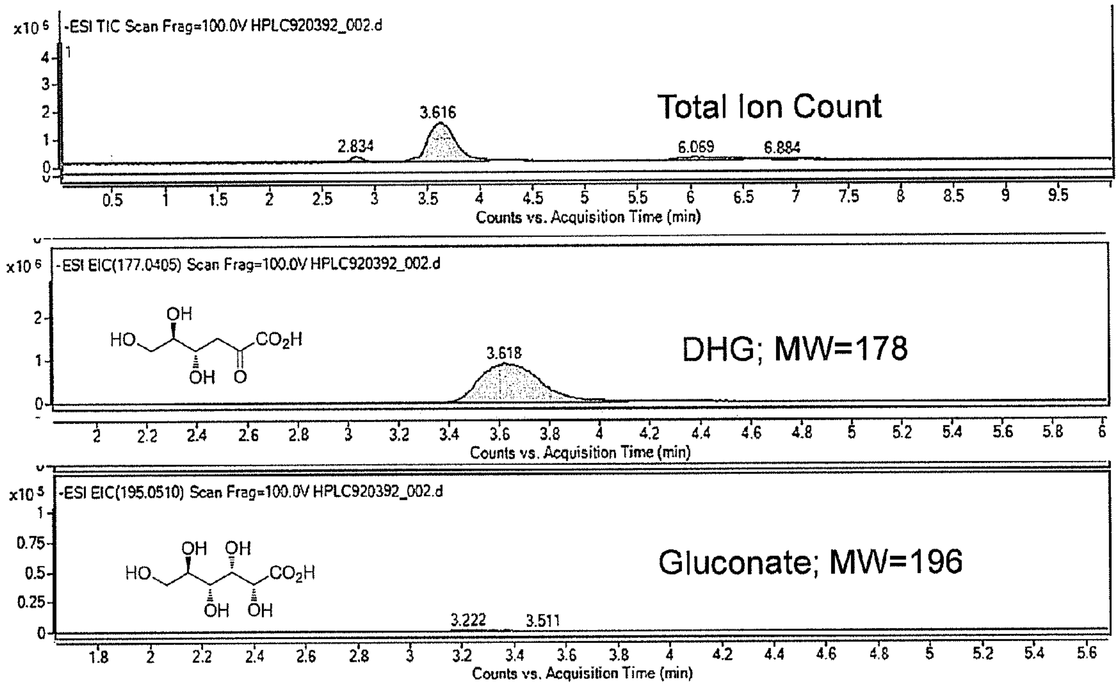
FIG. 4 is an HPCL-MS analysis of the dehydration of gluconate with gluconate dehydratase to produce DHG by pSGI-359.
Figure 5:
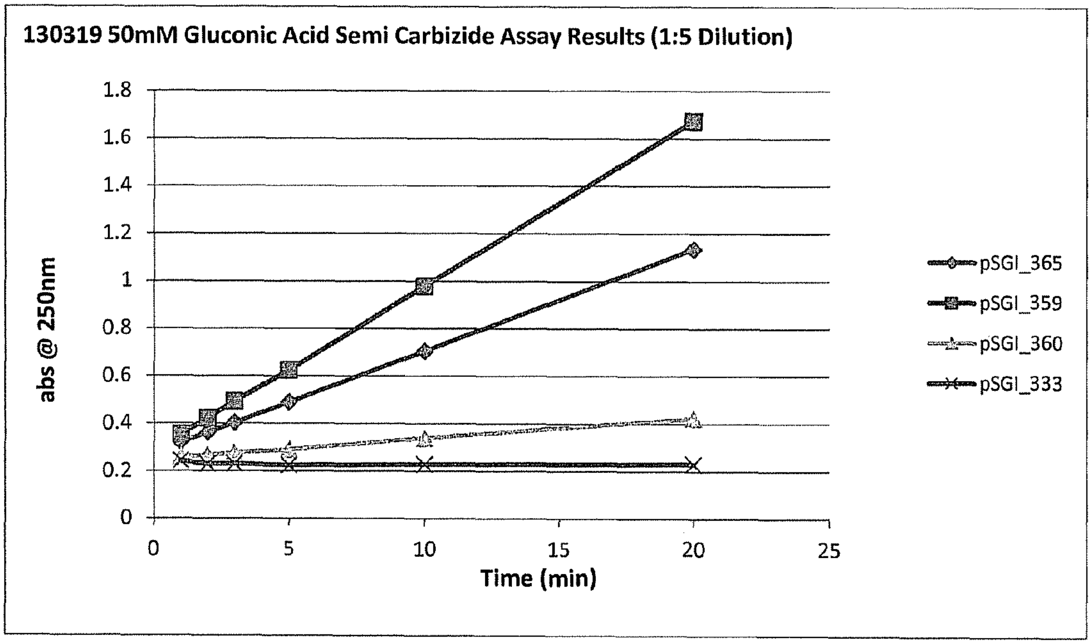
FIG. 5 is a graphical illustration of semicarbizide assay plots for measuring the activity of gluconate dehydratases.

Proteins 359, 360, and 365 (SEQ ID NOs 33-35, respectively) showed 2-5 mmole/min per mg of crude enzyme lysate activity for the synthesis of dehydration of gluconate (gel not shown). pSGI-359 was isolated by precipitation with ammonium sulfate and re-dissolving in buffer and assayed by the semicarbazide assay. Activities of 46.2 U/mL or 5.3 U/mg (1 unit=μmole/min) for the dehydration of gluconate were calculated from semicarbazide assay plots. Reaction buffer (93 mL) containing Kpi 10 mM pH 8.0 with 2 mM MgCl2 and 3.5 gr (0.016 mole) of sodium gluconate was mixed with 7 mL of the previous gluconate dehydratase solution. The reaction was incubated at 45° C. for 16 h before one aliquot was analyzed by HPLC-MS (FIG. 4). As shown in FIG. 4 one new major product with the molecular weight of DHG was produced. The product was also shown to have activity with DHG dehydratases.

All proteins were cloned on the pRANGER™ (Lucigen, Middleton, Wis.) expression vector and were expressed in a *Pseudomonas fluorecens* strain. pRANGER™ is a broad host commercially available plasmid vector containing the pBBR1 replicon, Kanamycin resistance and an pBAD promoter for inducible expression of genes. For the enzyme assay a modification of the semicarbazide assay for the quantification of alpha keto acid was used to calculate the activity of each enzyme (Kim, S.; Lee, S. B. *Biochem J.* 2005, 387, 271). SEQ ID NOs: 30-32 and 33-35 show the amino acid and nucleotide sequences, respectively, of the gluconate dehydratases #0385, #0336, and E3HJU7.

Example 2

Step 3—3-dehydro-gluconic acid (DHG) to (4S)-4,6-dihydroxy 2,5-diketo hexanoate (2,5-DDH)

Enzymes of the family (EC 1.1.1.127) can be used to perform this step. Two examples are 2-dehydro-3-deoxy-D-gluconate 5-dehydrogenase and DHG dehydrogenases. Five enzymes from this family were cloned as shown in Table 2 below. pRANGER™ vector was used in every case.

TABLE 2

Cloned of DHG oxidoreductase (or 2-dehydro-3-deoxy-D-gluconate 5-dehydrogenase)

| Organism | pSGI (Vector) | Gene ID | WT/SYN | Expression Host |
|---|---|---|---|---|
| *Agrobacterium* sp (SGI) | 374 | #9041 | WT | *P. fluorescens* |

TABLE 2-continued

| Cloned of DHG oxidoreductase (or 2-dehydro-3-deoxy-D-gluconate 5-dehydrogenase) | | | | |
|---|---|---|---|---|
| Organism | pSGI (Vector) | Gene ID | WT/SYN | Expression Host |
| *Agrobacterium tumefaciens* (SGI) | 375 | #8939 | WT | *P. fluorescens* |
| *E. coli* | 376 | P37769 | WT | *P. fluorescens* |
| *Sphingomonas* (SGI) | 395 | #5112 | WT | *P. fluorescens* |
| *Hoeflea phototrophica* (SGI) | 396 | #7103 | WT | *P. fluorescens* |

The product prepared from the dehydration of gluconate in Step 2 was used as substrate for assaying the lysates of Table 2. As shown in the following Table 3, enzymes were identified showing activity for the oxidation of DHG in assays measuring NADH formation (absorbance increase at 340 nm).

TABLE 3

| Activity calculations for oxidation of DHG to 2,5-DDH using DHG oxidoreductase. A unit = μmole/min of NADH | | | |
|---|---|---|---|
| | U/mg (100 mM DHG) | | |
| ENZ | pH = 7.5 | pH = 8.5 (10 mM DHG) | pH = 9.5 |
| pSGI_395 | 0.012 | 0.070 (0.02) | 0.120 |
| pSGI_396 | 0.033 | 0.139 (0.018) | 0.418 |
| pSGI_374 | 0.007 | 0.043 (0.012) | 0.091 |
| pSGI_376 | 0.007 | 0.121 (0.01) | 1.610 |

Further verification of the formation of 2,5-DDH by these enzymes was shown in Step 16 where the reduction of 2,5-DDH (made from the dehydration of 5KGA) with pSGI-395 at acidic pH was shown.

Example 3

Steps 7 and 7B—Conversion of Guluronic Acid to D-Glucaric Acid (7) and Conversion of L-Iduronic Acid to Idaric Acid (7B)

To demonstrate Steps 7 and 7B the following study was performed. Uronate dehydrogenases (EC 1.1.1.203) are enzymes that oxidize glucuronic and galacturonic acid. Three enzymes with sequence similarity to the known uronate dehydrogenase (Expasy: Q7CRQ0; Prather, K. J, et al., *J. Bacteriol.* 2009, 191, 1565) were cloned from bacterial strains as shown in Tables 4 & 5.

TABLE 4

| Cloned Uronate Dehydrogenases | | | |
|---|---|---|---|
| Organism | pSGI (pET28) | Gene ID | Expression |
| *Agrobacterium* | #474 | #8807 | BL21DE3 |
| *Rhizobium* | #475 | #8958 | BL21DE3 |
| *Pseudomonas* | #476 | #1770 | BL21DE3 |

TABLE 5

| Sequence Identity | | | |
|---|---|---|---|
| | #475 | #476 | Q7CRQ0 |
| 474_Agrobacterium | 73 | 49 | 90 |
| 475_Rhizobium | | 51 | 74 |
| 476_Pseudomonas | | | 50 |

Each protein was expressed with a His tag from pET28 and was purified prior to their screening. Protein gels of the crude lysates and purified enzymes are shown in the gel of FIG. 1. After purification all enzymes were tested for activity against glucuronate, as well as against guluronate and iduronate. Kinetic measurements at different substrate concentrations were performed and the calculated activities and Km values for each enzyme are shown in Table 6. All enzymes showed good activity for glucuronate, and also for L-iduronate and guluronate.

TABLE 6

| Activity and Km value for purified uronate dehydrogenases. | | | |
|---|---|---|---|
| | Vmax (μM/min/mg); and Km (mM) | | |
| Enzyme | Glucuronate | Iduronate | Guluronate (Vm only) |
| 474 | 128.2; 0.37 | 0.96; 29.8 | 0.017 |
| 475 | 47.4; 0.22 | 0.59; 42.1 | 0.016 |
| 476 | 90.9; 0.34 | 1.36; 29.6 | 0.014 |

Figure 6A:
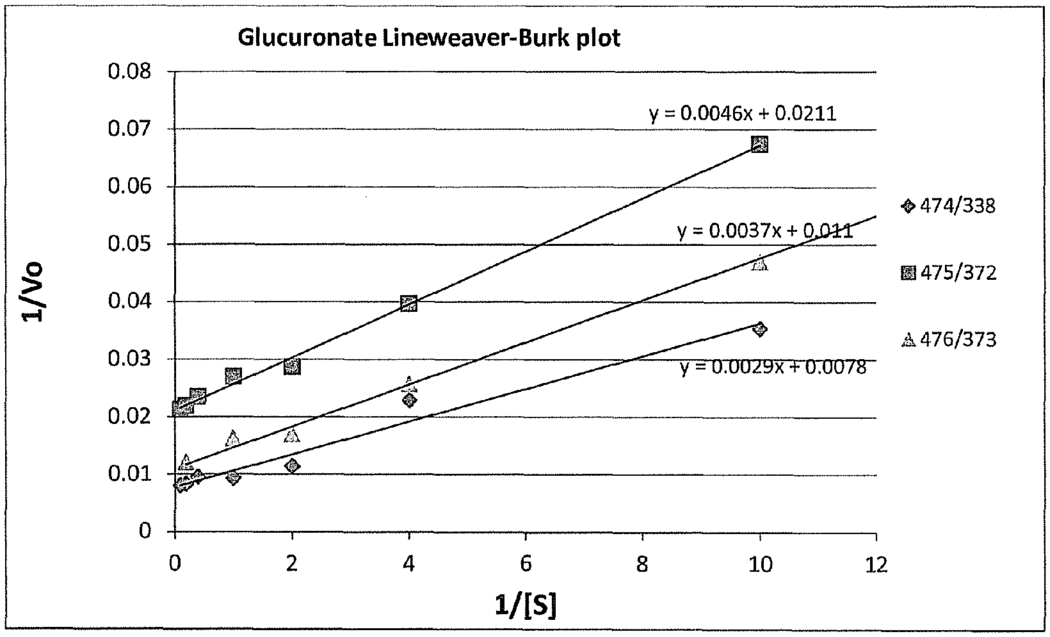
FIGS. 6*a*-6*b* provide Lineweaver-Burk plots for the oxidation of glucuronate and iduronate with three enzymes of the invention.
Figure 6B:
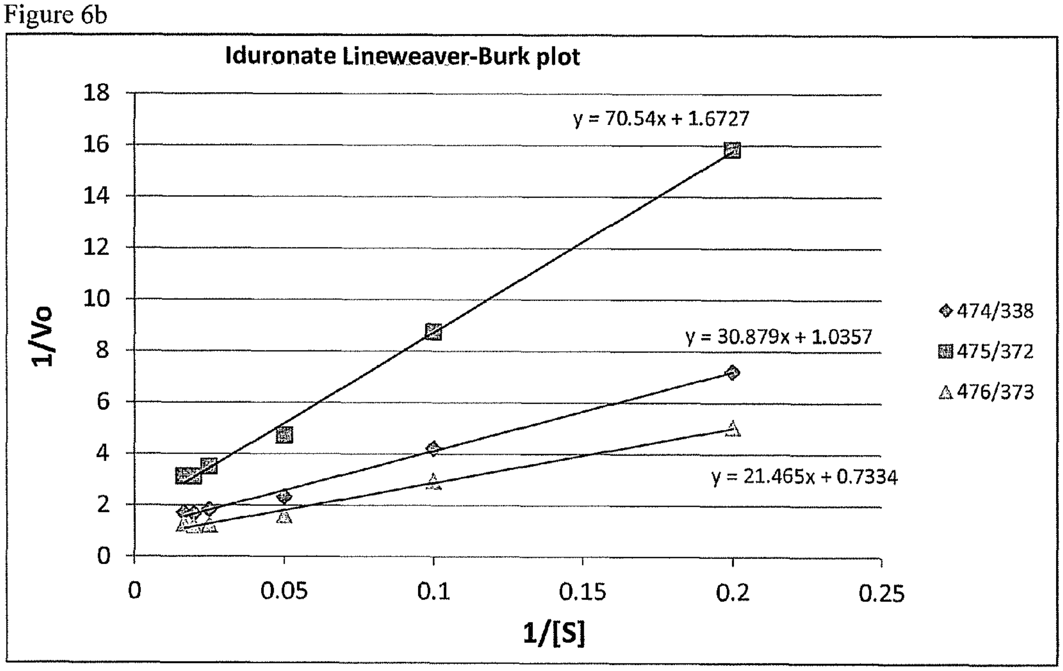

Each plasmid shown in Table 4 was transformed in BL21DE3 *E. coli* cells. Clarified lysates were mixed with equal volume of (25 mL) of equilibration buffer and purified on an Ni NTA column. Activity of each purified enzyme was measured in by mixing 0.050 mL of various dilutions of each purified enzyme with 0.95 mL of reaction buffer (100 mM TrisHCl, pH 8.0, 50 mM NaCl, 0.75 mM NAD+). The reaction progress was measured by monitoring of the formation of NADH at 340 nm. FIGS. 6*a* and 6*b* provide Lineweaver-Burk plots for the oxidation of glucuronate and iduronate, with all three enzymes shown in FIG. 6. Clear positive slopes were obtained with all enzymes giving the activities shown in the table above. Protein sequences of the uronate dehydrogenases are shown as SEQ ID NOs: 1-3 and the genes as SEQ ID NO: 4-6.

Pyrroloquinoline (PQQ) dependent aldehyde dehydrogenases also showed good activity for the oxidation of both guluronate and iduronate. These are soluble periplasmic enzymes that were expressed in the *E. coli* cytosol after their periplasmic target sequence was removed. The activities of crude lysates in units (μmole/min) per milligram of total lysate protein are shown in the following Table 6A. The actual activity of each enzyme is at least 2-5× higher if purified (see expression in FIG. 3).

| Enzyme | Iduronate U/mg | Guluronate U/mg |
|---|---|---|
| P75804 (SEQ ID NO: 73) | 8.7 | 3.2 |
| 9522 (SEQ ID NO: 74) | 7.3 | 6.1 |
| 6926 (SEQ ID NO: 75) | 9.2 | 4.1 |

-continued

| Enzyme | Iduronate U/mg | Guluronate U/mg |
|---|---|---|
| 7510 (SEQ ID NO: 76) | 7.3 | 3.7 |
| 7215 (SEQ ID NO: 77) | 14.2 | 8.3 |
| 8386 (SEQ ID NO: 78) | 4.3 | 1.5 |

The activities shown on Table 6A were measured using an artificial electron acceptor DCPIP (2,6-dichloroindophenol) according to the following protocol: In 0.95 mL of 20 mM Triethanol amine (pH 8.0) containing 0.2 mM DCPIP, 0.2 mM PMS (phnazine ethosulfate) and substrate (10-40 mM), 0.050 mL of enzyme (as crude lysate or 10-100× diluted with buffer) is added and the reaction progress is followed by the change of DCPIP absorbance at 600 nm. Because in their natural state these enzymes are transferring electrons to other proteins or cofactors in the membrane electron transport chain, the in vitro activity is measured using artificial electron acceptors with DCPIP being the most common.

TABLE 7

| Isomerases cloned | | | | |
|---|---|---|---|---|
| EC | Organism | pSGI (pET28) | Gene ID Archetype ® or Expasy | WT/SYN |
| 5.3.1.17 | *Rhizobium* | 433 | #8938 | WT |
| 5.3.1.17 | *E. coli* | 434 | Q46938 (Expasy) | WT |
| 5.3.1.17 | *Rhizobium* | 435 | #3891 | WT |
| 5.3.1.17 | *Pannonibacter* | 436 | #7102 | WT |
| 5.3.1.n1 | *Lactobacillus* | 458 | A5YBJ4 (Expasy) | SYN |
| 5.3.1.n1 | *Acidophilum* | 440 | F0J748 (Expasy) | SYN |
| 5.3.1.n1 | *Bacillus* | 437 | #9209 | WT |
| 5.3.1.n1 | *Ochrobactrum* | 438 | #9732 | WT |
| 5.3.1.n1 | *Halomonas* | 439 | #7403 | WT |
| 5.3.1.12 | *Sphingobacteria* | 478 | #1874 | WT |
| 5.3.1.12 | *Thermotoga* | 479 | Q9WXR9 | SYN |
| 5.3.1.12 | *Bacillus* | 480 | Q9KFI6 | SYN |
| 5.3.1.12 | *Bacillus* | 481 | O34808 | SYN |

TABLE 8

| % Identities of isomerases | | | | | | | | | | | | | |
|---|---|---|---|---|---|---|---|---|---|---|---|---|---|
| | EC | 436 | 434 | 435 | 458 | 440 | 437 | 438 | 439 | 481 | 480 | 479 | 478 |
| 433 | 5.3.1.17 | 65 | 44 | 43 | 16 | 13 | 18 | 11 | 14 | 6 | 11 | 11 | 7 |
| 436 | 5.3.1.17 | | 45 | 46 | 18 | 14 | 15 | 12 | 13 | 5 | 10 | 11 | 7 |
| 434 | 5.3.1.17 | | | 46 | 17 | 10 | 15 | 10 | 13 | 6 | 10 | 12 | 7 |
| 435 | 5.3.1.17 | | | | 18 | 16 | 18 | 14 | 16 | 9 | 11 | 13 | 7 |
| 458 | 5.3.1.n1 | | | | | 37 | 57 | 41 | 44 | 6 | 7 | 9 | 5 |
| 440 | 5.3.1.n1 | | | | | | 40 | 67 | 50 | 6 | 6 | 6 | 5 |
| 437 | 5.3.1.n1 | | | | | | | 46 | 51 | 8 | 7 | 10 | 6 |
| 438 | 5.3.1.n1 | | | | | | | | 52 | 5 | 5 | 6 | 4 |
| 439 | 5.3.1.n1 | | | | | | | | | 6 | 7 | 8 | 5 |
| 481 | 5.3.1.12 | | | | | | | | | | 7 | 36 | 54 |
| 480 | 5.3.1.12 | | | | | | | | | | | 7 | 7 |
| 479 | 5.3.1.12 | | | | | | | | | | | | 37 |
| 478 | 5.3.1.12 | | | | | | | | | | | | |

The enzymes on Table 6A were active against a number of other aldehydes including butyraldehyde, butyraldehyde and glycerol (but not glucose). Therefore, these enzymes will oxidize the aldehyde group of iduronate and guluronate to give iduronic and glucaric acid respectively. In order to confirm this selectivity, two of these enzymes, #403 and #412, were expressed in the periplasm of *E. coli* by fusing them with the periplasmic target sequence of #403 (a native *E. coli* enzyme). Both proteins were expressed in the periplasm but in lower levels compared to the cytosol. The previous recombinant cells oxidized benzaldehyde to benzoic acid in good yields and in lower yields produced glucaric and idaric acid from guluronate and iduronate.

Example 4

Step-15: Conversion of 5-Ketogluconate (5-KGA) to L-Iduronic Acid (15) or Guluronic Acid (15A)

This example illustrates the identification of an enzyme capable of isomerizing 5-KGA to iduronic acid (Step 15) or guluronic acid (Step 15A). Thirteen enzymes from three different isomerase families were cloned as shown in Table 7, while their % sequence identity is shown in Table 8.

As shown in Table 8, enzymes with medium homology (underlined) within each family were selected for cloning. The data demonstrated that enzymes from all families showed activity for the isomerization of 5-KGA giving L-iduronate as the main product. Two enzymes from the 5.3.1A7 family (433 & 434) were also used in the example showing the formation of DDG from 5-ketogluconate (5KGA).

Activity for the isomerization of 5KGA and iduronate using enzymes from Table 7 was measured using an enzymatic method that detected the formation of products by their activity against two different enzymes. For example, isomerization of 5KGA was detected by measuring the activity of the product iduronate using uronate dehydrogenase (pSGI-476). Isomerization of iduronate was detected by measuring the activity 5KGA reductase (pSGI-383, EC 1.1.1.69) of the product 5KGA. Presence of the products was also detected by GC-MS.

Figure 7A:
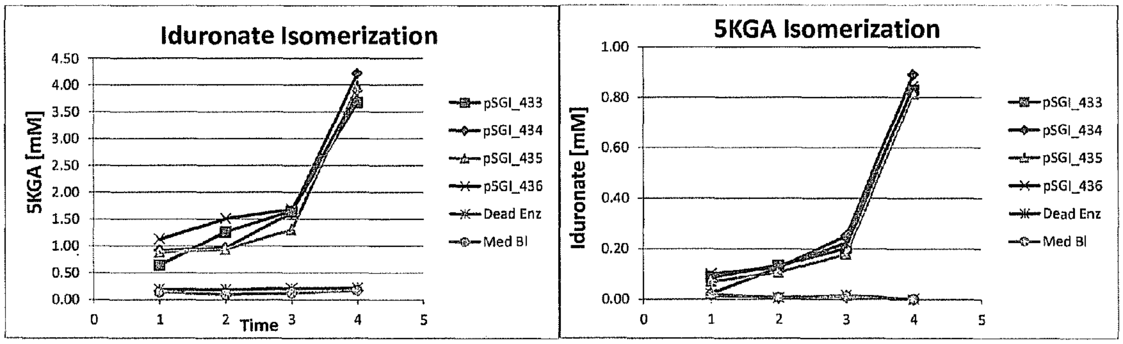
FIG. 7*a* shows the results of an HPLC analysis of time points for the isomerization of 5KGA and Iduronate using enzymes DTHU isomerases in the EC 5.3.1.17 family. Controls: dead enzyme is a control with heat inactivated enzyme. Med Bl refers to reactions without isomerase add/n. Time points, x axis 1=0.5 h; 2=1; 3=2 h; 4=16 h.

Enzymes from all families showed varying activity for the isomerization of 5KGA and iduronate. Two enzymes from EC 5.3.1.12 were used in a cell free reaction to isomerize 5KGA and ultimately produce DDG as described in the example. The enzymes were purified and showed a single band by gel electrophoresis. The purified isomerases were used in reactions using lysate and buffer containing 5KGA or Iduronate. Product formation was demonstrating using both HPLC and the previously described enzymatic methods. Results for 17 h of incubation using both HPLC and enzyme assays are shown in FIG. 7*a*. All enzymes showed good activity for the isomerization of both 5KGA and iduronate. Yields for iduronate isomerization by pSGI433, pSGI 434, pSGI 435, and p SGI 436 were 56%, 48% 42%, (436 not measured), respectively when measured enzymatically and 78.8%, 78.5%, 73.3% and 76.6%, respectively when measured by HPLC assay. Yields after 16 h for 5KGA isomerization by the same enzymes were 18%, 17%, and 19% respectively (436 not measured) when measured by enzymatic assay, and 16.6%, 17.8%, 16.3%, and 16.9%, respectively, when measured by HPLC assay.

EC 5.3.1.12 Enzymes

Figure 7B:
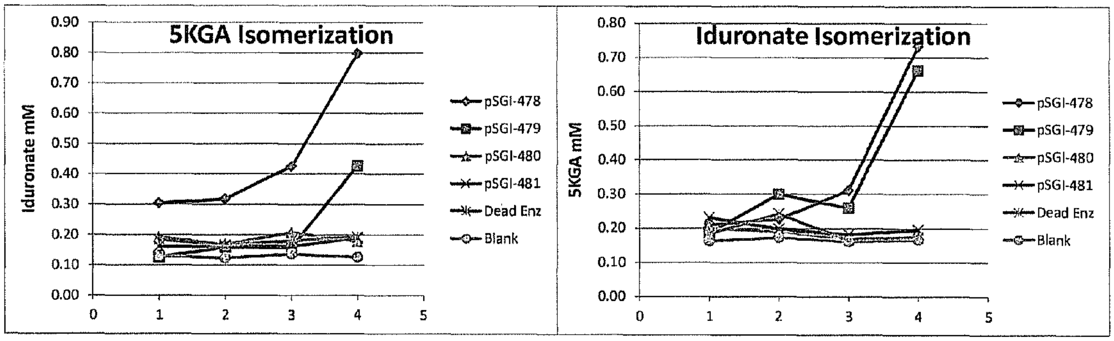
FIG. 7*b* shows an HPLC analysis of time points for the isomerization of 5KGA and iduronate using enzymes in the EC 5.3.1.17 family. Controls: dead enzyme is a control with heat inactivated enzyme; Med Bl: refers to reactions without isomerase add/n. Time points, X axis: 1=0 h; 2=1 h; 3=2 h; 4=17 h.

Enzymes from the EC 5.3.1.12 family (glucuronate isomerases) were also purified by gel electrophoresis, isolated, and used to prepare reactions by mixing with buffer (50 mM HEPES, 1 mM ZnCl2, pH 8.0) that contained 5 mM of 5KGA or Iduronate. The reactions were incubated at 30° C. and analyzed for product formation using both HPLC and enzymatic methods. Results are shown in FIG. 7*b*.

5.3.1.17 Enzymes

Enzymes pSGI-478 and pSGI-479 (5-dehydro-4-deoxy-D-glucuronate isomerases) showed isomerization activity for both 5KGA and iduronate. This activity was also confirmed with the enzymatic assays as above. Yields for isomerization of iduronate by pSGI-478 and -479 were 50% and 37%, respectively, when measured enzymatically, and 20% and 18% when measured by HPLC. Yields for 5KGA isomerization were 23% and 26%, respectively, when measured enzymatically, and 24% and 16%, respectively when measured by HPLC. Results are shown in FIG. 7*a*.

5.3.1.n1 Enzymes

Figure 8:
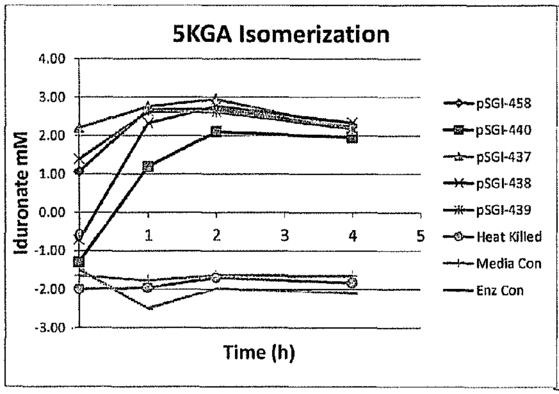
FIG. 8 shows product formation for the isomerization of 5KGA and iduronate with enzymes in the EC 5.3.1.n1 family. The data were obtained from enzymatic assays.
Figure 8:
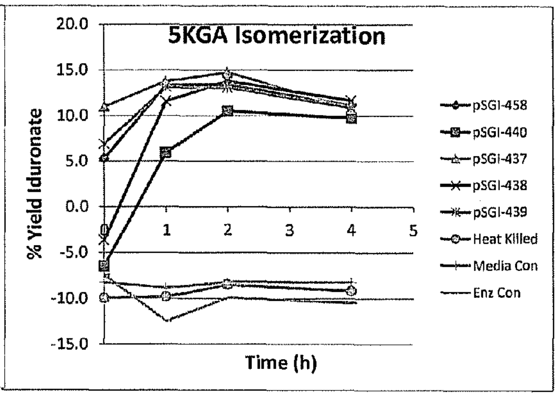

Enzymes in this family were purified by gel electrophoresis. Product formation was measured using enzymatic assays as described above and the results are shown in FIG. 8. All enzymes cloned in this family were shown to have activity for the isomerization of 5KGA and iduronate.

In each case plasmids were transformed in BL21DE3 and proteins purified on a Ni NTA column.

Example 5

Step 16—5-Keto-Gluconate (5KGA) to (4S)-4,6-Dihydroxy 2,5-Diketo Hexanoate (2,5-DDH)

Figure 9:
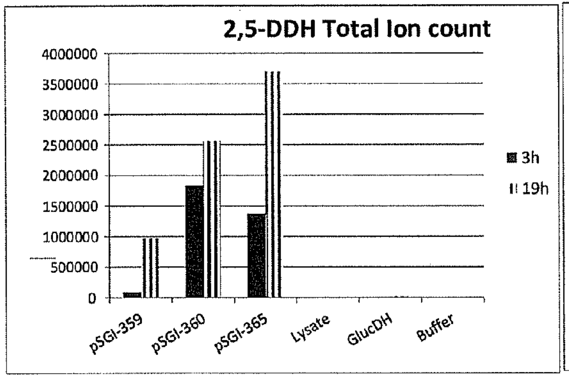
FIG. 9: HPLC analysis of the formation of 2,5-DDH and the reduction of 5KGA concentration over time. Total ion counts for 2,5-DDH are shown.
Figure 9:
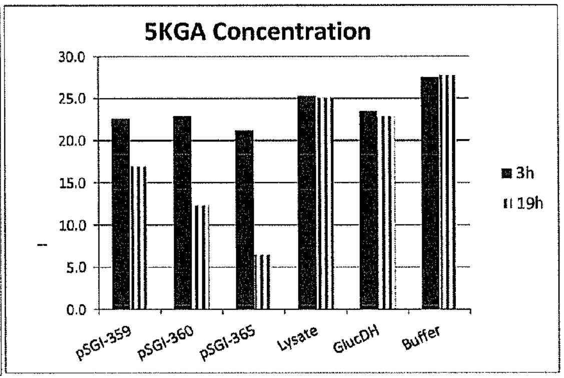

The three gluconate dehydratases described in Step 2 (Example 1) were expressed as described in Example 1, along with a purified glucarate dehydratase from Step 8. Enzymatic reactions for activity were performed and HPLC-MS analysis showed the formation of 2,5-DDH (FIG. 9), which was also confirmed by the fact that formation of the new product was accompanied by the reduction of 5-KGA only in the samples containing gluconate dehydratases, as well as by enzymatic assays with DHG dehydratase (pSGI-395). Good slopes at 340 nm indicating large enzyme activity were obtained when NADH, pSGI-395 lysate and aliquots of the previous reactions were mixed (data not shown). This result in combination with the HPLC analysis prove that the gluconate dehydratases examined dehydrate 5KGA to 2,5-DDH.

Example 6

Step 19—Conversion of 1,5-Gluconolactone to Guluronic Acid δ-Lactone 1,5-gluconolactone oxidation is a side activity of enzymes from the alditol oxidases (EC 1.1.3.41) family. These enzymes oxidize various alditols such as sorbitol, xylitol, glycerol and others. Enzymes were identified having activity for the oxidation of 1,5-gluconolacone, as shown in Table 6 below.

TABLE 6

Alditol oxidases with activity on 1,5-gluconolactone.

| | | | 1,5-Gluconolactone | | | |
|---|---|---|---|---|---|---|
| | | | | Reaction Setup | | |
| Enzyme | Enzyme Source | Sorbitol U/mg | U/mg | Enzyme mg | Substrate mg/mM | Yield |
| AO#13 | *Terriglobuds roseus* | 0.23 | 0.02 | 5.3 | 15/85 | 7% |
| AO#22 | *Granulicella mallensis* | 0.27 | 0.015 | 7.6 | 15/85 | 9% |
| AO#28 | *Streptomyces acidiscabies* | 1.30 | 0.010 | 15 | 15/85 | 8% |
| AO#36 | *Actinomycetales* (SGI) | 1.83 | 0.102 | 25 | 90/35 | 46% |
| AO#51 | *Frankia* sp | 0.59 | 0.019 | NT | NT | NT |
| AO#57 | Propionibacteriacaeae (SGI) | 1.47 | 0.051 | 40 | 70/57 | 6% |
| AO#76 | *Streptomyces* sp. | 1.45 | 0.045 | 8.2 | 15/85 | 23% |
| AO#251* | *Paenibacillus* sp. | 0.47 | 0.003 | 24 | 15 8.5 | ~2% |

*crude lysate

Figure 10:
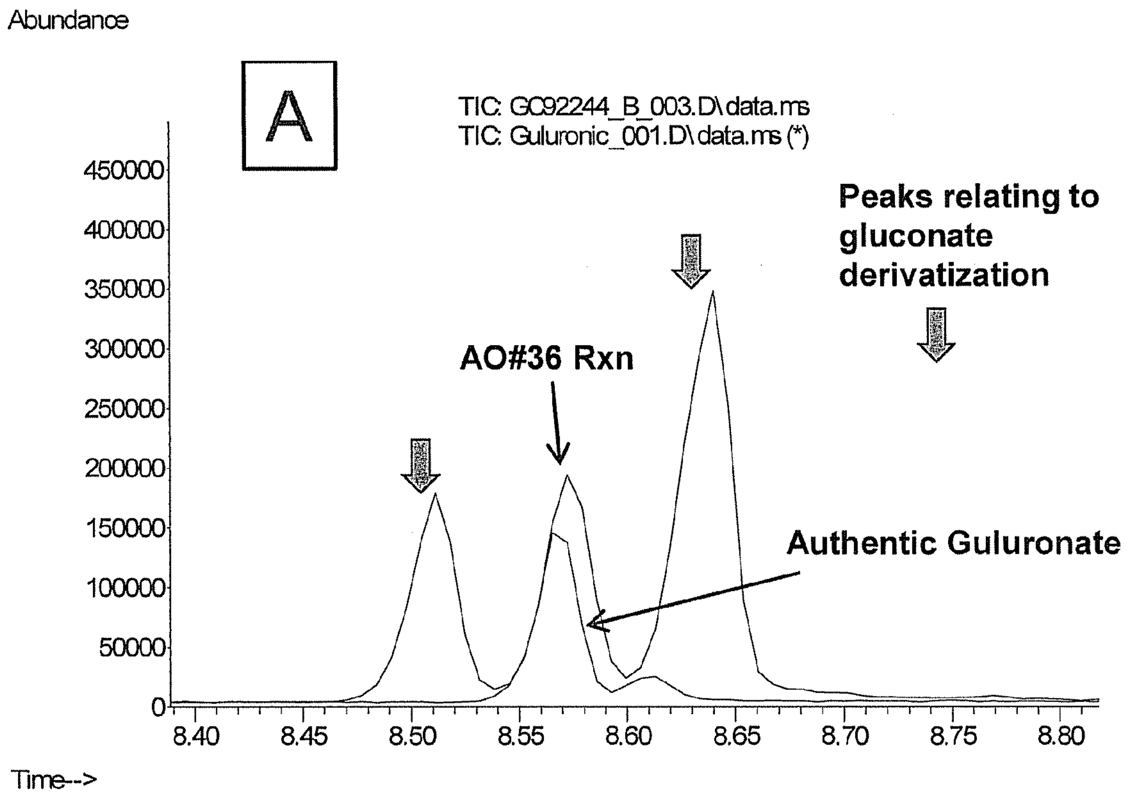
FIG. 10 is a HPLC-MS chromatogram showing the production of guluronic acid lactone from 1,5-gluconolactone. An overlay of a trace of authentic guluronic acid is shown.

Reactions were prepared using lysates of all the purified enzymes shown on Table 6. Reactions were prepared in 50 mM K-phosphate buffer, pH 7.0 with 0.5 mg/mL catalase and incubated at 30° C. A new product was observed by HPLC-MS analysis showing the same retention time as guluronate after comparison with authentic standards (FIG. 10). This was confirmed by GC-MS, where the product also had the same MS fingerprint as guluronate. It is therefore clear that all the alditol oxidases described in the Table oxidize the 6-OH of 1,5-gluconolactone to produce the guluronic acid lactone. All alditol oxidases were cloned in pET28a with a HisTag and were expressed in BL21DE3 and purified on a Ni NTA column.

Example 7

Synthesis of FDCA and Other Intermediates

Purified DDG mono potassium salt was used for the dehydration to 2,5-FDCA. Sulfuric acid was added to DDG and the reaction stirred at 60° C. The in situ yield was calculated (by HPLC-MS) to be ~24% and ~27%.

The reaction solutions were combined and then diluted by pouring into ice (to neutralize the heat). Approximately equivalent volume of THF was added, and the solution transferred to a separation funnel. Sodium chloride salt was added until separation was achieved. The solution was agitated between additions for best possible dissolution. The aqueous layer was removed, and the THF layer washed 3× more with sat. NaCL solution. Sodium sulfate was added and the solution left sitting overnight. Two layers formed again overnight. The aqueous layer was discarded and then silica gel was added to the solution. It was then concentrated down to solids via rotovap. The solids were loaded into a silica flash column and then separated via chromatographically. The fraction was concentrated and dried. The isolated yield was 173.9 mg. Corrected yield: 24.9%. $^{1}H$ and $^{13}C$ NMR and HPLC-MS analysis confirmed the product Dehydration of DDG Dibutyl-2,5-FDCA in BuOH/$H_2SO_4$ Dehydration of un-derivitized lyophilized DDG containing the dehydration salts in BuOH was done using a Dean-Stark apparatus. Under these conditions, DDG was added to BuOH, and then H2SO4 was added and the reaction heated at 140° C. After stirring for 4 h HPLC-MS analysis shows the disappearance of DDG and the formation of dibutyl-2,5-FDCA. The in situ yield was calculated (by HPLC-MS) to be 36.5%.

The mixture was extracted with water, 1% NaOH, and again with water. Then the organic layer was concentrated to a final mass of 37.21 g. A portion of this mass (3.4423 g) was removed and 0.34 g of dibutyl-2,5-FDCA was purified using HPLC. Extrapolating the yield of the isolated product to the total amount of compound isolated from the reaction (37.21 g) and taking into account the amount of salts present in the original DDG (~60% pure by weight) the reaction yield was calculated to be 42%. $^{1}H$ and $^{13}C$ NMR and HPLC-MS analysis confirmed the product Synthesis of Dibutyl DDG In another aspect the invention provides a method for synthesizing a derivative of DDG. The method involves contacting DDG with an alcohol, an inorganic acid, and optionally a co-solvent to produce a derivative of DDG. Optionally the derivative of DDG can be purified. The reaction can have a yield of the derivative of DDG of at least 10% molar yield or at least 15% molar yield or at least 20% molar yield or at least 25% or at least 30% or at least 35% molar yield or at least 40% molar yield. The inorganic acid can be sulfuric acid and the alcohol can be methanol, ethanol, propanol, butanol, isobutanol, or any C1-C20 alcohol. In various embodiments the co-solvent can be any of THF, acetone, acetonitrile, an ether, butyl acetate, an dioxane, chloroform, methylene chloride, 1,2-dichloroethane, a hexane, toluene, and a xylene. When the alcohol is ethanol the DDG derivative will be DDG mono-ethyl ester and/or DDG diethyl ester. When the alcohol is butanol the DDG derivative will be DDG mono-butyl ester and/or DDG dibutyl ester.

DDG mono-potassium salt was used for derivatization according to the following protocol. In a 1 L Morton type indented reaction vessel equipped with a mechanical stirrer and heating mantle was charged with 60:40 DDG:KCl (31.2 mmol), BuOH, and heptane. In a separate vial, sulfuric acid was added to water, and allowed to cool after dissolution. The solution was then added to the flask. The solution was kept at 30° C.

The precipitate was filtered off concentrated. The remaining gel was dissolved in EtOAc, and then TLC plates were spotted with the solutions and the plates were sprayed with a phosphomolybdic acid mixture, and then heated to at least 150° C. on a hot plate to identify the DDG-DBE fraction. Isolated yield: 4.62 g (15.2 mmol, 47% yield), >98% purity. $^{1}E1$ and $^{13}C$ NMR and HPLC-MS analysis confirmed the product.

Different solvents can be used in the synthesis of DDG esters, such as mixtures of BuOH (5%-95% v/v) with co-solvents such as THF, acetone, acetonitrile, ethers (dibutyl, diethyl etc), esters such as Butyl-acetate, 1,6-dioxane, chloroform, methylene chloride, 1,2-dichloroethane, hexanes, toluene, and xylenes may be used as cosolvents. Reaction catalysts such as acids (sulfuric, hydrochloric, polyphosphoric or immobilized acids such as DOWEX) or bases (pyridine, ethyl-amine, diethyl-amine, boron trifluoride) or other catalysts commonly used for the esterification of carboxylic acids.

Dehydration of Dibutyl-DDG to Dibutyl-FDCA in n-BuOH/$H_2SO_4$

A stock solution of DDG-DBE (di-butyl ester) was made in butanol and transferred to a clean, dry 100 mL round-bottomed flask equipped with a stir bar. To the flask, 25 mL of conc. sulfuric acid was added. The flask was sealed and then stirred at 60° C. for 2 hrs. The in situ yield was calculated to be ~56%. The reaction solution was concentrated and the residue was dissolved in MTBE and transferred to a separation funnel, and then washed with water. The recovered organic layer was concentrated and then separated via HPLC for an isolated yield: 250.7 mg (~90% purity) and 35% isolated yield (corrected for purity). $^{1}C$ and $^{13}C$ NMR and HPLC-MS analysis confirmed the product.

Example 8

Cell Free Synthesis of DDG and FDCA and Derivatives from 5-KGA (Route 2A)

This example illustrates the enzymatic conversion of 5KGA to DDG using purified enzymes according to Scheme 6 (a sub-Scheme of 2B), and also illustrates the DDG produced being dehydrated to FDCA using chemical steps. The Scheme involves the steps of isomerization of 5KGA (Step 15) and the subsequent oxidation to idaric acid (Step 7B). DDG was also dehydrated under differing chemical conditions to FDCA. The last step (Step-8A) was performed using glucarate dehydratase from *E. coli.*

Figure 11:
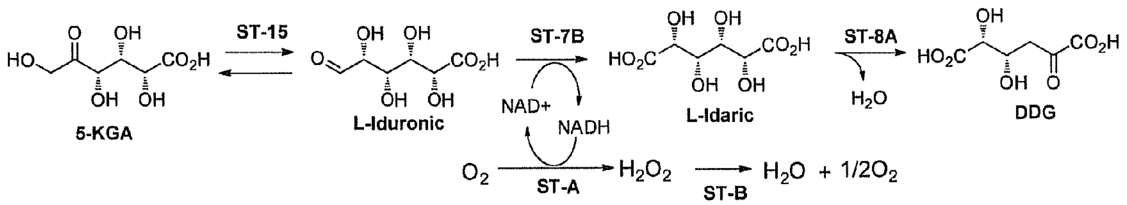
FIG. 11 is a schematic illustration of the Scheme 6 reaction pathway.

Scheme 6 is illustrated in FIG. 11. The scheme was performed using a cell free enzymatic synthesis of DDG from 5-KGA. The Scheme involves the performance of steps 15, 7B and 8A (see FIG. 2*d*). Two additional proteins were used to complete the reaction path, the first being NADH-oxidase (Step A) that is recycling the NAD+ cofactor in the presence of oxygen, and catalase (Step B) that decomposes the peroxide produced from the action of NADH oxidase. The enzymes are shown in the following Table 7. All enzymes contained a HisTag and were purified using an Ni-NTA column. Yields for this synthesis of DDG were calculated to be at least 88-97%.

TABLE 7

| STEP | Enzyme | EC | Organism |
|---|---|---|---|
| 15 | pSGI-433 (DTHU_IS) | 5.3.1.17 | *Rhizobium* (SGI) |
| 15 | pSGI-434 (DTHU_IS) | 5.3.1.17 | *E. coli* |
| 7B | pSGI-476 (UroDH) | 1.1.1.203 | *Pseudomonas* (SGI) |
| 8A | pSGI-353 (GlucDH) | 4.2.1.40 | *E. coli* |

TABLE 7-continued

| STEP | Enzyme | EC | Organism |
|---|---|---|---|
| A | pSGI-431 (NADH_OX) | 1.6.3.1 | *Thermus thermophiilus* |
| B | Catalase | 1.11.1.6 | *Corynbacterium* |

Figure 12A:
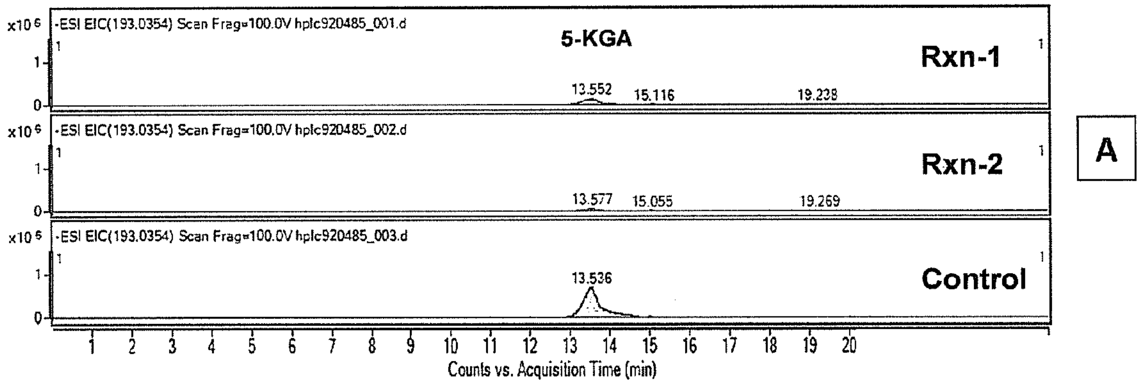
FIGS. 12*a* and 12*b* are LC-MS chromatograms showing 5-KGA and DDG reaction products, respectively.
Figure 12B:
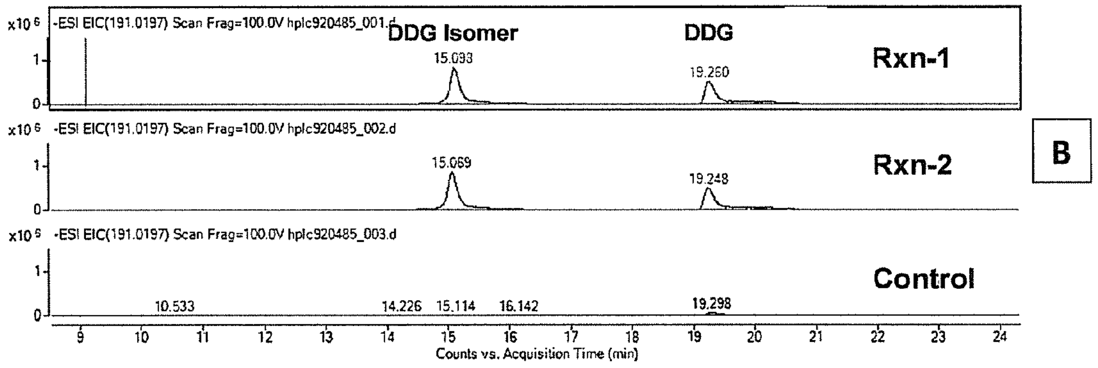

500 mL of liquid culture was purified for each isomerase for the reaction. Besides the enzymes shown on Table 7, each reaction contained 50 mM TrisHCl (pH 8.0), 50 mM NaCl, 1 mM $ZnCl_2$ and 2 mM $MgCl_2$, 1 mM $MnCl_2$ and 1 mM $NAD^+$. Reactions were analyzed by HPLC after 16 h of incubation and FIG. 12 presents the chromatograms.

Figure 13:
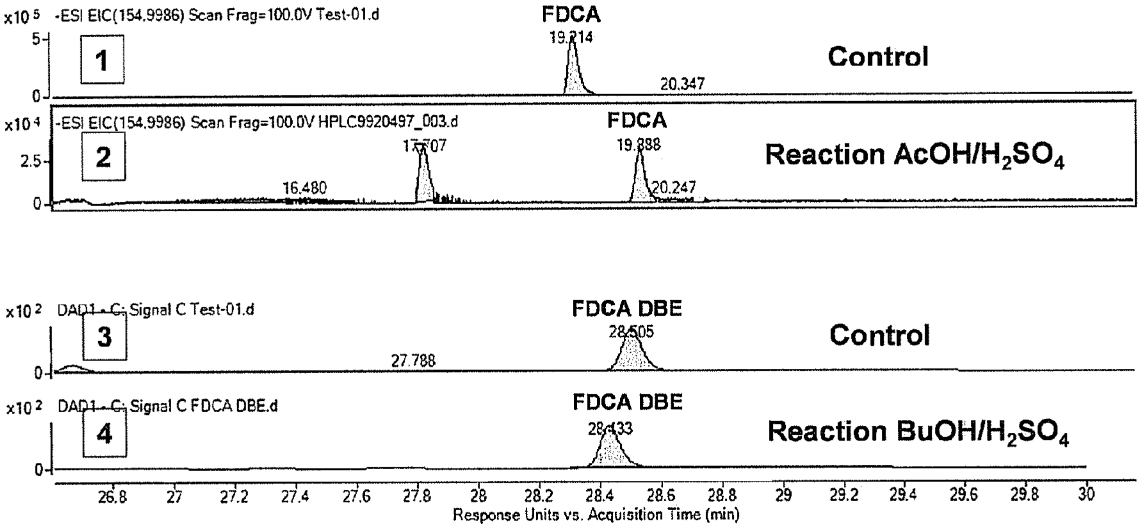
FIG. 13 is an LC-MS chromatogram showing FDCA and FDCA dibutyl ester derivative reaction products.
Figure 14A:
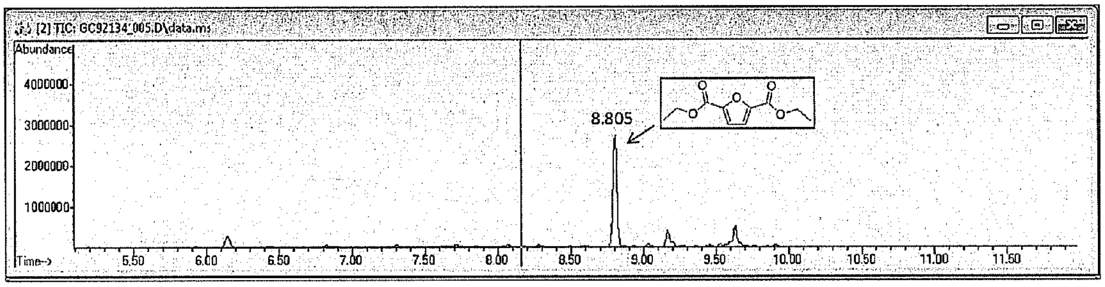
FIG. 14*a* is a GC-MS analysis of a crude reaction sample of the diethyl-FDCA synthesis from the reaction of DDG with ethanol. Single peak corresponded to diethyl-FDCA.
Figure 14B:
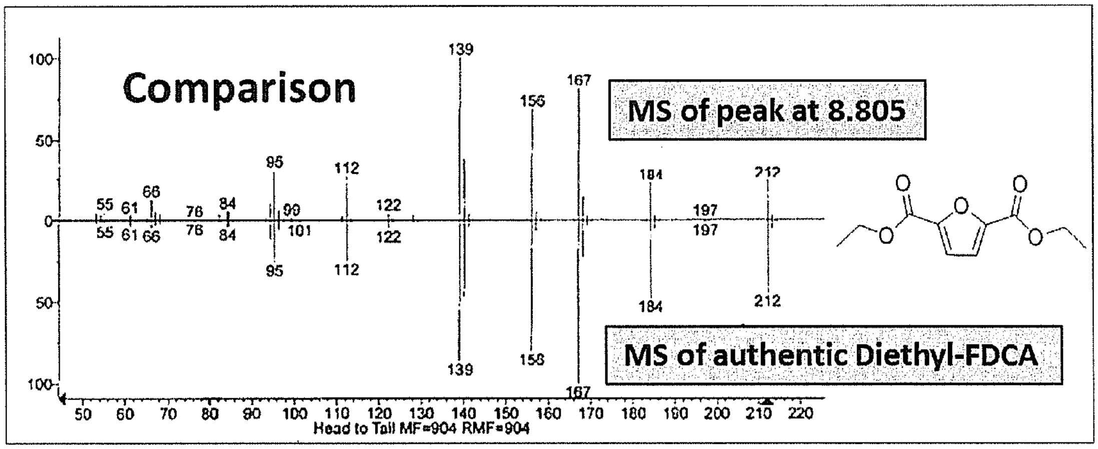
FIG. 14*b* is an MS fragmentation of the major product from the reaction of DDG with ethanol.

For dehydration to FDCA, the reaction mixtures of both samples were combined and lyophilized into a white powder, which was split into two samples and each dissolved in AcOH with 0.25M $H_2SO_4$ or in 4.5 mL BuOH with 0.25M $H_2SO_4$. Both reactions were heated in sealed vials for 2-4 h at 120° C. Reaction products are shown in FIG. 13.

Samples 1 and 2 represent authentic standard and the 3 h time point from the reaction in $AcOH/H_2SO_4$, respectively. Spiking of sample 2 with sample 1 gave a single peak further verifying the FDCA product. Samples 1 and 3 (FIG. 13) represent authentic standard and the 4 h time point from the reaction in $BuOH/H_2SO_4$, respectively. The formation of FDCA from the enzymatic reactions further confirms the presence of DDG in these samples.

Example 9

Synthesis of DDG from Glucose and Gluconate

This example shows the enzymatic conversion of glucose and gluconate to DDG. The reaction was conducted with purified enzymes, and crude lysates as a catalyst. Enzymes and substrates were combined in a bio-reactor as shown in the Table below:

| | Substrate | ST-1 | ST-14 pSGI-504 | ST-15 pSGI-434 | ST-7B pSGI-476 | ST-8A pSGI-353 | ST-A pSGI-431 | ST-B |
|---|---|---|---|---|---|---|---|---|
| Rxn-1 | Glucose 600 mg | 2 mg | 7 mL[1] | 50 mL[2] | 7.5 mL[1] | 1 mL[3] | 4 mL[4] | 2 mg |
| Rxn-2 | Gluconate 700 mg | — | 7 mL | 50 mL | 7.5 mL | 1 mL | 4 mL | 2 mg |

Figure 17:
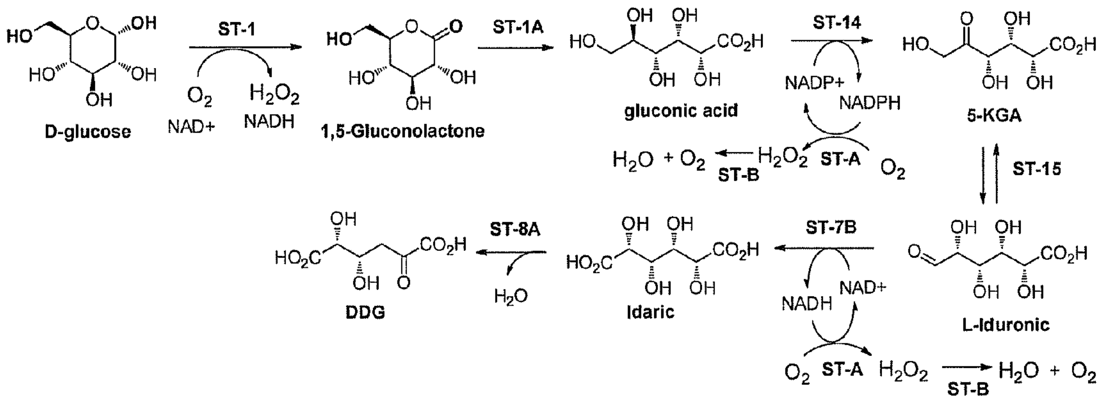
FIG. 17 is a schematic illustration of Scheme 1. Cell free enzymatic synthesis of DDG from glucose. Enzymes are ST-1: glucose oxidase; ST-1A: hydrolysis-chemical; ST-14: gluconate dehydrogenase (pSGI-504); ST-15: 5-dehydro-4-deoxy-D-glucuronate isomerase (DTHU IS, pSGI-434); ST-7B: Uronate dehydrogenase (UroDH, pSGI-476)); ST-8A Glucarate dehydratase (GlucDH, pSGI-353); ST-A: NAD(P)H oxidase (NADH OX, pSGI-431); ST-B: Catalase.
Figure 17B:
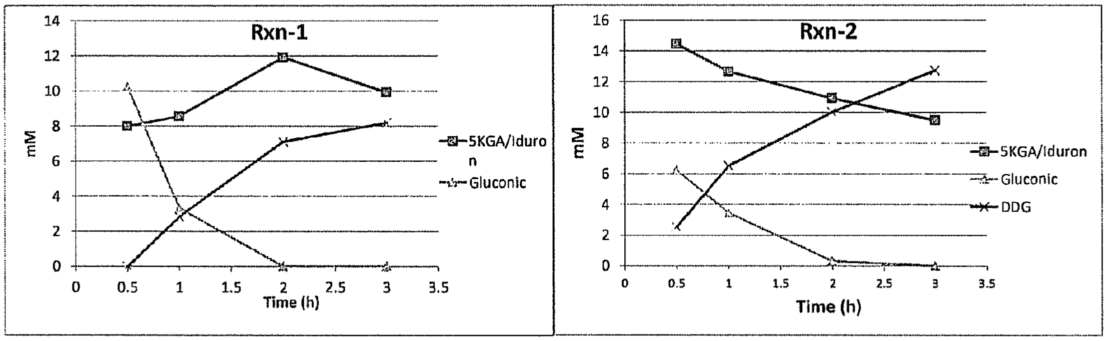
FIG. 17*b* shows the concentration of reaction intermediates over the first 3 h as analyzed by HPLC. Formation of DDG is shown in both reactions.

[1]Lysate from 500 mL liquid culture of recombinant *E. coli* with plasmid
[2]Lysate from 2 L liquid culture of BL21DE3/pSGI-434
[3]Purified enzyme, ~30 Units of activity (or 3 mg of purified GlucD)
[4]Lysate from 250 mL of culture The reaction was incubated at 35° C. and dissolved oxygen and pH were kept at 20% and 8 respectively. Time points were analyzed by HPLC-MS and the results are shown in FIG. 17*b*. Extracted chromatograms verified the DDG mass (not shown) and corresponding MS fragmentation. The results clearly showed production of DDG during incubation of the enzymes with either glucose or gluconate.

Example 10

Construction of Expression Cassettes for Recombinant Glucarate Dehydratases

The following example describes the creation of recombinant nucleic acid constructs that contained coding sequence of a D-glucarate dehydratase activity (GDH, EC 4.2.1.40) for heterologous expression in *E. coli* cells.

Genes encoding D-Glucarate dehydratase from *E. coli* (Expasy: P0AES2), *Acinetobacter* ADP1 (Expasy: P0AES2), as well as a proprietary *Pseudomonas* bacterial strain (#8114) were PCR-amplified from genomic DNA.

Each of the PCR-amplified genes was subsequently cloned into the bacterial transformation vector pET24a(+), in which the expression of each of the GDH genes was placed under control of a T7 promoter. The nucleotide sequences of each of the PCR-amplified inserts were also verified by sequencing confirmation.

Example 11

*E. coli* Strains Expressing Recombinant Glucarate Dehydratases

Each of the expression vectors constructed as described in Example 9 was introduced into NovaBlue(DE3) *E. coli* by heat shock-mediated transformation. Putative transformants were selected on LB agar supplemented with Kanamycin (50 μg/ml). Appropriate PCR primers were used in colony-PCR assays to confirm positive clones that contained each of the expression vectors.

For each expression vector, a bacterial colony was picked from transformation plates and allowed to grow at 30° C. in liquid LB media supplemented with Kanamycin (50 μg/ml) for two days. The culture was then transferred into vials containing 15% glycerol and stored at −80° C. as a frozen pure culture.

Example 12

Demonstration of In Vitro Synthesis of DDG by Using Cell Lysate of Recombinant *E. coli* Cells Expressing a GDH Enzyme This Example describes how in vitro synthesis of DDG intermediate was achieved using recombinant glucarate dehydratase (GDH) enzymes produced in *E. coli* cells.

Preparation of Cell Lysates:

Recombinant bacterial strains constructed as described previously in Example 2 were grown individually in 3 mL of liquid LB media supplemented with Kanamycin (50 μg/ml) at 30° C. on a rotating shaker with rotation speed pre-set at 250 rpm for 1 day. This preculture was used to inoculate 100 mL of TB media containing Kanamycin (50 ug/ml), followed by incubation at 30° C. on a rotating shaker pre-set at 250 rpm for 2-3 hour until early log phase ($OD_{600}$~0.5-0.6) before isopropyl D-1 thiogalactopyranoside (IPTG; 0.25 mM final concentration) was added to induce protein expression. Cells were allowed to grow for another 18 hours at 30° C. before they were harvested by centrifugation, resuspended in 15 mL of lysis buffer (10 mM phosphate buffer, pH 7.8, 2 mM $MgCl_2$) and were lysed by sonication. The production of recombinant enzymes in *E. coli* cells was quantified using standard pre-cast SDS-PAGE gels system (BioRad), and specific activity was measured according to a procedure described by Gulick et al. (*Biochemistry* 39, 4590-4602, 2000). Crude cell lysates or purified enzymes (using the HisTag) were then tested for the ability to convert gram amounts of glucarate to DDG as described in greater detail below.

Enzymatic Dehydration of Glucarate

A large scale oxidation of glucarate using glucarate dehydratase was prepared. 350 mL of water 25 g of glucaric acid sodium salt (0.1 mole) and 4.5 gr of KOH (0.8 mole) were mixed in an Erlenmyer flask. Residual solid glucarate was dissolved by the slow addition of 5M KOH solution (~3 mL) and the pH was adjusted to 7.4. In this solution 100 mg of purified glucarate dehydratase and 2 mM MgCl2 were added, and the mixture was placed in an orbital shaker at 30° C. for 20 h. The next day the precipitate is removed by filtration. The pH of the reaction was essentially unchanged. Analysis of the reaction revealed the presence of only DDG in the solution, indicating >95% yield.

Purification of DDG Product from Enzymatic Reactions:

DDG produced via enzymatic dehydration was purified by using either of the two following techniques. The enzymatic dehydration reactions were acidified to pH~3.0 with 6M HCl, filtered to eliminate precipitate, and subsequently lyophilized to produce a white powder consisting of DDG and salts. The same DDG purity (but lower amount of salts) can be obtained if the reaction was filtered through a 10 KDa membrane to remove proteins and then lyophilized. Without any further purification both previous lyophilized powders can be dehydrated to FDCA (or its esters) or can be esterified to dibutyl DDG as shown in other examples of this application.

Results of HPLC-MS analyses indicated that DDG product constituted at least 95% of the total products in the samples obtained from either of the two purification techniques.

Example 13

Demonstration of In Vitro Synthesis of FDCA from DDG in One-Step Chemical Reaction Applicants have discovered that the synthesis of FDCA (i.e. the free acid form) could be achieved by a chemical conversion of DDG to FDCA in the presence of $H_2SO_4$. The reaction was performed as follows. Approximately 20 mg of DDG acid (crude lyophilized powder with salts previously purified as described in Example 3) and 0.25 M of H2SO4 were added into an air tight sealed tube containing 1 mL of water and 1 mL of DMSO. The DDG was found completely dissolved in this solution. The reaction was stirred at 105° C. for 18 hours. Results of an HPLC-MS analysis performed on a crude reaction sample indicated the formation of FDCA free acid (FDCA: 2,5-furan dicarboxylic acid) as the major product, as well as insignificant amounts of some other unidentified byproducts. As a control in HPLC-MS analysis, a commercial FDCA was analyzed in the same conditions.

Example 14

Demonstration of In Vitro Synthesis of FDCA-Esters (Dimethyl-, Diethyl-, Dibutyl-, and Isopropyl-Esters)

Synthesis of Diethyl-2,5 FDCA from Purified DDG:

In an air tight sealed tube, 18 mL of EtOH, 0.2 gram (1 mmole) of DDG acid, previously purified as described in Example 11, and 0.25 M of $H_2SO_4$ were added. The DDG acid was not completely dissolved in this solution. The reaction was gently stirred at 105° C. for 18 hours. Results of a GC-MS analysis of a crude reaction sample indicated that the formation of diethyl-FDCA the major product. As a control, an authentic FDCA was chemically synthesized, esterified to diethyl-FDCA and analyzed in the same conditions.

Example 15

Synthesis of Dibutyl-2,5 FDCA from Purified DDG

Figure 15A:
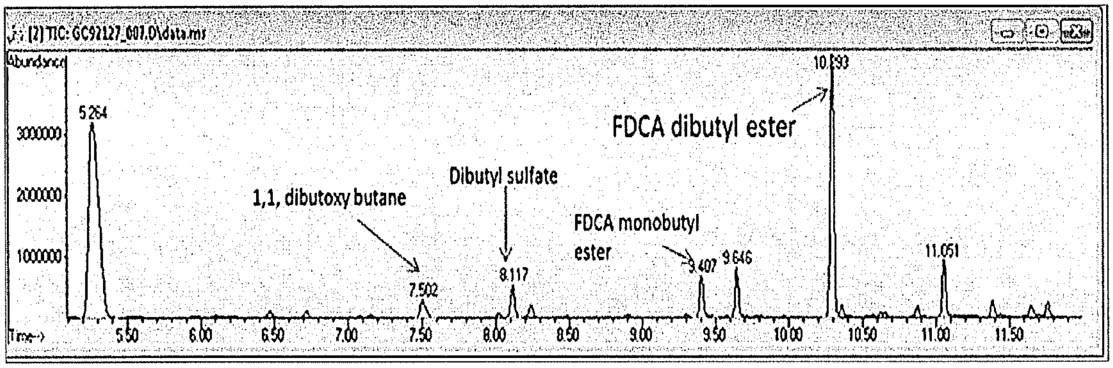
FIG. 15*a* is a GC-MS analysis of a crude reaction sample of the diethyl-FDCA synthesis from the reaction of DDG with ethanol. Single peak corresponded to diethyl-FDCA.
Figure 15B:
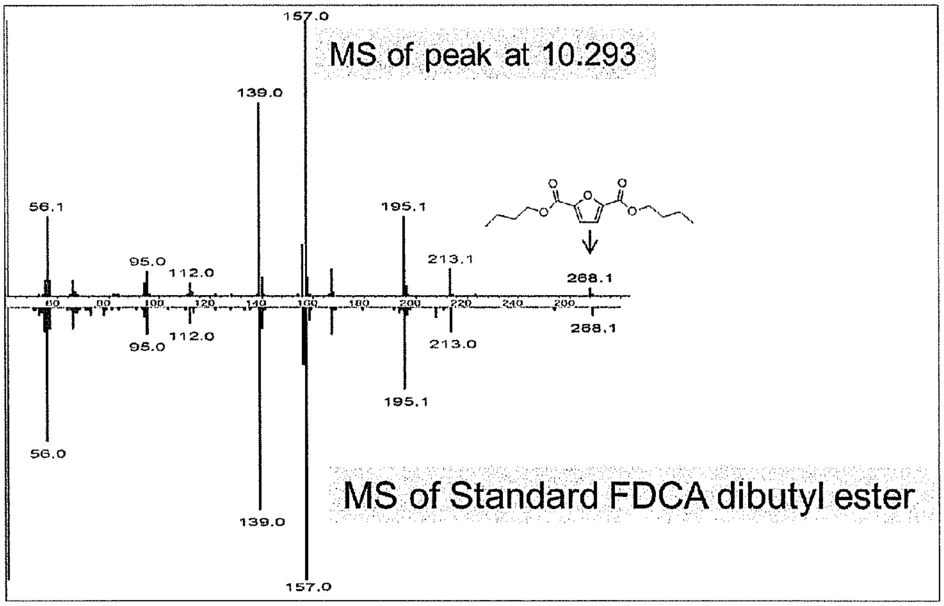
FIG. 15*b* is a MS fragmentation of the major product from the reaction of DDG with ethanol.

In an air tight sealed tube, 18 mL of n-BuOH, 0.2 gram (1 mmole) of DDG acid, previously purified as described in Example 11, and 0.25 M of $H_2SO_4$ were added. The DDG acid was not completely dissolved in this solution. The reaction was gently stirred at 105° C. for 18 hours. As shown in FIG. 15, results of the GC-MS analysis of a reaction sample indicated that diethyl-FDCA (FDCA: 2,5-furan dicarboxylic acid) was formed as the major product. As a control, an authentic FDCA was chemically synthesized, esterified to diethyl-FDCA, and analyzed in the same conditions.

Example 16

Synthesis of Dibutyl-2,5 FDCA from Crude DDG (Unpurified)

0.2 gram (1 mmole) of crude DDG acid, which was an unpurified lyophilized powder obtained directly from the enzymatic dehydration of glucarate as described in Example 11, was added into an air tight sealed tube containing 18 mL of n-BuOH, followed by addition of 0.25 M of $H_2SO_4$. The crude DDG acid was not completely dissolved in this solution. The reaction was gently stirred at 105° C. for 18 hours. Results of a GC-MS analysis of a crude reaction sample indicated that diethyl-FDCA (FDCA: 2,5-furan dicarboxylic acid) was formed as the major product. The GC-MS result indicated that the present of contaminant salts in crude/unpurified lyophilized powder did not significantly affect the reaction outcome. As a control, an authentic FDCA was chemically synthesized, esterified to diethyl-FDCA, and analyzed in the same conditions.

Example 17

In Vitro Production of FDCA and/or Esters Using Immobilized Acids

In industrial practices, immobilized acids offer many advantages for performing dehydrations since they can typically operate in several types of solvent (aqueous, organic or mixed, etc.). In addition, they can be easily recycled and be re-used. Following some examples of the synthesis of esters of FDCA using immobilized AMBERLYST®15 (Rohm and Haas, Philadelphia, Pa.) and DOWEX®50 WX8 (Dow Chemical Co, Midland, Mich.).

Synthesis of Dibutyl-FDCA from Crude DDG by Using DOWEX®50 WX8

In an air tight sealed tube, 2 mL of n-Butanol, 20 mg of crude DDG acid (unpurified lyophilized powder containing salts) and 200 mg of DOWEX®50 WX8 were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, an authentic FDCA was chemically synthesized esterified to diethyl-FDCA and analyzed in the same conditions.

Synthesis of Dibutyl-FDCA from Crude DDG by Using AMBERLYST®15

In an air tight sealed tube, 2 mL of n-Butanol, 20 mg of crude DDG acid (crude lyophilized powder with salts) and 200 mg of AMBERLYST®15 (Rohm and Haas, Philadelphia, Pa.) were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, an authentic FDCA was chemically synthesized esterified to diethyl-FDCA and analyzed in the same conditions.

Synthesis of Ethyl-FDCA from Crude DDG by Using AMBERLYST®15

In an air tight sealed tube, 2 mL of ethanol, 20 mg of crude DDG acid (unpurified lyophilized powder containing salts) and 200 mg of AMBERLYST®15 (Rohm and Haas, Philadelphia, Pa.) were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, a commercial FDCA was chemically esterified to diethyl-FDCA and analyzed in the same conditions.

Synthesis of Diethyl-FDCA from Crude DDG by Using DOWEX®50 WX8

In an air tight sealed tube, 2 mL of ethanol, 20 mg of crude DDG acid (unpurified lyophilized powder containing salts) and 200 mg of DOWEX®50 WX8 were combined. The DDG was not completely dissolved in this solution. The reaction was gently stirred at 105° C. for 18 hours. Results of the GC-MS analysis of a crude reaction sample indicated that diethyl-FDCA (FDCA: 2,5-furan dicarboxylic acid) was formed as the major product. This GC-MS result indicated that the present of contaminant salts (phosphate and NaCl) in crude/unpurified lyophilized powder did not significantly affect the reaction outcome. As a control, a commercial FDCA was chemically esterified to diethyl-FDCA and analyzed in the same conditions.

Example 18

Production of FDCA Derivatives

Figure 16:
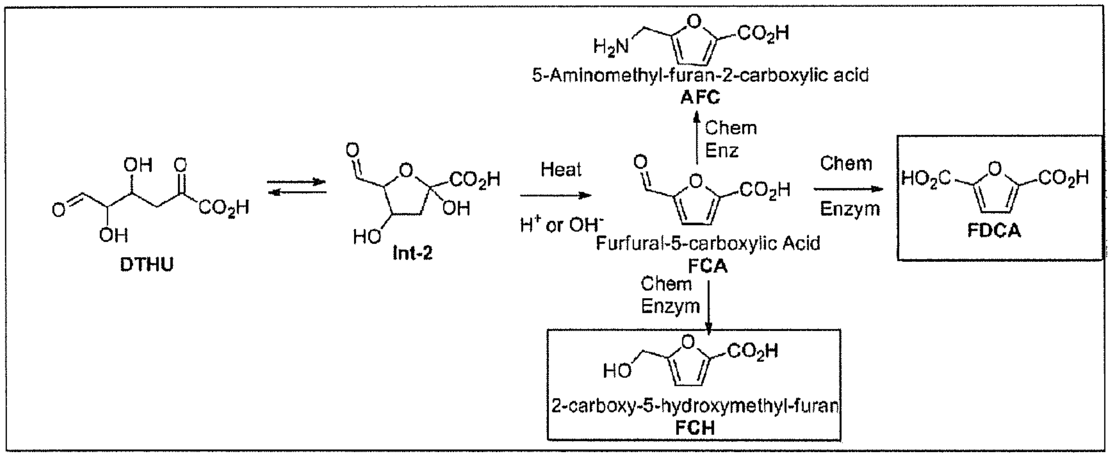
FIG. 16 is a schematic illustration of the synthesis of FDCA and its derivatives from DTHU.

The synthesis of a number of high-value FDCA derivatives is described in FIG. 16 in which dehydration of DTHU produces furfural-5-carboxylic acid, i.e. FCA, which is then chemically or enzymatically oxidized to FDCA, be reduced to FCH, or be transaminated (using chemical reductive amination or transaminase) to amino acid-AFC.

Example 19

Production of Di-Butyl FDCA in a Gas Phase Reaction

In this example the inlet of the GC was used as a high temperature reactor to catalyze the dehydration of di-butyl DDG to di-butyl FDCA. The resulting products were chromatographically separated detected by mass spectrometry. A solution of di-butyl DDG (10 mM) and sulfuric acid (100 mM) in butanol was placed in a GC vial. The vial was injected into a GC and FDCA Dibutyl ester was observed. The reaction occurred in the 300° C. inlet (residence time=4 seconds). The average yield of 6 injections was 54%.

GC Settings: Direct Liquid Inject/MS Detector

Inlet: 300° C., total flow 29.51 ml/min, split ratio 10:1, split flow 24.1 ml/min, Septum Purge flow 3 mL/min.

GC liner: 4 mm, glass wool (P/N 5183-4647)

Column Flow: 2.41 ml/min He constant pressure control

Oven Program: At 40° C. hold for 2 min, then ramp 25° C./min to 275° C., then ramp 40° C./min to 325° C., hold for 2 min.

Column: HP-5MS, Agilent Technologies, 30 m×0.25 mm×0.25 um.

Total Runtime: 14.65 minutes

MSD Transfer line: 290° C.

MS Source: 250° C.

MS Quad: 150° C.

Retention Times:

2,3-FDCA Dibutyl ester: 9.3 min 2,5-FDCA Dibutyl ester: 9.7 min

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that although a number of prior art publications are referred to herein, this reference does not constitute an admission that any of these documents forms part of the common general knowledge in the art.

It should also be understood that the foregoing examples are offered to illustrate, but not limit, the invention.

What is claimed is:

1. A method for producing a product of an enzymatic or chemical pathway from a starting substrate, the pathway comprising one or more conversion steps selected from the group consisting of:

contacting guluronic acid with a uronate dehydrogenase to perform an enzymatic conversion of guluronic acid into D-glucarate (Step 7);

contacting 5-ketogluconate (5-KGA) with an isomerase to perform an enzymatic conversion of 5-ketogluconate (5-KGA) into L-Iduronic acid (Step 15);

contacting L-Iduronic acid with a uronate dehydrogenase to perform an enzymatic conversion of L-Iduronic acid into Idaric acid (Step 7b); and contacting 5-ketogluconate with a gluconate dehydratase to perform an enzymatic conversion of 5-ketogluconate into 4,6-dihydroxy 2,5-diketo hexanoate (2,5-DDH) (Step 16); and contacting 1,5-gluconolactone with an alditol oxidase to perform an enzymatic conversion of 1,5-gluconolactone to gulurono-lactone (Step 19).

2. The method of claim 1 wherein the one or more conversion steps comprises contacting guluronic acid with a uronate dehydrogenase to perform the enzymatic conversion of guluronic acid into D-glucarate (Step 7).

3. The method of claim 1 wherein the one or more conversion steps comprises contacting 5-ketogluconate (5-KGA) with an isomerase to perform the enzymatic conversion of 5-ketogluconate (5-KGA) into L-Iduronic acid (Step 15).

4. The method of claim 1 wherein the one or more conversion steps comprises contacting L-Iduronic acid with a uronate dehydrogenase to perform the enzymatic conversion of L-Iduronic acid into Idaric acid Step 7b).

5. The method of claim 1 wherein the one or more conversion steps comprises contacting 5-ketogluconate with a gluconate dehydratase to perform the enzymatic conversion of 5-ketogluconate into 4,6-dihydroxy 2,5-diketo hexanoate (2,5-DDH) (Step 16).

6. The method of claim 1 wherein the one or more conversion steps comprises contacting 1,5-gluconolactone with an alditol oxidase to perform the enzymatic conversion of 1,5-gluconolactone to gulurono-lactone (Step 19).

7. The method of claim 1 wherein the pathway is an enzymatic pathway and the product is 5-dehydro-4-deoxy-glucarate (DDG).

8. The method of claim 1 wherein the substrate is glucose and the product is 5-dehydro-4-deoxy-glucarate (DDG), comprising the steps of:

contacting D-glucose with an oxygen dependent glucose oxidase or an NAD(P)-dependent glucose dehydrogenase to perform an enzymatic conversion of D-glucose to 1,5-gluconolactone (Step 1);

contacting 1,5-gluconolactone with an alditol oxidase to perform the enzymatic conversion of 1,5-gluconolactone to gulurono-lactone (Step 19);

contacting gulurono-lactone with a lactonase to perform an enzymatic conversion of gulurono-lactone to guluronic acid (Step 1B), or converting gulurono-lactone to guluronic acid by spontaneous reaction in an aqueous solution;

contacting guluronic acid with a uronate dehydrogenase to perform the enzymatic conversion of guluronic acid to D-glucarate (Step 7);

contacting D-glucarate with a glucarate dehydratase to perform an enzymatic conversion of D-glucarate to 5-dehydro-4-deoxy-glucarate (DDG) (Step 8).

9. A method of claim 1 wherein the substrate is glucose and the product is DDG, comprising the steps of:

contacting D-glucose with an oxygen dependent glucose oxidase to produce 1,5-gluconolactone (Step 1);

hydrolyzing 1,5-gluconolactone to gluconic acid (Step 1a);

contacting gluconic acid with an NAD(P)-dependent dehydrogenase to produce 5-ketogluconate (5-KGA) (Step 14);

contacting 5-ketogluconate (5-KGA) with an isomerase to produce L-Iduronic acid (Step 15);

contacting L-Iduronic acid with a uronate dehydrogenase to produce Idaric acid (Step 7b); and contacting Idaric acid with a glucarate dehydratase to produce DDG (Step 8a).

10. A method of claim 1 wherein the substrate is glucose and the product is DDG, comprising the steps of:

contacting D-glucose with an oxygen dependent glucose oxidase and an NAD(P)-dependent glucose dehydrogenase to produce 1,5-gluconolactone (Step 1);

hydrolyzing 1,5-gluconolactone to gluconic acid (Step 1a);

contacting gluconic acid with an NAD(P)-dependent dehydrogenase to produce 5-ketogluconate (5-KGA) (Step 14);

contacting 5-ketogluconate (5-KGA) with a gluconate dehydratase to produce 4,6-dihydroxy 2,5-diketo hexanoate (2,5-DDH) (Step 16);

contacting 4,6-dihydroxy 2,5-diketo hexanoate (2,5-DDH) with a glucoronate isomerase to produce 4-deoxy-5-threo-hexosulose uronate (DTHU) (Step 4); and oxidizing 4-deoxy-5-threo-hexosulose uronate (DTHU) to DDG (Step 5).

11. A method of claim 1 wherein the substrate is glucose and the product is DDG, comprising the steps of:

contacting D-glucose with an oxygen dependent glucose oxidase to produce 1,5-gluconolactone (Step 1);

hydrolyzing 1,5-gluconolactone to gluconic acid (Step 1a);

contacting gluconic acid with an NAD(P)-dependent dehydrogenase to produce 5-ketogluconate (5-KGA) (Step 14);

contacting 5-ketogluconate (5-KGA) with an isomerase to produce L-Iduronic acid (Step 15);

contacting L-Iduronic acid with a uronate dehydrogenase to produce 4-deoxy-5-threo-hexosulose uronate (DTHU) (Step 7b); and oxidizing 4-deoxy-5-threo-hexosulose uronate (DTHU) to produce DDG (Step 5).

12. The method of claim 8 further comprising the step of converting the DDG to 2,5-furan-dicarboxylic acid (FDCA) by contacting the DDG with an inorganic acid.

13. The method of claim 9 further comprising the step of converting the DDG to 2,5-furan-dicarboxylic acid (FDCA) by contacting the DDG with an inorganic acid.

14. The method of claim 10 further comprising the step of converting the DDG to 2,5-furan-dicarboxylic acid (FDCA) by contacting the DDG with an inorganic acid.

15. The method of claim 11 further comprising the step of converting the DDG to 2,5-furan-dicarboxylic acid (FDCA) by contacting the DDG with an inorganic acid.

16. The method of claim 2 wherein the uronate dehydrogenase comprises SEQ ID NO: 1-3 or a homolog having at least 70% sequence identity to SEQ ID NOs: 1-3; or is encoded by a nucleic acid of SEQ ID NOs: 4-6 or a homolog having at least 70% sequence identity to a nucleic acid of SEQ ID NOs: 4-6.

17. The method of claim 3 wherein the isomerase comprises SEQ ID NOs: 7-19 or a homolog having at least 70% sequence identity to an isomerase of SEQ ID NOs: 7-19; or is encoded by a nucleic acid of SEQ ID NOs: 20-32 or a homolog having at least 70% sequence identity to a nucleic acid of SEQ ID NOs: 20-32.

18. The method of claim 5 wherein the gluconate dehydratase comprises SEQ ID NOs: 33-35 or a homolog having at least 70% sequence identity to a gluconate dehydratase of SEQ ID NOs: 33-35; or is encoded by a nucleic acid of SEQ ID NOs: 36-38 or a homolog having at least 70% sequence identity to a nucleic acid of SEQ ID NOs: 36-38.

19. The method of claim 6 wherein the alditol oxidase comprises SEQ ID NOs: 39-46 or a homolog having at least 70% sequence identity to an alditol oxidase of SEQ ID NOs: 39-46; or is encoded by a nucleic acid of SEQ ID NOs: 47-54 or a homolog having at least 70% sequence identity to a nucleic acid of SEQ ID NOs: 47-54.

20. The method of claim 4 wherein the uronate dehydrogenase comprises SEQ ID NO: 1-3 or a homolog having at least 70% sequence identity to SEQ ID NOs: 1-3; or is encoded by a nucleic acid of SEQ ID NOs: 4-6 or a homolog having at least 70% sequence identity to a nucleic acid of SEQ ID NOs: 4-6.

* * * * *

SEQUENCE LISTING

```
<160> NUMBER OF SEQ ID NOS: 84

<210> SEQ ID NO 1
<211> LENGTH: 267
<212> TYPE: PRT
<213> ORGANISM: Agrobacterium tumefaciens

<400> SEQUENCE: 1
```

-continued

```
Met Ala Met Lys Arg Leu Leu Val Thr Gly Ala Ala Gly Gln Leu Gly
1               5                   10                  15

Arg Val Met Arg Lys Arg Leu Ala Ser Met Ala Glu Ile Val Arg Leu
            20                  25                  30

Ala Asp Leu Ala Pro Leu Asp Pro Ala Gly Pro Asn Glu Glu Cys Met
        35                  40                  45

Gln Cys Asp Leu Ala Asp Ala Asp Ala Val Asp Ala Met Val Ala Gly
    50                  55                  60

Cys Asp Gly Ile Val His Leu Gly Gly Ile Ser Val Glu Lys Pro Phe
65                  70                  75                  80

Glu Gln Ile Leu Gln Gly Asn Ile Ile Gly Leu Tyr Asn Leu Tyr Glu
                85                  90                  95

Ala Ala Arg Ala His Gly Gln Pro Arg Ile Ile Phe Ala Ser Ser Asn
            100                 105                 110

His Thr Ile Gly Tyr Tyr Pro Gln Thr Glu Arg Leu Gly Pro Asp Val
        115                 120                 125

Pro Phe Arg Pro Asp Gly Leu Tyr Gly Val Ser Lys Cys Phe Gly Glu
    130                 135                 140

Ser Leu Ala Arg Met Tyr Phe Glu Lys Phe Gly Gln Glu Thr Ala Leu
145                 150                 155                 160

Val Arg Ile Gly Ser Cys Thr Pro Glu Pro Leu Asn Tyr Arg Met Leu
                165                 170                 175

Ser Thr Trp Phe Ser His Asp Asp Phe Val Ser Leu Ile Glu Ala Ala
            180                 185                 190

Phe Arg Ala Pro Val Leu Gly Cys Pro Ile Val Trp Gly Ala Ser Ala
        195                 200                 205

Asn Asp Ala Ser Trp Trp Asp Asn Ser His Leu Gly Phe Ile Gly Trp
    210                 215                 220

Lys Pro Lys Asp Asn Ala Glu Ala Phe Arg Arg Lys Ile Ala Glu Thr
225                 230                 235                 240

Thr Pro Gln Pro Asp Ala Arg Asp Pro Ile Val Arg Phe Gln Gly Gly
                245                 250                 255

Val Phe Val Asp Asn Pro Ile Phe Lys Glu Thr
            260                 265


<210> SEQ ID NO 2
<211> LENGTH: 266
<212> TYPE: PRT
<213> ORGANISM: Rhizobium lupini

<400> SEQUENCE: 2

Met Lys Arg Leu Leu Ile Thr Gly Ala Ala Gly Ala Leu Gly Arg Val
1               5                   10                  15

Met Arg Glu Arg Leu Ala Pro Met Ala Thr Ile Leu Arg Leu Ser Asp
            20                  25                  30

Ile Ala Pro Ile Gly Ala Ala Arg Gln Asn Glu Glu Ile Val Gln Cys
        35                  40                  45

Asp Leu Ala Asp Ala Lys Ala Val His Ala Leu Val Glu Asp Cys Asp
    50                  55                  60

Gly Ile Val His Leu Gly Gly Val Ser Val Glu Arg Lys Phe Ser Gln
65                  70                  75                  80

Ile Val Ala Gly Asn Ile Val Gly Leu Tyr Asn Leu Tyr Glu Ala Ala
                85                  90                  95

Arg Ala His Arg Met Pro Arg Ile Val Phe Ala Ser Ser Asn His Thr
```

-continued

```
            100                 105                 110

Ile Gly Phe Tyr Pro Gln Thr Glu Arg Leu Ser Val Asp His Pro Tyr
        115                 120                 125

Arg Pro Asp Gly Leu Tyr Gly Val Ser Lys Cys Phe Gly Glu Ser Leu
    130                 135                 140

Ala His Met Tyr His Glu Lys Phe Gly Gln Glu Thr Ala Leu Val Arg
145                 150                 155                 160

Ile Gly Ser Cys Val Thr Glu Pro Val Asn His Arg Met Leu Ser Thr
                165                 170                 175

Trp Leu Ser Tyr Asp Asp Phe Val Ser Leu Ile Glu Ala Val Phe Arg
            180                 185                 190

Ala Pro Lys Leu Gly Cys Pro Val Ile Trp Gly Ala Ser Asn Asn Asp
        195                 200                 205

Ala Gly Trp Trp Asp Asn Ser Ala Ala Gly Phe Leu Gly Trp Lys Pro
    210                 215                 220

Lys Asp Asn Ala Glu Ile Phe Arg Ser Lys Ile Glu Ala Ala Cys Glu
225                 230                 235                 240

Arg Pro Gly Ser Asp Asp Pro Ala Ala Arg Trp Gln Gly Gly Leu Phe
                245                 250                 255

Thr Gln Asp Pro Ile Phe Pro Glu Asp Glu
            260                 265


<210> SEQ ID NO 3
<211> LENGTH: 272
<212> TYPE: PRT
<213> ORGANISM: Pseudomonas sp.

<400> SEQUENCE: 3

Met Thr Thr Ala Tyr Thr Pro Phe Asn Arg Leu Leu Leu Thr Gly Ala
1               5                   10                  15

Ala Gly Gly Leu Gly Lys Val Leu Arg Glu Ser Leu Arg Pro Tyr Ala
            20                  25                  30

Asn Val Leu Arg Val Ser Asp Ile Ala Ala Met Ser Pro Ala Thr Gly
        35                  40                  45

Ala His Glu Glu Val Gln Val Cys Asp Leu Ala Asp Lys Ala Ala Val
    50                  55                  60

His Gln Leu Val Glu Gly Val Asp Ala Ile Leu His Phe Gly Gly Val
65                  70                  75                  80

Ser Val Glu Arg Pro Phe Glu Glu Ile Leu Gly Ala Asn Ile Cys Gly
                85                  90                  95

Val Phe His Ile Tyr Glu Ala Ala Arg Arg His Gly Val Lys Arg Val
            100                 105                 110

Ile Phe Ala Ser Ser Asn His Val Ile Gly Phe Tyr Lys Gln Asp Glu
        115                 120                 125

Thr Ile Asp Ala Asn Cys Pro Arg Arg Pro Asp Ser Tyr Tyr Gly Leu
    130                 135                 140

Ser Lys Ser Tyr Gly Glu Asp Met Ala Ser Phe Tyr Phe Asp Arg Tyr
145                 150                 155                 160

Gly Ile Glu Thr Val Ser Ile Arg Ile Gly Ser Ser Phe Pro Glu Pro
                165                 170                 175

His Asn Arg Arg Met Met Ser Thr Trp Leu Ser Phe Ala Asp Leu Thr
            180                 185                 190

Gln Leu Leu Glu Arg Ala Leu Tyr Thr Pro Asn Val Gly His Thr Val
        195                 200                 205
```

-continued

```
Val Tyr Gly Met Ser Ala Asn Lys Asn Val Trp Trp Asp Asn His Leu
    210                 215                 220

Ala Ala His Leu Gly Phe Gln Pro Lys Asp Ser Ser Glu Val Phe Arg
225                 230                 235                 240

Ala Gln Ile Asp Ala Gln Pro Met Pro Ala Ala Asp Asp Pro Ala Met
                245                 250                 255

Val Phe Gln Gly Gly Ala Phe Val Ala Ala Gly Pro Phe Gly Asp Asp
            260                 265                 270
```

<210> SEQ ID NO 4
<211> LENGTH: 804
<212> TYPE: DNA
<213> ORGANISM: Agrobacterium tumefaciens

<400> SEQUENCE: 4

```
atggcaatga aacggcttct tgttaccggt gctgcgggcc agcttggccg cgttatgcgc     60

aaacgccttg catcgatggc cgagatcgtt cgccttgccg atctcgcccc gctcgatccg    120

gcaggcccga acgaggaatg catgcaatgc gaccttgcgg atgcagacgc cgttgacgcc    180

atggttgccg gttgcgacgg catcgttcac ctcggcggca tatcggtgga gaagcctttc    240

gaacaaatcc ttcagggcaa catcatcggg ctgtataatc tctatgaggc cgcccgcgcc    300

cacggccagc cgcgcatcat cttcgccagt tcgaaccata cgatcggtta ttacccgcag    360

acggagaggc ttggaccgga tgttcccttc cgcccggatg ggctttacgg cgtctccaaa    420

tgtttcggcg agagccttgc ccgcatgtat ttcgagaaat tcggccagga gaccgcactt    480

gtccgcatcg gctcctgcac gccggaaccc cttaattacc gcatgctgtc cacctggttt    540

tcgcatgacg atttcgtctc gctgatcgag gcggcgttcc gcgcccccgt gctcggctgc    600

cccatcgtct gggggcgtc ggccaacgat gcgagctggt gggacaattc gcatctcggc     660

tttattggat ggaaaccgaa ggacaatgcc gaggccttcc gccggaagat tgccgaaacg    720

acgccgcagc cggacgcgcg cgacccgatt gtccgctttc agggtggcgt gtttgtcgac    780

aacccgatct tcaaggagac gtga                                           804
```

<210> SEQ ID NO 5
<211> LENGTH: 801
<212> TYPE: DNA
<213> ORGANISM: Rhizobium lupini

<400> SEQUENCE: 5

```
atgaagagac ttctgattac cggcgcagcg ggtgcactgg gccgcgtgat gcgggaaagg     60

ctcgcaccca tggcaacgat tctgcgcctt tccgatatcg ccccgattgg agcggcccgc    120

cagaacgagg aaatcgtcca gtgcgatctt gccgatgcca aagcagtgca tgctctggtc    180

gaagattgcg acgggatcgt ccatctcggt ggcgtctcag tagagcgcaa gttctcgcag    240

atcgtcgccg gcaacatcgt cggcctttac aatctctacg aagccgcacg cgcgcatcgg    300

atgccgcgca tcgtctttgc aagttccaat cacaccatcg gcttttatcc gcaaaccgaa    360

cggttgtcgg tggaccatcc ctatcgtccg gacgggctct acggcgtatc gaaatgtttc    420

ggcgagtctc tggcgcatat gtaccatgag aagttcgggc aggagacggc actcgtgcgc    480

atcgggtcct gcgtgaccga accggtcaac catcgcatgc tttccacctg gctttcctac    540

gatgatttcg tctcgcttat cgaggccgta ttccgtgcgc cgaaactcgg ctgccccgtc    600

atctggggcg cgtcgaacaa cgatgcagga tggtgggaca attccgccgc cggctttctc    660

ggctggaagc cgaaagacaa tgccgaaatc ttccgttcga agatcgaagc cgcttgcgaa    720
```

-continued cgccccggtt ctgatgatcc ggccgcccgc tggcaaggcg ggctcttcac gcaggacccg 780
atcttcccag aggacgagta a 801

<210> SEQ ID NO 6
<211> LENGTH: 819
<212> TYPE: DNA
<213> ORGANISM: Pseudomonas sp.

<400> SEQUENCE: 6
atgaccacag cctacacccc cttcaatcgc ctgctactca ccggagcggc aggcggcctc 60
ggcaaggtcc tgcgcgaaag cctgcgacct tatgccaacg tcctgcgcgt ctccgacatc 120
gcggccatga gccctgccac aggcgcccat gaagaagtcc aggtctgcga cctcgccgat 180
aaagcggcgg tccatcaact ggtcgaaggc gtcgacgcaa tcctgcactt cggtggcgta 240
tcggtggagc ggcccttcga ggaaatcctc ggggccaata tctgcggcgt gtttcatatc 300
tatgaagcgg cgcgccggca tggcgtaaag cgggtgatct tcgccagctc caaccacgtc 360
atcggttttt ataagcagga cgaaaccatc gacgccaact gcccgcgccg ccccgacagc 420
tactacggtc tgtccaagtc ctacggcgaa gacatggcca gcttctactt cgaccgctac 480
ggcatcgaga ccgtgagcat ccgcatcggc tcctcgttcc ccgagccgca caatcgccgc 540
atgatgagca cctggctgag ctttgccgac ctgacgcagc tgctcgaacg cgcgctgtac 600
acccccaacg tcggccacac cgtggtctac ggcatgtccg ctaacaagaa cgtctggtgg 660
gacaaccacc tggccgcgca cctgggcttc caaccgaagg acagctccga ggtgttccgt 720
gcgcagatcg atgcccagcc gatgcccgcc gccgatgacc cggcgatggt ctttcaaggc 780
ggcgcctttg tcgcagccgg gccgttcggc gacgactga 819

<210> SEQ ID NO 7
<211> LENGTH: 274
<212> TYPE: PRT
<213> ORGANISM: Rhizobium sp.

<400> SEQUENCE: 7

Met Leu Asn Val Glu Thr Arg His Ala Val His Ala Asp His Ala Arg
1 5 10 15

Ser Leu Asp Thr Glu Gly Leu Arg Arg His Phe Leu Ala Gln Gly Leu
20 25 30

Phe Ala Glu Gly Glu Ile Arg Leu Ile Tyr Thr His Tyr Asp Arg Phe
35 40 45

Val Met Gly Gly Ala Val Pro Asp Gly Ala Pro Leu Val Leu Asp His
50 55 60

Val Glu Glu Thr Lys Thr Pro Gly Phe Leu Asp Arg Arg Glu Met Gly
65 70 75 80

Ile Val Asn Ile Gly Ala Glu Gly Ser Val His Ala Gly Asn Glu Ser
85 90 95

Trp Ser Leu Asn Arg Gly Asp Val Leu Tyr Leu Gly Met Gly Ala Gly
100 105 110

Pro Val Thr Phe Glu Gly Ala Gly Arg Phe Tyr Leu Val Ser Ala Pro
115 120 125

Ala His Arg Ser Leu Pro Asn Arg Leu Val Thr Pro Ala Asp Ser Lys
130 135 140

Glu Val Lys Leu Gly Ala Leu Glu Thr Ser Asn Lys Arg Thr Ile Asn
145 150 155 160

-continued

```
Gln Phe Ile His Pro Leu Val Met Glu Ser Cys Gln Leu Val Leu Gly
                165                 170                 175

Tyr Thr Thr Leu Glu Asp Gly Ser Val Trp Asn Thr Met Pro Ala His
            180                 185                 190

Val His Asp Arg Arg Met Glu Ala Tyr Leu Tyr Phe Gly Met Asp Glu
        195                 200                 205

Thr Ser Arg Val Leu His Leu Met Gly Glu Pro Gln Gln Thr Arg His
    210                 215                 220

Leu Phe Val Ala Asn Glu Glu Gly Ala Ile Ser Pro Pro Trp Ser Ile
225                 230                 235                 240

His Ala Gly Ala Gly Ile Gly Ser Tyr Thr Phe Ile Trp Ala Met Ala
                245                 250                 255

Gly Asp Asn Val Asp Tyr Thr Asp Met Glu Phe Ile Gln Pro Gly Asp
            260                 265                 270

Leu Arg


<210> SEQ ID NO 8
<211> LENGTH: 278
<212> TYPE: PRT
<213> ORGANISM: Escherichia coli K-12

<400> SEQUENCE: 8

Met Asp Val Arg Gln Ser Ile His Ser Ala His Ala Lys Thr Leu Asp
1               5                   10                  15

Thr Gln Gly Leu Arg Asn Glu Phe Leu Val Glu Lys Val Phe Val Ala
            20                  25                  30

Asp Glu Tyr Thr Met Val Tyr Ser His Ile Asp Arg Ile Ile Val Gly
        35                  40                  45

Gly Ile Met Pro Ile Thr Lys Thr Val Ser Val Gly Gly Glu Val Gly
    50                  55                  60

Lys Gln Leu Gly Val Ser Tyr Phe Leu Glu Arg Arg Glu Leu Gly Val
65                  70                  75                  80

Ile Asn Ile Gly Gly Ala Gly Thr Ile Thr Val Asp Gly Gln Cys Tyr
                85                  90                  95

Glu Ile Gly His Arg Asp Ala Leu Tyr Val Gly Lys Gly Ala Lys Glu
            100                 105                 110

Val Val Phe Ala Ser Ile Asp Thr Gly Thr Pro Ala Lys Phe Tyr Tyr
        115                 120                 125

Asn Cys Ala Pro Ala His Thr Thr Tyr Pro Thr Lys Lys Val Thr Pro
    130                 135                 140

Asp Glu Val Ser Pro Val Thr Leu Gly Asp Asn Leu Thr Ser Asn Arg
145                 150                 155                 160

Arg Thr Ile Asn Lys Tyr Phe Val Pro Asp Val Leu Glu Thr Cys Gln
                165                 170                 175

Leu Ser Met Gly Leu Thr Glu Leu Ala Pro Gly Asn Leu Trp Asn Thr
            180                 185                 190

Met Pro Cys His Thr His Glu Arg Arg Met Glu Val Tyr Phe Tyr Phe
        195                 200                 205

Asn Met Asp Asp Asp Ala Cys Val Phe His Met Met Gly Gln Pro Gln
    210                 215                 220

Glu Thr Arg His Ile Val Met His Asn Glu Gln Ala Val Ile Ser Pro
225                 230                 235                 240

Ser Trp Ser Ile His Ser Gly Val Gly Thr Lys Ala Tyr Thr Phe Ile
                245                 250                 255
```

Trp Gly Met Val Gly Glu Asn Gln Val Phe Asp Asp Met Asp His Val
260 265 270

Ala Val Lys Asp Leu Arg
275

<210> SEQ ID NO 9
<211> LENGTH: 278
<212> TYPE: PRT
<213> ORGANISM: Rhizobium sp.

<400> SEQUENCE: 9

Met Thr Met Lys Ile Leu Tyr Gly Ala Gly Pro Glu Asp Val Lys Gly
1 5 10 15

Tyr Asp Thr Gln Arg Leu Arg Asp Ala Phe Leu Leu Asp Asp Leu Phe
20 25 30

Ala Asp Asp Arg Val Ser Phe Thr Tyr Thr His Val Asp Arg Leu Ile
35 40 45

Leu Gly Gly Ala Val Pro Val Thr Thr Ser Leu Thr Phe Gly Ser Gly
50 55 60

Thr Glu Ile Gly Thr Pro Tyr Leu Leu Ser Ala Arg Glu Met Gly Ile
65 70 75 80

Ala Asn Leu Gly Gly Thr Gly Thr Ile Glu Val Asp Gly Gln Arg Phe
85 90 95

Thr Leu Glu Asn Arg Asp Val Leu Tyr Val Gly Arg Gly Ala Arg Gln
100 105 110

Met Thr Ala Ser Ser Leu Ser Ala Glu Arg Pro Ala Arg Phe Tyr Met
115 120 125

Asn Ser Val Pro Ala Gly Ala Asp Phe Pro His Arg Leu Ile Thr Arg
130 135 140

Gly Glu Ala Lys Pro Leu Asp Leu Gly Asp Ala Arg Arg Ser Asn Arg
145 150 155 160

Arg Arg Leu Ala Met Tyr Ile His Pro Glu Val Ser Pro Ser Cys Leu
165 170 175

Leu Leu Met Gly Ile Thr Asp Leu Ala Glu Gly Ser Ala Trp Asn Thr
180 185 190

Met Pro Pro His Leu His Glu Arg Arg Met Glu Ala Tyr Cys Tyr Phe
195 200 205

Asp Leu Ser Pro Glu Asp Arg Val Ile His Met Met Gly Arg Pro Asp
210 215 220

Glu Thr Arg His Leu Val Val Ala Asp Gly Glu Ala Val Leu Ser Pro
225 230 235 240

Ala Trp Ser Ile His Met Gly Ala Gly Thr Gly Pro Tyr Ala Phe Val
245 250 255

Trp Gly Met Thr Gly Glu Asn Gln Glu Tyr Asn Asp Val Ala Pro Val
260 265 270

Ala Val Ala Asp Leu Lys
275

<210> SEQ ID NO 10
<211> LENGTH: 274
<212> TYPE: PRT
<213> ORGANISM: Pannonibacter phragmitetus

<400> SEQUENCE: 10

Met Leu Thr Val Glu Thr Arg His Ala Ile Asp Pro Gln Thr Ala Lys
1 5 10 15

-continued

```
Arg Met Asp Thr Glu Glu Leu Arg Lys His Phe His Met Gly Ser Leu
            20                  25                  30

Phe Ala Ala Gly Glu Ile Arg Leu Val Tyr Thr His Tyr Asp Arg Met
        35                  40                  45

Ile Val Gly Ala Ala Val Pro Ser Gly Ala Pro Leu Val Leu Asp Gln
    50                  55                  60

Val Lys Glu Cys Gly Thr Ala Ser Ile Leu Asp Arg Arg Glu Met Ala
65                  70                  75                  80

Val Val Asn Val Gly Ala Ser Gly Lys Val Ser Ala Ala Gly Glu Thr
                85                  90                  95

Tyr Ala Met Glu Arg Gly Asp Val Leu Tyr Leu Pro Leu Gly Ser Gly
            100                 105                 110

Lys Val Thr Phe Glu Gly Glu Gly Arg Phe Tyr Ile Leu Ser Ala Pro
        115                 120                 125

Ala His Ala Ala Tyr Pro Ala Arg Leu Ile Arg Ile Gly Glu Ala Glu
    130                 135                 140

Lys Val Lys Leu Gly Ser Ala Glu Thr Ser Asn Asp Arg Thr Ile Tyr
145                 150                 155                 160

Gln Phe Val His Pro Ala Val Met Thr Ser Cys Gln Leu Val Val Gly
                165                 170                 175

Tyr Thr Gln Leu His Asn Gly Ser Val Trp Asn Thr Met Pro Ala His
            180                 185                 190

Val His Asp Arg Arg Met Glu Ala Tyr Leu Tyr Phe Asp Met Lys Pro
        195                 200                 205

Glu Gln Arg Val Phe His Phe Met Gly Glu Pro Gln Glu Thr Arg His
    210                 215                 220

Leu Val Met Lys Asn Glu Asp Ala Val Val Ser Pro Pro Trp Ser Ile
225                 230                 235                 240

His Cys Gly Ala Gly Thr Gly Ser Tyr Thr Phe Ile Trp Ala Met Ala
                245                 250                 255

Gly Asp Asn Val Asp Tyr Lys Asp Val Glu Met Val Ala Met Glu Asp
            260                 265                 270

Leu Arg


<210> SEQ ID NO 11
<211> LENGTH: 271
<212> TYPE: PRT
<213> ORGANISM: Bacillus subtilis

<400> SEQUENCE: 11

Met Ser Tyr Leu Leu Arg Lys Pro Gln Ser Asn Glu Val Ser Asn Gly
1               5                   10                  15

Val Lys Leu Val His Glu Val Thr Lys Ser Asn Ser Asp Leu Thr Tyr
            20                  25                  30

Val Glu Phe Lys Val Leu Asp Leu Ala Ser Gly Ser Ser Tyr Ala Glu
        35                  40                  45

Glu Leu Lys Lys Gln Glu Ile Cys Ile Val Ala Val Thr Gly Asn Ile
    50                  55                  60

Thr Val Thr Asp His Glu Ser Thr Phe Glu Asn Ile Gly Thr Arg Glu
65                  70                  75                  80

Ser Val Phe Glu Arg Lys Pro Thr Asp Ser Val Tyr Ile Ser Asn Asp
                85                  90                  95

Arg Ser Phe Glu Ile Thr Ala Val Ser Asp Ala Arg Val Ala Leu Cys
            100                 105                 110
```

-continued

```
Tyr Ser Pro Ser Glu Lys Gln Leu Pro Thr Lys Leu Ile Lys Ala Glu
        115                 120                 125

Asp Asn Gly Ile Glu His Arg Gly Lys Phe Ser Asn Lys Arg Thr Val
    130                 135                 140

His Asn Ile Leu Pro Asp Ser Asp Pro Ser Ala Asn Ser Leu Leu Val
145                 150                 155                 160

Val Glu Val Tyr Thr Asp Ser Gly Asn Trp Ser Ser Tyr Pro Pro His
                165                 170                 175

Lys His Asp Gln Asp Asn Leu Pro Glu Glu Ser Phe Leu Glu Glu Thr
            180                 185                 190

Tyr Tyr His Glu Leu Asp Pro Gly Gln Gly Phe Val Phe Gln Arg Val
        195                 200                 205

Tyr Thr Asp Asp Arg Ser Ile Asp Glu Thr Met Thr Val Glu Asn Glu
    210                 215                 220

Asn Val Val Ile Val Pro Ala Gly Tyr His Pro Val Gly Val Pro Asp
225                 230                 235                 240

Gly Tyr Thr Ser Tyr Tyr Leu Asn Val Met Ala Gly Pro Thr Arg Lys
                245                 250                 255

Trp Lys Phe His Asn Asp Pro Ala His Glu Trp Ile Leu Glu Arg
            260                 265                 270


<210> SEQ ID NO 12
<211> LENGTH: 269
<212> TYPE: PRT
<213> ORGANISM: Ochrobactrum anthropi

<400> SEQUENCE: 12

Met Ala Asn Leu Leu Arg Lys Pro Asn Gly Thr His Gly Lys Val His
1               5                   10                  15

Asp Ile Thr Pro Glu Asn Ala Lys Trp Gly Tyr Val Gly Phe Gly Leu
            20                  25                  30

Phe Arg Leu Lys Ser Gly Glu Ser Val Ser Glu Lys Thr Gly Ser Thr
        35                  40                  45

Glu Val Ile Leu Val Leu Val Glu Gly Lys Ala Lys Ile Ser Ala Ser
    50                  55                  60

Gly Glu Asp Phe Gly Glu Met Gly Glu Arg Leu Asn Val Phe Glu Lys
65                  70                  75                  80

Leu Pro Pro His Cys Leu Tyr Val Pro Ala Glu Ser Asp Trp His Ala
                85                  90                  95

Thr Ala Thr Thr Asp Cys Val Leu Ala Val Cys Thr Ala Pro Gly Lys
            100                 105                 110

Pro Gly Arg Lys Ala Gln Lys Leu Gly Pro Glu Ser Leu Thr Leu Glu
        115                 120                 125

Gln Arg Gly Lys Gly Ala Asn Thr Arg Phe Ile His Asn Ile Ala Met
    130                 135                 140

Glu Ser Arg Asp Val Ala Asp Ser Leu Leu Val Thr Glu Val Phe Thr
145                 150                 155                 160

Pro Gln Gly Asn Trp Ser Ser Tyr Pro Pro His Arg His Asp Glu Asp
                165                 170                 175

Asn Phe Pro Asp Met Thr Tyr Leu Glu Glu Thr Tyr Tyr His Arg Leu
            180                 185                 190

Asn Pro Ala Gln Gly Phe Gly Phe Gln Arg Val Phe Thr Glu Asp Gly
        195                 200                 205

Ser Leu Asp Glu Thr Met Ala Val Ser Asp Gly Asp Val Val Leu Val
    210                 215                 220
```

```
Pro Lys Gly His His Pro Cys Gly Ala Pro Tyr Gly Tyr Glu Met Tyr
225                 230                 235                 240

Tyr Leu Asn Val Met Ala Gly Pro Leu Arg Lys Trp Arg Phe Lys Asn
                245                 250                 255

His Pro Asp His Asp Trp Ile Phe Lys Arg Asp Asn Pro
            260                 265


<210> SEQ ID NO 13
<211> LENGTH: 268
<212> TYPE: PRT
<213> ORGANISM: Halomonas titanicae

<400> SEQUENCE: 13

Met Ala Ser Leu Leu Val Arg Pro Thr Ala Pro Asp Ala Gln Gly Thr
1               5                   10                  15

Val Ile Asp Val Thr Pro Glu Ser Ala Gly Trp Thr His Val Gly Phe
            20                  25                  30

Arg Val His Lys Leu Ala Lys Gly Gln Arg Leu Glu Ala Ser Ser Asp
        35                  40                  45

Asp Gln Glu Val Cys Leu Val Leu Leu Thr Gly Arg Ala Thr Val Thr
    50                  55                  60

Cys Gly Glu His Arg Phe Glu Asp Ile Gly Gln Arg Met Asp Ile Phe
65                  70                  75                  80

Glu Gln Ile Pro Pro Tyr Ala Val Tyr Leu Pro Asp His Val Ser Tyr
                85                  90                  95

Ala Val Glu Ala Thr Thr Asp Leu Glu Leu Ala Val Cys Thr Ala Pro
            100                 105                 110

Gly His Gly Asn His Ala Pro Arg Leu Ile Ala Pro Asp Asn Ile Lys
        115                 120                 125

Gln Ser Thr Arg Gly Gln Gly Thr Asn Thr Arg His Val His Asp Ile
    130                 135                 140

Leu Pro Glu Thr Glu Pro Ala Asp Ser Leu Leu Val Val Glu Val Phe
145                 150                 155                 160

Thr Pro Ala Gly Asn Trp Ser Ser Tyr Pro Pro His Lys His Asp Val
                165                 170                 175

Asp Asn Leu Pro His Glu Ser His Leu Glu Glu Thr Tyr Tyr His Arg
            180                 185                 190

Ile Asn Pro Glu Gln Gly Phe Ala Phe Gln Arg Val Tyr Thr Asp Asp
        195                 200                 205

Arg Ser Leu Asp Glu Thr Met Ala Val Glu Asn Gly Cys Cys Val Leu
    210                 215                 220

Val Pro Lys Gly Tyr His Pro Val Gly Ala Ser His Gly Tyr Ser Leu
225                 230                 235                 240

Tyr Tyr Leu Asn Val Met Ala Gly Pro Lys Arg Ala Trp Lys Phe His
                245                 250                 255

Asn Asp Pro Asp His Glu Trp Leu Met Asn Ala Gly
            260                 265


<210> SEQ ID NO 14
<211> LENGTH: 264
<212> TYPE: PRT
<213> ORGANISM: Acidiphilium multivorum

<400> SEQUENCE: 14

Met Pro Asp Leu Leu Arg Lys Pro Phe Gly Thr His Gly Lys Val His
1               5                   10                  15
```

```
Asp Ile Thr Pro Ala Ala Ala Gly Trp Arg His Val Gly Phe Gly Leu
            20                  25                  30

Tyr Arg Leu Arg Ala Gly Glu Phe Ala Ala Glu Ala Thr Gly Gly Asn
        35                  40                  45

Glu Val Ile Leu Val Met Val Glu Gly Lys Ala Ser Ile Arg Ala Ala
    50                  55                  60

Gly Arg Asp Trp Gly Val Leu Gly Glu Arg Met Ser Val Phe Glu Lys
65                  70                  75                  80

Ser Pro Pro His Ser Leu Tyr Val Pro Asn Gly Ala Glu Trp Ala Leu
                85                  90                  95

Val Ala Glu Thr Asp Cys Ile Val Ala Val Cys Ser Ala Pro Gly Arg
            100                 105                 110

Gly Gly His Ala Ala Arg Arg Ile Gly Pro Glu Gly Ile Val Leu Thr
        115                 120                 125

Ala Arg Gly Glu Gly Thr Asn Thr Arg His Ile Asn Asn Ile Ala Met
    130                 135                 140

Glu Ala Glu Asp Tyr Cys Asp Ala Leu Leu Val Thr Glu Val Phe Thr
145                 150                 155                 160

Pro Ala Gly His Trp Ser Ser Tyr Pro Ser His Arg His Asp Glu Asp
                165                 170                 175

Asp Asp Pro Arg Ile Thr Tyr Leu Glu Glu Thr Tyr Tyr His Arg Leu
            180                 185                 190

Asn Pro Ala Ser Gly Phe Gly Val Gln Arg Val Tyr Thr Asp Asp Arg
        195                 200                 205

Ala Leu Asp Gln Thr Met Ala Val Ser Asp Gly Asp Val Val Leu Val
    210                 215                 220

Pro Arg Gly His His Pro Cys Ala Ala Pro Tyr Gly Ile Glu Met Tyr
225                 230                 235                 240

Tyr Leu Asn Val Met Ala Gly Pro Leu Arg Lys Trp Arg Phe Leu Pro
                245                 250                 255

Asp Pro Glu Leu Gly Ile Ala Lys
            260


<210> SEQ ID NO 15
<211> LENGTH: 271
<212> TYPE: PRT
<213> ORGANISM: Lactobacillus casei

<400> SEQUENCE: 15

Met Ser Leu Leu Tyr His Lys Gln Asn Gln Glu Leu Ser Ser Gly Val
1               5                   10                  15

Arg Leu Ile Gln Asp Val Asn Ala Ser Asn Ser Pro Met Lys Tyr Thr
            20                  25                  30

Ala Val Lys Val Leu Glu Phe Ser Ala Asp Ser Ser Tyr Glu Glu Thr
        35                  40                  45

Leu Glu Ala Phe Glu Ala Gly Ile Val Val Leu Glu Gly Lys Val Thr
    50                  55                  60

Ile Thr Ala Asp Asp Gln Thr Phe Glu Asp Val Gly Gln Arg Thr Ser
65                  70                  75                  80

Ile Phe Asp Lys Ile Pro Thr Asp Ser Val Tyr Val Ser Thr Gly Leu
                85                  90                  95

Ala Phe Gly Ile Arg Ala Lys Gln Ala Ala Lys Ile Leu Ile Ala Tyr
            100                 105                 110

Ala Pro Thr Asn Gln Thr Phe Pro Val Arg Leu Ile Arg Gly Asn Ile
```

-continued

```
        115                 120                 125

His Gln Val Glu His Arg Gly Lys Tyr Asn Asn Lys Arg Leu Val Gln
    130                 135                 140

Asn Ile Leu Pro Asp Asn Leu Pro Phe Ala Asp Lys Leu Leu Leu Val
145                 150                 155                 160

Glu Val Tyr Thr Asp Ser Ala Asn Trp Ser Ser Tyr Pro Pro His Arg
                165                 170                 175

His Asp His Asp Asp Leu Pro Ala Glu Ser Leu Leu Glu Glu Ile Tyr
            180                 185                 190

Tyr His Glu Met Arg Pro Lys Gln Gly Phe Val Phe Gln Arg Val Tyr
        195                 200                 205

Thr Asp Asp Leu Ser Leu Asp Glu Thr Met Ala Val Gln Asn Gln Asp
    210                 215                 220

Val Val Val Val Pro Lys Gly Tyr His Pro Val Gly Val Pro Asp Gly
225                 230                 235                 240

Tyr Asp Ser Tyr Tyr Leu Asn Val Met Ala Gly Pro Thr Arg Val Trp
                245                 250                 255

His Phe His Asn Ala Pro Glu His Ala Trp Ile Ile Asp Arg Gln
            260                 265                 270


<210> SEQ ID NO 16
<211> LENGTH: 466
<212> TYPE: PRT
<213> ORGANISM: Bacteroides sp.

<400> SEQUENCE: 16

Met Lys Lys Phe Met Asp Glu Asn Phe Leu Leu Gln Thr Glu Thr Ala
1               5                   10                  15

Gln Lys Leu Tyr His Asn His Ala Ala Asn Met Pro Ile Phe Asp Tyr
            20                  25                  30

His Cys His Ile Asn Pro Lys Asp Ile Ala Glu Asp Arg Met Phe Lys
        35                  40                  45

Thr Ile Thr Glu Ile Trp Leu Tyr Gly Asp His Tyr Lys Trp Arg Ala
    50                  55                  60

Met Arg Thr Asn Gly Val Asp Glu Arg Phe Cys Thr Gly Asp Ala Ser
65                  70                  75                  80

Asp Trp Glu Lys Phe Glu Lys Trp Ala Glu Thr Val Pro His Thr Leu
                85                  90                  95

Arg Asn Pro Leu Tyr His Trp Thr His Leu Glu Leu Lys Lys Phe Phe
            100                 105                 110

Gly Ile Asn Glu Ile Leu Ser Pro Lys Asn Ala Arg Glu Ile Tyr Asp
        115                 120                 125

Ala Cys Asn Glu Lys Leu Gln Thr Pro Ala Tyr Ser Cys Arg Asn Ile
    130                 135                 140

Ile Arg Met Ala Asn Val His Thr Ile Cys Thr Thr Asp Asp Pro Val
145                 150                 155                 160

Asp Thr Leu Glu Tyr His Gln Gln Ile Lys Glu Asp Gly Phe Glu Val
                165                 170                 175

Ala Val Leu Pro Ala Trp Arg Pro Asp Lys Ala Met Met Val Glu Asp
            180                 185                 190

Pro Lys Phe Phe Asn Asp Tyr Met Asp Gln Leu Ala Glu Ala Ala Gly
        195                 200                 205

Ile His Ile Glu Ser Phe Glu Asp Leu Met Glu Ala Leu Asp Thr Arg
    210                 215                 220
```

-continued

```
His Gln Tyr Phe His Asp Asn Gly Cys Arg Leu Ser Asp His Gly Leu
225                 230                 235                 240

Asp Thr Val Phe Ala Glu Asp Tyr Thr Glu Glu Glu Ile Lys Ala Ile
                245                 250                 255

Phe Lys Lys Ile Arg Gly Gly Ser Arg Leu Ser Glu Thr Glu Ile Leu
            260                 265                 270

Lys Phe Lys Ser Cys Met Leu Tyr Glu Tyr Gly Val Met Asp His Ser
        275                 280                 285

Arg Gly Trp Thr Gln Gln Leu His Ile Gly Ala Gln Arg Asn Asn Asn
    290                 295                 300

Thr Arg Leu Phe Lys Lys Leu Gly Pro Asp Thr Gly Phe Asp Ser Ile
305                 310                 315                 320

Gly Asp Lys Pro Ile Ala Glu Pro Leu Ala Lys Leu Leu Asp Arg Leu
                325                 330                 335

Asp Gln Glu Asn Lys Leu Cys Lys Thr Val Leu Tyr Asn Leu Asn Pro
            340                 345                 350

Arg Asp Asn Glu Leu Tyr Ala Thr Met Leu Gly Asn Phe Gln Asp Gly
        355                 360                 365

Ser Val Pro Gly Lys Ile Gln Tyr Gly Ser Gly Trp Trp Phe Leu Asp
    370                 375                 380

Gln Lys Asp Gly Met Ile Lys Gln Met Asn Ala Leu Ser Asn Leu Gly
385                 390                 395                 400

Leu Leu Ser Arg Phe Val Gly Met Leu Thr Asp Ser Arg Ser Phe Leu
                405                 410                 415

Ser Tyr Thr Arg His Glu Tyr Phe Arg Arg Thr Leu Cys Asn Leu Leu
            420                 425                 430

Gly Asn Asp Val Glu Asn Gly Glu Ile Pro Ala Asp Met Glu Leu Leu
        435                 440                 445

Gly Ser Met Val Glu Asn Ile Cys Phe Asn Asn Ala Lys Asn Tyr Phe
    450                 455                 460

Asn Phe
465


<210> SEQ ID NO 17
<211> LENGTH: 451
<212> TYPE: PRT
<213> ORGANISM: Thermotoga maritima MSB8

<400> SEQUENCE: 17

Met Phe Leu Gly Glu Asp Tyr Leu Leu Thr Asn Arg Ala Ala Val Arg
1               5                   10                  15

Leu Phe Asn Glu Val Lys Asp Leu Pro Ile Val Asp Pro His Asn His
            20                  25                  30

Leu Asp Ala Lys Asp Ile Val Glu Asn Lys Pro Trp Asn Asp Ile Trp
        35                  40                  45

Glu Val Glu Gly Ala Thr Asp His Tyr Val Trp Glu Leu Met Arg Arg
    50                  55                  60

Cys Gly Val Ser Glu Glu Tyr Ile Thr Gly Ser Arg Ser Asn Lys Glu
65                  70                  75                  80

Lys Trp Leu Ala Leu Ala Lys Val Phe Pro Arg Phe Val Gly Asn Pro
                85                  90                  95

Thr Tyr Glu Trp Ile His Leu Asp Leu Trp Arg Arg Phe Asn Ile Lys
            100                 105                 110

Lys Val Ile Ser Glu Glu Thr Ala Glu Glu Ile Trp Glu Glu Thr Lys
        115                 120                 125
```

-continued

Lys Lys Leu Pro Glu Met Thr Pro Gln Lys Leu Leu Arg Asp Met Lys
130 135 140

Val Glu Ile Leu Cys Thr Thr Asp Asp Pro Val Ser Thr Leu Glu His
145 150 155 160

His Arg Lys Ala Lys Glu Ala Val Glu Gly Val Thr Ile Leu Pro Thr
165 170 175

Trp Arg Pro Asp Arg Ala Met Asn Val Asp Lys Glu Gly Trp Arg Glu
180 185 190

Tyr Val Glu Lys Met Gly Glu Arg Tyr Gly Glu Asp Thr Ser Thr Leu
195 200 205

Asp Gly Phe Leu Asn Ala Leu Trp Lys Ser His Glu His Phe Lys Glu
210 215 220

His Gly Cys Val Ala Ser Asp His Ala Leu Leu Glu Pro Ser Val Tyr
225 230 235 240

Tyr Val Asp Glu Asn Arg Ala Arg Ala Val His Glu Lys Ala Phe Ser
245 250 255

Gly Glu Lys Leu Thr Gln Asp Glu Ile Asn Asp Tyr Lys Ala Phe Met
260 265 270

Met Val Gln Phe Gly Lys Met Asn Gln Glu Thr Asn Trp Val Thr Gln
275 280 285

Leu His Ile Gly Ala Leu Arg Asp Tyr Arg Asp Ser Leu Phe Lys Thr
290 295 300

Leu Gly Pro Asp Ser Gly Gly Asp Ile Ser Thr Asn Phe Leu Arg Ile
305 310 315 320

Ala Glu Gly Leu Arg Tyr Phe Leu Asn Glu Phe Asp Gly Lys Leu Lys
325 330 335

Ile Val Leu Tyr Val Leu Asp Pro Thr His Leu Pro Thr Ile Ser Thr
340 345 350

Ile Ala Arg Ala Phe Pro Asn Val Tyr Val Gly Ala Pro Trp Trp Phe
355 360 365

Asn Asp Ser Pro Phe Gly Met Glu Met His Leu Lys Tyr Leu Ala Ser
370 375 380

Val Asp Leu Leu Tyr Asn Leu Ala Gly Met Val Thr Asp Ser Arg Lys
385 390 395 400

Leu Leu Ser Phe Gly Ser Arg Thr Glu Met Phe Arg Arg Val Leu Ser
405 410 415

Asn Val Val Gly Glu Met Val Glu Lys Gly Gln Ile Pro Ile Lys Glu
420 425 430

Ala Arg Glu Leu Val Lys His Val Ser Tyr Asp Gly Pro Lys Ala Leu
435 440 445

Phe Phe Gly
450

<210> SEQ ID NO 18
<211> LENGTH: 427
<212> TYPE: PRT
<213> ORGANISM: Bacillus halodurans

<400> SEQUENCE: 18

Met Ser Ile Asn Ser Arg Glu Val Leu Ala Glu Lys Val Lys Asn Ala
1 5 10 15

Val Asn Asn Gln Pro Val Thr Asp Met His Thr His Leu Phe Ser Pro
20 25 30

Asn Phe Gly Glu Ile Leu Leu Trp Asp Ile Asp Glu Leu Leu Thr Tyr

```
        35                  40                  45

His Tyr Leu Val Ala Glu Val Met Arg Trp Thr Asp Val Ser Ile Glu
    50                  55                  60

Ala Phe Trp Ala Met Ser Lys Arg Glu Gln Ala Asp Leu Ile Trp Glu
65                  70                  75                  80

Glu Leu Phe Ile Lys Arg Ser Pro Val Ser Glu Ala Cys Arg Gly Val
                85                  90                  95

Leu Thr Cys Leu Gln Gly Leu Gly Leu Asp Pro Ala Thr Arg Asp Leu
            100                 105                 110

Gln Val Tyr Arg Glu Tyr Phe Ala Lys Lys Thr Ser Glu Glu Gln Val
        115                 120                 125

Asp Thr Val Leu Gln Leu Ala Asn Val Ser Asp Val Val Met Thr Asn
    130                 135                 140

Asp Pro Phe Asp Asp Asn Glu Arg Ile Ser Trp Leu Glu Gly Lys Gln
145                 150                 155                 160

Pro Asp Ser Arg Phe His Ala Ala Leu Arg Leu Asp Pro Leu Leu Asn
                165                 170                 175

Glu Tyr Glu Gln Thr Lys His Arg Leu Arg Asp Trp Gly Tyr Lys Val
            180                 185                 190

Asn Asp Glu Trp Asn Glu Gly Ser Ile Gln Glu Val Lys Arg Phe Leu
        195                 200                 205

Thr Asp Trp Ile Glu Arg Met Asp Pro Val Tyr Met Ala Val Ser Leu
    210                 215                 220

Pro Pro Thr Phe Ser Phe Pro Glu Glu Ser Asn Arg Gly Arg Ile Ile
225                 230                 235                 240

Arg Asp Cys Leu Leu Pro Val Ala Glu Lys His Asn Ile Pro Phe Ala
                245                 250                 255

Met Met Ile Gly Val Lys Lys Arg Val His Pro Ala Leu Gly Asp Ala
            260                 265                 270

Gly Asp Phe Val Gly Lys Ala Ser Met Asp Gly Val Glu His Leu Leu
        275                 280                 285

Arg Glu Tyr Pro Asn Asn Lys Phe Leu Val Thr Met Leu Ser Arg Glu
    290                 295                 300

Asn Gln His Glu Leu Val Val Leu Ala Arg Lys Phe Ser Asn Leu Met
305                 310                 315                 320

Ile Phe Gly Cys Trp Trp Phe Met Asn Asn Pro Glu Ile Ile Asn Glu
                325                 330                 335

Met Thr Arg Met Arg Met Glu Met Leu Gly Thr Ser Phe Ile Pro Gln
            340                 345                 350

His Ser Asp Ala Arg Val Leu Glu Gln Leu Ile Tyr Lys Trp His His
        355                 360                 365

Ser Lys Ser Ile Ile Ala Glu Val Leu Ile Asp Lys Tyr Asp Asp Ile
    370                 375                 380

Leu Gln Ala Gly Trp Glu Val Thr Glu Glu Glu Ile Lys Arg Asp Val
385                 390                 395                 400

Ala Asp Leu Phe Ser Arg Asn Phe Trp Arg Phe Val Gly Arg Asn Asp
                405                 410                 415

His Val Thr Ser Val Lys Val Glu Gln Gln Thr
            420                 425


<210> SEQ ID NO 19
<211> LENGTH: 473
<212> TYPE: PRT
<213> ORGANISM: Bacillus subtilis
```

-continued

<400> SEQUENCE: 19

```
Met Glu Pro Phe Met Gly Lys Asn Phe Leu Leu Lys Asn Glu Thr Ala
1               5                   10                  15

Val Ser Leu Tyr His Asn Tyr Ala Lys Asp Met Pro Ile Ile Asp Tyr
            20                  25                  30

His Cys His Leu Ser Pro Lys Glu Ile Tyr Glu Asn Lys Thr Phe Gln
        35                  40                  45

Asn Ile Thr Glu Ala Trp Leu Tyr Gly Asp His Tyr Lys Trp Arg Ile
    50                  55                  60

Met Arg Ala Asn Gly Ile Glu Glu Thr Tyr Ile Thr Gly Asp Ala Pro
65                  70                  75                  80

Asp Glu Glu Lys Phe Met Ala Trp Ala Lys Thr Val Pro Met Ala Ile
                85                  90                  95

Gly Asn Pro Leu Tyr Asn Trp Thr His Leu Glu Leu Gln Arg Phe Phe
            100                 105                 110

Gly Ile Tyr Glu Ile Leu Asn Glu Lys Ser Gly Ser Ala Ile Trp Lys
        115                 120                 125

Gln Thr Asn Lys Leu Leu Lys Gly Glu Gly Phe Gly Ala Arg Asp Leu
    130                 135                 140

Ile Val Lys Ser Asn Val Lys Val Val Cys Thr Thr Asp Asp Pro Val
145                 150                 155                 160

Asp Ser Leu Glu Tyr His Leu Leu Leu Lys Glu Asp Lys Asp Phe Pro
                165                 170                 175

Val Ser Val Leu Pro Gly Phe Arg Pro Asp Lys Gly Leu Glu Ile Asn
            180                 185                 190

Arg Glu Gly Phe Pro Glu Trp Val Gln Ala Leu Glu Asp Ala Ala Ala
        195                 200                 205

Ile Ser Ile Thr Thr Tyr Asp Glu Phe Leu Lys Ala Leu Glu Lys Arg
    210                 215                 220

Val Arg Phe Phe His Ser Ala Gly Gly Arg Val Ser Asp His Ala Ile
225                 230                 235                 240

Asp Thr Met Val Phe Ala Glu Thr Thr Lys Glu Glu Ala Gly Arg Ile
                245                 250                 255

Phe Ser Asp Arg Leu Gln Gly Thr Glu Val Ser Cys Glu Asp Glu Lys
            260                 265                 270

Lys Phe Lys Thr Tyr Thr Leu Gln Phe Leu Cys Gly Leu Tyr Ala Glu
        275                 280                 285

Leu Asp Trp Ala Met Gln Phe His Ile Asn Ala Leu Arg Asn Thr Asn
    290                 295                 300

Thr Lys Met Met Lys Arg Leu Gly Pro Asp Thr Gly Tyr Asp Ser Met
305                 310                 315                 320

Asn Asp Glu Glu Ile Ala Lys Pro Leu Tyr Lys Leu Leu Asn Ser Val
                325                 330                 335

Glu Met Lys Asn Gln Leu Pro Lys Thr Ile Leu Tyr Ser Leu Asn Pro
            340                 345                 350

Asn Asp Asn Tyr Val Ile Ala Ser Met Ile Asn Ser Phe Gln Asp Gly
        355                 360                 365

Ile Thr Pro Gly Lys Ile Gln Phe Gly Thr Ala Trp Trp Phe Asn Asp
    370                 375                 380

Thr Lys Asp Gly Met Leu Asp Gln Met Lys Ala Leu Ser Asn Val Gly
385                 390                 395                 400

Leu Phe Ser Arg Phe Ile Gly Met Leu Thr Asp Ser Arg Ser Phe Leu
```

-continued

```
                405                 410                 415

Ser Tyr Thr Arg His Glu Tyr Phe Arg Arg Ile Val Cys Asn Leu Ile
            420                 425                 430

Gly Glu Trp Val Glu Asn Gly Glu Val Pro Arg Asp Met Glu Leu Leu
        435                 440                 445

Gly Ser Ile Val Gln Gly Ile Cys Tyr Asp Asn Ala Lys His Tyr Phe
    450                 455                 460

Gln Phe Gln Glu Glu Lys Ala Asn Val
465                 470
```

<210> SEQ ID NO 20
<211> LENGTH: 825
<212> TYPE: DNA
<213> ORGANISM: Rhizobium sp.

<400> SEQUENCE: 20

```
atgctcaacg tggaaacgag gcacgccgtt cacgcggatc acgcgagatc actcgacaca     60

gagggcctgc gccggcactt cctggcccag ggcctgtttg cggagggcga gatacggctg    120

atctatacgc attatgatcg attcgtcatg ggaggcgccg tgccggacgg cgcgccactt    180

gtgctcgatc atgtcgagga gacgaaaacg ccgggctttc tcgaccgacg ggagatggga    240

atcgtcaata tcggtgctga gggcagcgtg catgccggca acgaaagctg gtcgctgaac    300

cgtggtgacg tactttatct cggcatgggg gcgggaccgg tcaccttcga aggggctggg    360

cgcttctacc tcgtctcggc accggcgcat cgcagcctgc ccaaccggct cgtcacgccg    420

gccgacagca aggaggtcaa gcttggcgct ctcgagactt ccaacaaacg caccatcaat    480

cagttcattc atcccctggt catggaaagc tgccagctcg tgctgggata taccacgctg    540

gaggacggct cggtctggaa taccatgccc gcgcatgtgc acgaccgacg catggaggcc    600

tatctctatt tcggcatgga tgagacatcg cgggttctgc atctgatggg cgagccgcag    660

caaacgaggc atctcttcgt cgccaatgag gaaggggcga tctctccgcc gtggtccatc    720

catgcgggag caggcattgg cagctatacc ttcatctggg ccatggcggg cgacaatgtc    780

gattataccg acatggagtt catccagccg ggagatcttc gatga                    825
```

<210> SEQ ID NO 21
<211> LENGTH: 837
<212> TYPE: DNA
<213> ORGANISM: Escherichia coli

<400> SEQUENCE: 21

```
atggacgtaa gacagagcat ccacagtgcg cacgcaaaaa cgctggatac ccaagggctg     60

cgcaatgaat ttttggttga aaaggtattt gtcgccgatg agtacaccat ggtttacagc    120

cacattgacc gaattattgt tggcggcatt atgccgataa ctaaaacggt ttccgttggc    180

ggggaagttg gtaaacaact cggcgtaagc tatttccttg aacgtcgcga gttaggtgtt    240

atcaatattg gcggtgccgg tacgattact gtcgatggcc aatgctatga aatcggtcac    300

cgcgacgccc tgtatgttgg taaaggtgca aaagaagttg tctttgccag tattgatacc    360

ggcactccgg cgaagtttta ttacaattgc gcacccgcgc atacgacgta tcccaccaaa    420

aaagtcacac cggacgaagt atctccagtc acgttaggcg ataacctcac cagtaaccgt    480

cgcacgatta acaaatattt tgtcccggat gtactggaaa cctgccaatt gagtatgggg    540

ctgacggagc tggctccggg taacttgtgg aacaccatgc cgtgtcacac ccacgagcgc    600

cggatggaag tttatttcta tttcaatatg gatgatgacg cctgcgtttt ccacatgatg    660
```

```
gggcagccgc aagaaacgcg tcatattgtg atgcataacg agcaggcggt gatctccccg    720

agctggtcga tccattccgg tgtcggaacc aaagcttata cctttatctg gggcatggtc    780

ggtgaaaacc aggtctttga tgatatggac catgtggccg ttaaagattt gcgctag       837


<210> SEQ ID NO 22
<211> LENGTH: 837
<212> TYPE: DNA
<213> ORGANISM: Rhizobium sp.

<400> SEQUENCE: 22

atgacgatga agatactcta cggcgccgga ccggaggatg tgaaagggta tgacacgcag     60

cgcctgcgcg acgccttcct gctggacgac ctcttcgccg acgaccgggt cagtttcaca    120

tatacccatg tcgatcgcct catcctcggc ggggccgtcc cggtgacgac gagcctcacc    180

ttcggctccg gcacggagat cggaacgccc tacctgcttt ccgcccgcga gatggggatc    240

gccaatctcg gcggcacggg cacgatcgag gtggatggcc agcgcttcac gctcgaaaac    300

cgcgacgtgc tctatgtcgg tcgcggcgcc cggcagatga ccgcctccag cctgtcggcg    360

gagaggccag cccgcttcta catgaattcc gtgcccgccg gcgccgattt cccgcaccgt    420

ctgatcaccc gcggagaggc caagcccctc gatctcggcg atgcgcgccg ctcgaacagg    480

cgccggctcg caatgtacat ccatccggag gtctcgccgt cctgcctgct gctcatgggc    540

atcaccgatc ttgccgaggg cagcgcctgg aacaccatgc cgccgcatct gcacgagcgg    600

cggatggagg cctattgcta cttcgatctc tcgcccgagg accgggtcat ccacatgatg    660

ggtcggccgg acgaaacccg ccaccttgtc gtggccgacg gcgaggcggt cctctctccc    720

gcctggtcga tccatatggg tgccgggacg gggccctacg ccttcgtctg gggcatgacc    780

ggcgaaaacc aggaatacaa cgacgtcgct cccgtagccg tggctgatct caaatga       837


<210> SEQ ID NO 23
<211> LENGTH: 825
<212> TYPE: DNA
<213> ORGANISM: Pannonibacter phragmitetus

<400> SEQUENCE: 23

atgctgaccg tcgaaacccg ccacgccatt gatccgcaga ccgcaaagcg gatggacacg     60

gaagagctgc gcaagcattt ccacatgggc agcctgtttg ctgccggtga aatccgcctc    120

gtctacaccc actatgaccg catgatcgtc ggcgctgccg tgccctcggg cgcgccgctg    180

gtgctggatc aggtcaagga atgcggcacc gccagcatcc tcgaccgccg cgagatggct    240

gtcgtcaacg tcggcgccag cggcaaggtc tctgcagcag gcgaaaccta cgccatggaa    300

cgcggcgacg tgctctatct gccgctgggc tccggcaagg tgaccttcga aggcgaaggc    360

cgcttctaca ttctctccgc tccggcccac gctgcttacc cggcccgcct gatccgcatc    420

ggcgaggccg agaaggtcaa gctcggctcg gccgagacct ccaacgaccg caccatctac    480

cagttcgtgc atccggcggt gatgacttcc tgccaactcg tcgtcggcta cacccagctg    540

cacaacggct ctgtctggaa caccatgccc gcccacgtgc atgaccggcg catggaggcc    600

tatctctatt tcgacatgaa gccggagcag cgcgtgttcc acttcatggg cgagccgcag    660

gaaacccgcc atctggtcat gaagaacgag gatgcggtgg tctccccgcc ctggtccatc    720

cactgcggcg caggcaccgg cagctacacc ttcatctggg ccatggccgg cgacaacgtc    780

gactacaagg acgtggaaat ggtcgccatg gaggatctgc ggtga                    825
```

<210> SEQ ID NO 24
<211> LENGTH: 816
<212> TYPE: DNA
<213> ORGANISM: Bacillus subtilis

<400> SEQUENCE: 24
atgagttatt tgttgcgtaa gccgcagtcg aatgaagtgt ctaatggggt caaactggtg 60
cacgaagtaa cgaaatccaa ctctgatctc acctatgtag agtttaaagt gttagatctc 120
gcttccggtt ccagctatgc agaagaattg aaaaaacagg aaatctgtat tgtcgcggta 180
acgggaaaca ttacagtgac cgatcacgag tcgacttttg agaatatcgg cacgcgtgaa 240
agcgtattcg aacgaaaacc gacagacagc gtctatattt caaatgaccg ttcctttgag 300
atcacagcgg tcagcgacgc aagagtggcg ctttgctatt ctccatcgga aaaacagctt 360
ccgacaaagc tgatcaaagc ggaagacaat ggcattgagc atcgcgggaa gttttcaaac 420
aaacgtactg ttcacaacat tcttccggat tcagaccctt cagctaacag cctattagta 480
gttgaagtct atacagacag cggcaactgg tccagctatc cgcctcataa acatgatcaa 540
gacaatttgc cggaggaatc ttttttagaa gaaacgtact accatgagtt agacccggga 600
cagggctttg tgtttcagcg tgtatacaca gatgaccgct cgattgacga gacaatgact 660
gtagaaaatg aaaacgttgt catcgttcct gcaggatacc acccggtagg cgtgccggac 720
ggatacacat cctactattt aaatgtcatg gcagggccga cgcggaaatg gaagtttcat 780
aatgacccgg cgcatgagtg gattttagaa cgttaa 816

<210> SEQ ID NO 25
<211> LENGTH: 810
<212> TYPE: DNA
<213> ORGANISM: Ochrobactrum anthropi

<400> SEQUENCE: 25
atggccaatt tgttgcgcaa gcccaacggc acgcatggca aggtccacga catcactccg 60
gaaaacgcca aatggggtta tgtcgggttc gggctctttc gtctcaaatc cggcgagagt 120
gtctccgaaa agaccggatc gacggaggtg atccttgttc ttgtggaagg caaggcaaag 180
atttccgctt ctggcgagga tttcggcgag atgggtgaac gcttaaacgt gttcgagaaa 240
ctgccgccac actgcctcta tgtgcctgct gaaagcgact ggcatgcaac cgccacgaca 300
gattgtgttc tggctgtttg caccgcaccg ggcaagccag gccgcaaggc acagaagctt 360
gggccggaaa gcttgacact tgaacaacgc ggaaaaggtg ccaatacccg ctttatccat 420
aatatcgcaa tggaaagccg cgatgttgcc gatagccttc ttgttaccga ggtattcaca 480
ccgcagggaa actggtcgtc ctatccaccc cacagacacg acgaagacaa ttttccggat 540
atgacctatc tggaagagac ctattatcac cgtctcaacc cggcgcaggg cttcggcttc 600
cagcgtgttt tcaccgaaga cggaagcctt gatgaaacca tggcggtctc tgacggagac 660
gtcgtgcttg taccaaaagg ccaccatcca tgtggcgcgc cctatggcta cgagatgtat 720
tatctcaatg tgatggccgg tcccttgcgc aaatggcgct tcaagaacca tcccgaccat 780
gactggattt tcaaacgcga caatccgtaa 810

<210> SEQ ID NO 26
<211> LENGTH: 807
<212> TYPE: DNA
<213> ORGANISM: Halomonas titanicae

<400> SEQUENCE: 26

```
atggcttccc tactggtacg ccccaccgcc ccagatgccc agggcaccgt gattgacgtt     60

acccctgaat ctgctggctg gacgcacgtt ggctttcggg tgcataaact cgccaagggc    120

cagcgcctgg aggccagcag cgatgatcag gaagtctgcc tggtgctgct caccggtcgc    180

gccacggtaa cttgcggcga gcaccgcttt gaagatattg gccagcgtat ggatattttt    240

gagcagatcc ctccctatgc ggtttaccta cctgaccatg ttagctacgc ggtggaagcg    300

accacagact tagagctagc ggtgtgcacc gcccctgggc atggcaacca tgccccacgg    360

ctcatcgcgc ctgacaacat caagcaaagc acccgtggcc agggcaccaa cacccgccat    420

gttcacgata ttctgccgga aaccgagccc gccgatagcc tattagtagt cgaagtattc    480

acacctgcgg gtaactggtc gagctacccg ccccacaaac acgatgtgga taacttaccc    540

cacgaatcac atctggaaga gacctactac caccgcatta accctgaaca agggttcgcc    600

ttccagcgcg tttacaccga tgaccgcagc cttgatgaaa ccatggcggt ggaaaacggc    660

tgctgtgtgt tggttcccaa gggttaccat ccggtgggcg cctcccatgg ctactcgctc    720

tactacttaa atgtgatggc ggggcccaag cgggcatgga aatttcacaa cgaccccgac    780

cacgaatggc tgatgaacgc tggatag                                          807
```

<210> SEQ ID NO 27
<211> LENGTH: 795
<212> TYPE: DNA
<213> ORGANISM: Acidiphilium multivorum

<400> SEQUENCE: 27

```
atgccggact tactgagaaa accgtttggc acccatggca aagtgcacga tattacccca     60

gcagcagcag gttggagaca tgttggtttt ggcttatatc gcttaagagc gggcgaattt    120

gcagcagaag cgacaggcgg caatgaagtt attctggtga tggttgaggg caaagcgtct    180

attagagcag caggcagaga ttggggcgtt ttaggcgaac gtatgagcgt cttcgaaaaa    240

agtccaccac attccctgta tgtcccgaat ggtgcagaat gggccttagt agccgaaaca    300

gattgcattg tagcagtgtg tagcgctccg ggtagaggag gtcatgctgc aagaagaatt    360

ggtcctgaag gtattgtgtt aaccgccaga ggtgaaggca ccaatacacg ccacatcaac    420

aacatcgcca tggaagccga agattattgt gatgccctgt tagtcaccga agtgttcacc    480

ccagccggcc attggagctc ttatccatct catcgtcatg atgaagacga cgatccgcgc    540

atcacctatt tagaagagac ctactatcat cgcttaaatc ctgcctcggg ctttggcgtt    600

caacgcgtct ataccgatga tcgcgcctta gatcaaacca tggcggtttc tgatggcgat    660

gttgttttag ttcctcgcgg ccatcatccg tgtgcagccc cgtatggtat tgaaatgtat    720

tacctgaacg tcatggccgg cccgttacgt aaatggcgct tttacctgga tcctgaactt    780

ggcattgcga aataa                                                       795
```

<210> SEQ ID NO 28
<211> LENGTH: 816
<212> TYPE: DNA
<213> ORGANISM: Lactobacillus casei

<400> SEQUENCE: 28

```
atgtctctgc tgtaccacaa gcagaaccag gaactgagta gtggtgtgcg cctgatccaa     60

gatgttaatg ccagcaatag cccgatgaaa tataccgccg tgaaagtgct ggagtttagc    120

gccgatagca gctatgagga aaccttagag gcctttgaag ccggcattgt tgtgttagag    180
```

-continued

```
ggcaaagtga ccatcaccgc cgacgatcaa accttcgaag atgtgggtca aagaacctcg    240
atcttcgaca aaatcccgac cgatagcgtt tatgtgtcta ccggtttagc cttcggtatt    300
cgcgccaaac aagccgccaa aatcttaatc gcgtatgctc cgaccaatca gaccttccca    360
gttcgcttaa ttcgcggcaa tatccaccag gtggaacatc gcggcaagta caacaacaaa    420
cgcttagtgc agaacattct cccggataat ctcccgttcg ccgataaatt actgctggtt    480
gaggtgtaca ccgatagcgc caattggagc tcctatccgc cgcatagaca tgatcacgat    540
gatttaccgg ccgaaagtct gttagaggag atctactatc acgaaatgcg cccgaagcag    600
ggcttcgtct ttcaacgcgt gtataccgat gatctgagtc tggatgagac catggccgtt    660
caaaatcaag atgttgtcgt tgtcccgaaa ggctatcatc cggttggtgt ccccgacggc    720
tatgattcgt attacctgaa cgtgatggcc ggcccgacaa gagtgtggca ttttcataat    780
gctccggaac atgcctggat tattgatcgc cagtaa                             816
```

<210> SEQ ID NO 29
<211> LENGTH: 1401
<212> TYPE: DNA
<213> ORGANISM: Bacteroides sp.

<400> SEQUENCE: 29

```
atgaaaaaat ttatggatga aaattttctg ttgcaaaccg aaacagcgca gaaattgtat     60
cataatcacg cggcaaacat gccgattttc gattaccact gccacattaa ccccaaagac    120
atcgcggaag accggatgtt taaaaccatc accgaaatct ggttgtacgg cgatcattat    180
aaatggcgcg ccatgcgtac aaacggcgtt gacgagcgct tttgcaccgg cgatgcaagc    240
gattgggaaa agtttgaaaa gtgggccgaa acggttcctc ataccctgcg taatccgctt    300
tatcactgga cacacctgga gctaaagaaa tttttcggga ttaacgagat cctgagtccg    360
aaaaatgccc gggaaattta tgatgcctgt aacgaaaaac tgcaaacgcc cgcgtatagt    420
tgccgcaaca tcatccggat ggccaatgtg catacaatct gtaccaccga cgacccggtt    480
gacacactgg aatatcatca gcaaattaaa gaagacggct ttgaagtggc ggttttacct    540
gcctggcgtc cggataaagc gatgatggtg gaagacccga agttctttaa cgactatatg    600
gaccagttgg ccgaagctgc cggtatccat atcgaatcgt ttgaggattt gatggaagcc    660
ttggatacgc gtcaccagta ttttcatgat aatggttgcc gtttgtccga ccacgggctg    720
gataccgttt ttgctgaaga ttatacggag gaagaaatta aagcgatctt caaaaaaatc    780
cgtggcggca gcaggcttag cgaaacggaa atcctgaaat tcaagtcctg catgttgtac    840
gaatatgggg tgatggacca ttcgcgcggc tggacacaac aattgcacat tggcgcacaa    900
cgcaacaaca acacccgttt gttcaaaaaa ttaggtcccg acactggttt cgattcgatt    960
ggcgataagc cgatcgctga accattggcc aaattgctcg accgcctgga tcaggaaaac   1020
aaattgtgca aaacggtttt gtataatctg aatccgcgtg ataacgagtt gtacgctacc   1080
atgttgggca actttcagga cggatcggtt cccgggaaaa ttcaatacgg ctcgggttgg   1140
tggtttctcg atcagaaaga cggcatgatt aaacagatga atgccctttc caatctgggt   1200
ttgctgagcc gtttcgtagg catgctgacc gactcaagga gcttcctttc gtacacccgt   1260
cacgaatatt tccgtcgtac cctttgcaac ctgcttggga atgatgttga aaacggggag   1320
attccggcag atatggagct tttgggcagt atggttgaga atatttgttt taataacgcg   1380
aagaactatt ttaattttta g                                             1401
```

<210> SEQ ID NO 30
<211> LENGTH: 1356
<212> TYPE: DNA
<213> ORGANISM: Thermotoga maritima MSB8

<400> SEQUENCE: 30
atgtttctgg gcgaagacta tctgctgacc aatcgtgcgg cagttcgtct gttcaacgaa 60
gtgaaagatc tgccgatcgt tgatccgcat aaccacctgg atgcgaaaga tatcgtggaa 120
aacaaaccgt ggaacgacat ctgggaagtg gaaggtgcga ccgatcacta tgtgtgggaa 180
ctgatgcgtc gttgtggtgt tagcgaagaa tatattaccg gctctcgtag caacaaagaa 240
aaatggctgg cgctggcgaa agtgtttccg cgttttgtgg gtaatccgac gtacgaatgg 300
atccacctgg atctgtggcg tcgtttcaac atcaaaaaag tcatcagcga agaaaccgcg 360
gaagaaatct gggaagaaac caaaaaaaaa ctgccggaga tgaccccgca gaaactgctg 420
cgcgacatga aagtggaaat cctgtgcacc accgatgatc cggtgtctac cctggaacat 480
caccgtaaag cgaaagaagc cgtggaaggc gtgaccattt taccgacctg gcgtccggat 540
cgtgcaatga atgttgataa agaaggttgg cgtgaatatg ttgaaaaaat gggtgaacgc 600
tatggcgaag ataccagcac cctggatggt tttctgaatg ccctgtggaa aagccacgaa 660
cacttcaaag aacacggctg tgtggcgagc gatcatgcgc tgctggaacc gagcgtgtac 720
tacgtggatg aaaaccgcgc gcgtgcagtt catgaaaaag cattttctgg tgaaaaactg 780
actcaagatg aaatcaacga ctataaagcg ttcatgatgg tgcagttcgg caaaatgaac 840
caggaaacca actgggtgac ccagctgcac attggtgccc tgcgcgatta ccgcgatagc 900
ctgttcaaaa ccctgggccc ggattctggt ggcgatatca gcaccaactt tctgcgtatt 960
gctgaaggtc tgcgttattt tctgaacgaa tttgatggta aactgaaaat tgtgctgtac 1020
gtgctggatc cgacccattt accgaccatt tcgaccattg cacgtgcgtt cccgaacgtg 1080
tatgtgggtg caccgtggtg gttcaacgat agcccgttcg gcatggaaat gcacctgaaa 1140
tacctggcga gcgttgatct gctgtacaat ctggctggta tggttaccga ttcacgtaaa 1200
ttactgagtt ttggttctcg taccgaaatg tttcgtcgcg ttctgtctaa tgtggttggc 1260
gaaatggtgg aaaaaggcca gatcccgatc aaagaagcgc gcgaactggt gaaacacgtg 1320
agctacgacg gcccgaaagc cctgttcttt ggctga 1356

<210> SEQ ID NO 31
<211> LENGTH: 1284
<212> TYPE: DNA
<213> ORGANISM: Bacillus halodurans

<400> SEQUENCE: 31
atgagcatca acagccgtga agttctggcg gaaaaagtga aaaacgcggt gaacaaccag 60
ccggttaccg atatgcatac ccacctgttt agcccgaact ttggcgaaat tctgctgtgg 120
gacatcgatg aactgctgac ctatcactac ctggttgcgg aagttatgcg ttggaccgat 180
gtgagcattg aagcgttttg ggcaatgagc aaacgtgaac aggccgatct gatttgggaa 240
gaactgttca tcaaacgcag cccggtgagc gaagcatgtc gtggcgttct gacctgttta 300
caaggtttag gtctggatcc ggcaactcgt gatttacagg tgtatcgtga atacttcgcc 360
aaaaaaacca gcgaggaaca ggtggatacc gttctgcagc tggcaaatgt gagcgatgtg 420
gtgatgacca atgatccgtt cgatgataat gaacgcatca gctggctgga aggcaaacag 480
ccggatagcc gctttcatgc agcgttacgt ctggatccgc tgctgaatga atatgaacag 540

-continued

```
accaaacatc gtctgcgtga ttggggttat aaagtgaacg acgaatggaa cgaaggcagc    600
atccaggaag tgaaacgctt tctgaccgac tggattgaac gtatggatcc ggtgtatatg    660
gcggtgagct taccgccgac cttcagcttt ccggaagaat cgaaccgtgg ccgcattatc    720
cgtgattgtc tgttaccggt tgcagaaaaa cataacatcc cgtttgcaat gatgattggc    780
gtgaaaaaac gcgtgcatcc ggcgttaggt gatgcaggcg attttgtggg taaagcaagt    840
atggatggcg ttgaacacct gctgcgcgaa tacccgaaca acaaattcct ggtgaccatg    900
ctgagccgcg aaaaccagca cgaactggtg gttctggcgc gtaaatttag taacctgatg    960
atttttggtt gttggtggtt tatgaacaac ccggagatca tcaacgaaat gacccgcatg   1020
cgcatggaaa tgctgggtac cagctttatc ccgcagcaca gcgatgcccg tgttctggaa   1080
cagctgatct ataaatggca ccacagcaaa agcatcatcg cggaagtcct gatcgacaaa   1140
tacgacgaca tcctgcaagc aggttgggaa gttaccgaag aagaaatcaa acgtgatgtg   1200
gcagatctgt ttagccgcaa cttttggcgc tttgtgggcc gtaacgatca cgtgaccagc   1260
gtgaaagtgg aacagcagac ctga                                          1284
```

```
<210> SEQ ID NO 32
<211> LENGTH: 1422
<212> TYPE: DNA
<213> ORGANISM: Bacillus halodurans

<400> SEQUENCE: 32
```

```
atggaaccgt ttatgggcaa aaacttcctg ctgaaaaacg agaccgcggt gagcctgtac     60
cacaactacg cgaaagatat gccgatcatc gactaccatt gccatctgag cccgaaagaa    120
atctacgaga acaaaacctt ccagaacatc accgaagcgt ggctgtacgg cgatcactac    180
aaatggcgca tcatgcgtgc gaatggcatc gaagaaacct atattaccgg tgatgcaccg    240
gacgaagaaa aattcatggc gtgggcgaaa accgtgccga tggccattgg taatccgctg    300
tataactgga cccatctgga actgcaacgt ttttttggca tctacgaaat cctgaacgaa    360
aaaagcggca gcgcgatctg gaaacagacc aacaaactgc tgaaaggcga aggctttggt    420
gcgcgtgatc tgatcgtgaa aagcaacgtt aaagtggtgt gcaccaccga cgatccggtg    480
gattctctgg aataccatct gctgctgaaa gaagacaaag acttcccggt tagcgtttta    540
ccgggttttc gtccggataa aggtctggaa atcaaccgtg aaggctttcc ggaatgggtt    600
caagccctgg aagatgcggc cgcaattagc attacgacct atgatgaatt tctgaaagcg    660
ctggaaaaac gcgtgcgctt cttccatagt gcgggtggtc gtgttagcga tcatgcaatc    720
gataccatgg ttttcgccga aaccaccaaa gaagaagcgg gtcgcatttt tagtgatcgt    780
ctgcaaggca ccgaagttag ctgcgaagac gagaaaaaat tcaaaaccta caccctgcag    840
tttctgtgtg gcctgtatgc cgaactggac tgggcaatgc agtttcacat caacgcgctg    900
cgcaacacca acaccaaaat gatgaaacgc ctgggtccgg ataccggtta tgatagcatg    960
aacgatgaag aaatcgcgaa accgctgtac aaactgctga acagcgtgga aatgaaaaac   1020
caactgccga aaaccatcct gtacagcctg aacccgaacg acaactacgt gatcgcgagc   1080
atgatcaaca gcttccagga tggcatcacc ccgggcaaaa ttcagtttgg caccgcatgg   1140
tggttcaacg ataccaaaga tggtatgctg gatcagatga aagcactgag caatgtgggc   1200
ctgtttagcc gttttattgg catgctgacc gatagccgta gctttctgag ctatacccgt   1260
cacgaatact ttcgccgcat tgtgtgtaac ctgatcggcg aatgggtgga aaacggcgaa   1320
gttccgcgcg atatggaact gctgggtagt attgtgcaag gtatttgcta cgataacgcg   1380
```

aaacattact tccagttcca ggaggaaaaa gcgaacgtgt ga 1422

<210> SEQ ID NO 33
<211> LENGTH: 593
<212> TYPE: PRT
<213> ORGANISM: Achromobacter piechaudii

<400> SEQUENCE: 33

Met Ser Gln Thr Pro Arg Lys Leu Arg Ser Gln Lys Trp Phe Asp Asp
1 5 10 15

Pro Ala His Ala Asp Met Thr Ala Ile Tyr Val Glu Arg Tyr Leu Asn
20 25 30

Tyr Gly Leu Thr Arg Gln Glu Leu Gln Ser Gly Arg Pro Ile Ile Gly
35 40 45

Ile Ala Gln Thr Gly Ser Asp Leu Ala Pro Cys Asn Arg His His Leu
50 55 60

Ala Leu Ala Glu Arg Val Lys Ala Gly Ile Arg Asp Ala Gly Gly Ile
65 70 75 80

Pro Met Glu Phe Pro Val His Pro Leu Ala Glu Gln Gly Arg Arg Pro
85 90 95

Thr Ala Ala Leu Asp Arg Asn Leu Ala Tyr Leu Gly Leu Val Glu Ile
100 105 110

Leu His Gly Tyr Pro Leu Asp Gly Val Val Leu Thr Thr Gly Cys Asp
115 120 125

Lys Thr Thr Pro Ala Cys Leu Met Ala Ala Ala Thr Val Asp Leu Pro
130 135 140

Ala Ile Val Leu Ser Gly Gly Pro Met Leu Asp Gly Trp His Asp Gly
145 150 155 160

Gln Arg Val Gly Ser Gly Thr Val Ile Trp His Ala Arg Asn Leu Met
165 170 175

Ala Ala Gly Lys Leu Asp Tyr Glu Gly Phe Met Thr Leu Ala Thr Ala
180 185 190

Ser Ser Pro Ser Val Gly His Cys Asn Thr Met Gly Thr Ala Leu Ser
195 200 205

Met Asn Ser Leu Ala Glu Ala Leu Gly Met Ser Leu Pro Thr Cys Ala
210 215 220

Ser Ile Pro Ala Pro Tyr Arg Glu Arg Ala Gln Met Ala Tyr Ala Thr
225 230 235 240

Gly Met Arg Ile Cys Asp Met Val Arg Glu Asp Leu Arg Pro Ser His
245 250 255

Ile Leu Thr Arg Gln Ala Phe Glu Asn Ala Ile Val Val Ala Ser Ala
260 265 270

Leu Gly Ala Ser Thr Asn Cys Pro Pro His Leu Ile Ala Met Ala Arg
275 280 285

His Ala Gly Ile Asp Leu Ser Leu Asp Asp Trp Gln Arg Leu Gly Glu
290 295 300

Asp Val Pro Leu Leu Val Asn Cys Val Pro Ala Gly Glu His Leu Gly
305 310 315 320

Glu Gly Phe His Arg Ala Gly Gly Val Pro Ala Val Met His Glu Leu
325 330 335

Phe Ala Ala Gly Arg Leu His Pro Asp Cys Pro Thr Val Ser Gly Lys
340 345 350

Thr Ile Gly Asp Ile Ala Ala Gly Ala Lys Thr Arg Asp Ala Asp Val
355 360 365

```
Ile Arg Ser Cys Ala Ala Pro Leu Lys His Arg Ala Gly Phe Ile Val
    370                 375                 380

Leu Ser Gly Asn Phe Phe Asp Ser Ala Ile Ile Lys Met Ser Val Val
385                 390                 395                 400

Gly Glu Ala Phe Arg Arg Ala Tyr Leu Ser Glu Pro Gly Ser Glu Asn
                405                 410                 415

Ala Phe Glu Ala Arg Ala Ile Val Phe Glu Gly Pro Glu Asp Tyr His
            420                 425                 430

Ala Arg Ile Glu Asp Pro Ala Leu Asn Ile Asp Glu His Cys Ile Leu
        435                 440                 445

Val Ile Arg Gly Ala Gly Thr Val Gly Tyr Pro Gly Ser Ala Glu Val
    450                 455                 460

Val Asn Met Ala Pro Pro Ser His Leu Ile Lys Arg Gly Val Asp Ser
465                 470                 475                 480

Leu Pro Cys Leu Gly Asp Gly Arg Gln Ser Gly Thr Ser Gly Ser Pro
                485                 490                 495

Ser Ile Leu Asn Met Ser Pro Glu Ala Ala Val Gly Gly Gly Leu Ala
            500                 505                 510

Leu Leu Arg Thr Gly Asp Lys Ile Arg Val Asp Leu Asn Gln Arg Ser
        515                 520                 525

Val Thr Ala Leu Val Asp Asp Ala Glu Met Ala Arg Arg Lys Gln Glu
    530                 535                 540

Pro Pro Tyr Gln Ala Pro Ala Ser Gln Thr Pro Trp Gln Glu Leu Tyr
545                 550                 555                 560

Arg Gln Leu Val Gly Gln Leu Ser Thr Gly Gly Cys Leu Glu Pro Ala
                565                 570                 575

Thr Leu Tyr Leu Lys Val Ile Glu Thr Arg Gly Asp Pro Arg His Ser
            580                 585                 590

His
```

<210> SEQ ID NO 34
<211> LENGTH: 602
<212> TYPE: PRT
<213> ORGANISM: Acinetobacter sp.

<400> SEQUENCE: 34

```
Met Ser Glu Arg Ile Lys Lys Met Asn Asp Gln Asn Lys Arg Ile Phe
1               5                   10                  15

Leu Arg Ser Gln Glu Trp Phe Asp Asp Pro Glu His Ala Asp Met Thr
            20                  25                  30

Ala Leu Tyr Val Glu Arg Tyr Met Asn Tyr Gly Leu Thr Arg Ala Glu
        35                  40                  45

Leu Gln Ser Gly Arg Pro Ile Ile Gly Ile Ala Gln Thr Gly Ser Asp
    50                  55                  60

Leu Thr Pro Cys Asn Arg His His Lys Glu Leu Ala Glu Arg Val Lys
65                  70                  75                  80

Ala Gly Ile Arg Asp Ala Gly Gly Ile Pro Met Glu Phe Pro Val His
                85                  90                  95

Pro Ile Ala Glu Gln Thr Arg Arg Pro Thr Ala Ala Leu Asp Arg Asn
            100                 105                 110

Leu Ala Tyr Leu Gly Leu Val Glu Ile Leu His Gly Tyr Pro Leu Asp
        115                 120                 125

Gly Val Val Leu Thr Thr Gly Cys Asp Lys Thr Thr Pro Ala Cys Leu
    130                 135                 140
```

```
Met Ala Ala Ala Thr Thr Asp Ile Pro Ala Ile Val Leu Ser Gly Gly
145                 150                 155                 160

Pro Met Leu Asp Gly His Phe Lys Gly Glu Leu Ile Gly Ser Gly Thr
                165                 170                 175

Val Leu Trp His Ala Arg Asn Leu Leu Ala Thr Gly Glu Ile Asp Tyr
            180                 185                 190

Glu Gly Phe Met Glu Met Thr Thr Ser Ala Ser Pro Ser Val Gly His
        195                 200                 205

Cys Asn Thr Met Gly Thr Ala Leu Ser Met Asn Ala Leu Ala Glu Ala
    210                 215                 220

Leu Gly Met Ser Leu Pro Thr Cys Ala Ser Ile Pro Ala Pro Tyr Arg
225                 230                 235                 240

Glu Arg Gly Gln Met Ala Tyr Met Thr Gly Lys Arg Ile Cys Glu Met
                245                 250                 255

Val Leu Glu Asp Leu Arg Pro Ser Lys Ile Met Asn Lys Gln Ser Phe
            260                 265                 270

Glu Asn Ala Ile Ala Val Ala Ser Ala Leu Gly Ala Ser Ser Asn Cys
        275                 280                 285

Pro Pro His Leu Ile Ala Ile Ala Arg His Met Gly Ile Glu Leu Ser
    290                 295                 300

Leu Glu Asp Trp Gln Arg Val Gly Glu Asn Ile Pro Leu Ile Val Asn
305                 310                 315                 320

Cys Met Pro Ala Gly Lys Tyr Leu Gly Glu Gly Phe His Arg Ala Gly
                325                 330                 335

Gly Val Pro Ala Val Leu His Glu Leu Gln Lys Ala Ser Val Leu His
            340                 345                 350

Glu Gly Cys Ala Ser Val Ser Gly Lys Thr Met Gly Glu Ile Ala Lys
        355                 360                 365

Asn Ala Lys Thr Ser Asn Val Asp Val Ile Phe Pro Tyr Glu Gln Pro
    370                 375                 380

Leu Lys His Gly Ala Gly Phe Ile Val Leu Ser Gly Asn Phe Phe Asp
385                 390                 395                 400

Ser Ala Ile Met Lys Met Ser Val Val Gly Glu Ala Phe Lys Lys Thr
                405                 410                 415

Tyr Leu Ser Asp Pro Asn Gly Glu Asn Ser Phe Glu Ala Arg Ala Ile
            420                 425                 430

Val Phe Glu Gly Pro Glu Asp Tyr His Ala Arg Ile Asn Asp Pro Ala
        435                 440                 445

Leu Asp Ile Asp Glu His Cys Ile Leu Val Ile Arg Gly Ala Gly Thr
    450                 455                 460

Val Gly Tyr Pro Gly Ser Ala Glu Val Val Asn Met Ala Pro Pro Ala
465                 470                 475                 480

Glu Leu Ile Lys Lys Gly Ile Asp Ser Leu Pro Cys Leu Gly Asp Gly
                485                 490                 495

Arg Gln Ser Gly Thr Ser Ala Ser Pro Ser Ile Leu Asn Met Ser Pro
            500                 505                 510

Glu Ala Ala Val Gly Gly Gly Ile Ala Leu Leu Lys Thr Asn Asp Arg
        515                 520                 525

Leu Arg Ile Asp Leu Asn Lys Arg Ser Val Asn Val Leu Ile Ser Asp
    530                 535                 540

Glu Glu Leu Glu Gln Arg Arg Arg Glu Trp Lys Pro Thr Val Ser Ser
545                 550                 555                 560
```

-continued

```
Ser Gln Thr Pro Trp Gln Glu Met Tyr Arg Asn Met Val Gly Gln Leu
                565                 570                 575

Ser Thr Gly Gly Cys Leu Glu Pro Ala Thr Leu Tyr Met Arg Val Ile
            580                 585                 590

Asn Gln Asp Asn Leu Pro Arg His Ser His
        595                 600


<210> SEQ ID NO 35
<211> LENGTH: 593
<212> TYPE: PRT
<213> ORGANISM: Achromobacter xylosoxidans

<400> SEQUENCE: 35

Met Ser Gln Thr Pro Arg Lys Leu Arg Ser Gln Lys Trp Phe Asp Asp
1               5                   10                  15

Pro Ala His Ala Asp Met Thr Ala Ile Tyr Val Glu Arg Tyr Leu Asn
            20                  25                  30

Tyr Gly Leu Thr Arg Gln Glu Leu Gln Ser Gly Arg Pro Ile Ile Gly
        35                  40                  45

Ile Ala Gln Thr Gly Ser Asp Leu Ala Pro Cys Asn Arg His His Leu
    50                  55                  60

Ala Leu Ala Glu Arg Ile Lys Ala Gly Ile Arg Asp Ala Gly Gly Ile
65                  70                  75                  80

Pro Met Glu Phe Pro Val His Pro Leu Ala Glu Gln Gly Arg Arg Pro
                85                  90                  95

Thr Ala Ala Leu Asp Arg Asn Leu Ala Tyr Leu Gly Leu Val Glu Ile
            100                 105                 110

Leu His Gly Tyr Pro Leu Asp Gly Val Val Leu Thr Thr Gly Cys Asp
        115                 120                 125

Lys Thr Thr Pro Ala Cys Leu Met Ala Ala Ala Thr Val Asp Ile Pro
    130                 135                 140

Ala Ile Val Leu Ser Gly Gly Pro Met Leu Asp Gly Trp His Asp Gly
145                 150                 155                 160

Gln Arg Val Gly Ser Gly Thr Val Ile Trp His Ala Arg Asn Leu Met
                165                 170                 175

Ala Ala Gly Lys Leu Asp Tyr Glu Gly Phe Met Thr Leu Ala Thr Ala
            180                 185                 190

Ser Ser Pro Ser Ile Gly His Cys Asn Thr Met Gly Thr Ala Leu Ser
        195                 200                 205

Met Asn Ser Leu Ala Glu Ala Leu Gly Met Ser Leu Pro Thr Cys Ala
    210                 215                 220

Ser Ile Pro Ala Pro Tyr Arg Glu Arg Gly Gln Met Ala Tyr Ala Thr
225                 230                 235                 240

Gly Leu Arg Ile Cys Asp Met Val Arg Glu Asp Leu Arg Pro Ser His
                245                 250                 255

Val Leu Thr Arg Gln Ala Phe Glu Asn Ala Ile Val Val Ala Ser Ala
            260                 265                 270

Leu Gly Ala Ser Ser Asn Cys Pro Pro His Leu Ile Ala Met Ala Arg
        275                 280                 285

His Ala Gly Ile Asp Leu Ser Leu Asp Asp Trp Gln Arg Leu Gly Glu
    290                 295                 300

Asp Val Pro Leu Leu Val Asn Cys Val Pro Ala Gly Glu His Leu Gly
305                 310                 315                 320

Glu Gly Phe His Arg Ala Gly Gly Val Pro Ala Val Leu His Glu Leu
                325                 330                 335
```

-continued

```
Ala Ala Ala Gly Arg Leu His Met Asp Cys Ala Thr Val Ser Gly Lys
            340                 345                 350

Thr Ile Gly Glu Ile Ala Ala Ala Ala Lys Thr Asn Asn Ala Asp Val
        355                 360                 365

Ile Arg Ser Cys Asp Ala Pro Leu Lys His Arg Ala Gly Phe Ile Val
    370                 375                 380

Leu Ser Gly Asn Phe Phe Asp Ser Ala Ile Ile Lys Met Ser Val Val
385                 390                 395                 400

Gly Glu Ala Phe Arg Arg Ala Tyr Leu Ser Glu Pro Gly Ser Glu Asn
                405                 410                 415

Ala Phe Glu Ala Arg Ala Ile Val Phe Glu Gly Pro Glu Asp Tyr His
            420                 425                 430

Ala Arg Ile Glu Asp Pro Thr Leu Asn Ile Asp Glu His Cys Ile Leu
        435                 440                 445

Val Ile Arg Gly Ala Gly Thr Val Gly Tyr Pro Gly Ser Ala Glu Val
    450                 455                 460

Val Asn Met Ala Pro Pro Ser His Leu Leu Lys Arg Gly Ile Asp Ser
465                 470                 475                 480

Leu Pro Cys Leu Gly Asp Gly Arg Gln Ser Gly Thr Ser Ala Ser Pro
                485                 490                 495

Ser Ile Leu Asn Met Ser Pro Glu Ala Ala Val Gly Gly Gly Leu Ala
            500                 505                 510

Leu Leu Arg Thr Gly Asp Arg Ile Arg Val Asp Leu Asn Gln Arg Ser
        515                 520                 525

Val Ile Ala Leu Val Asp Gln Thr Glu Met Glu Arg Arg Lys Leu Glu
    530                 535                 540

Pro Pro Tyr Gln Ala Pro Glu Ser Gln Thr Pro Trp Gln Glu Leu Tyr
545                 550                 555                 560

Arg Gln Leu Val Gly Gln Leu Ser Thr Gly Gly Cys Leu Glu Pro Ala
                565                 570                 575

Thr Leu Tyr Leu Lys Val Val Glu Thr Arg Gly Asp Pro Arg His Ser
            580                 585                 590

His
```

<210> SEQ ID NO 36
<211> LENGTH: 1782
<212> TYPE: DNA
<213> ORGANISM: Achromobacter piechaudii

<400> SEQUENCE: 36

```
atgtctcaga caccccgcaa gttgcgcagc cagaaatggt tcgacgaccc tgcgcatgcc      60

gatatgacgg cgatttacgt cgagcgttat ctgaattacg gcctgacgcg gcaagagttg     120

cagtccgggc ggccgatcat cggcatcgcc cagaccggca gcgatctggc gccctgcaac     180

cgccatcacc tggcgctggc cgagcgcgtc aaagcgggca tccgggacgc gggcggcatc     240

ccgatggagt tccccgtgca cccgctggcc gaacaaggcc ggcggcccac ggccgcgctg     300

gaccgcaacc tggcctatct gggcctggtc gaaatcctgc acggctaccc cttggacggg     360

gtggtgctga cgactggctg cgacaagacc acgcctgcct gcctgatggc cgccgccacg     420

gtcgacctgc ccgccatcgt gctgtccggc ggccccatgc tggacggctg gcacgacggc     480

cagcgcgtcg gttccggcac cgtcatctgg cacgcgcgca acctgatggc ggccggcaag     540

cttgattacg aaggcttcat gacgctggcc accgcgtctt cgccgtcggt cggccactgc     600
```

-continued

```
aacaccatgg gcacggcgtt gtcgatgaat tcgctggccg aagcgctggg catgtcgctg    660

cccacctgcg ccagcattcc cgccccctac cgcgaacgcg cccagatggc ctacgccacc    720

ggcatgcgca tctgcgacat ggtgcgcgaa gacctgcgac cctcccacat cctgacacgg    780

caggcattcg agaacgccat cgtcgtggca tcggcgctgg gcgcgtccac caattgcccg    840

ccgcacctga tcgcgatggc ccgccacgcc ggcatcgacc ttagcctgga cgactggcag    900

cgcctgggtg aagacgtgcc gctgctggtc aactgcgtgc cggcgggcga gcatctgggc    960

gagggcttcc accgcgcggg cggcgtcccc gcggtcatgc atgaactgtt cgccgccggg   1020

cgccttcacc ccgactgccc caccgtatcc ggcaagacca tcggggacat cgccgcgggc   1080

gccaagaccc gcgacgccga cgtcatccgc agctgcgccg ccccgctgaa acaccgggca   1140

ggcttcatcg tgctgtcggg caatttcttc gacagcgcca tcatcaagat gtcggtcgta   1200

ggcgaagcgt tccgccgcgc ctacctgtcc gaacccggct cagagaacgc cttcgaggcc   1260

cgcgccatcg tgttcgaagg ccccgaggac taccacgcgc gcatcgaaga cccggcgctg   1320

aacatcgacg aacactgcat ccttgtcatc cgcggcgccg gcaccgtggg ctacccgggc   1380

agcgccgaag tggtcaacat ggcgccgccg tcccacctga tcaagcgcgg cgtggattcc   1440

ctgccgtgcc tgggggatgg caggcaaagc ggcacttccg gcagcccgtc cattttgaac   1500

atgtcccctg aagcagcagt cgggggagga ttggcgctgc tgcgcaccgg cgacaagatc   1560

cgtgtcgatc tgaaccagcg cagcgtcacc gccttggtcg acgacgcgga aatggcaaga   1620

cggaagcaag aaccgcccta ccaggcaccg gcctcgcaaa cgccctggca agagctgtac   1680

cggcaactgg tcggccagtt gtcgacgggc ggctgcctgg agcccgcgac gctatatctg   1740

aaagtcatcg aaacgcgcgg cgatccccgg cactctcact ga                      1782
```

```
<210> SEQ ID NO 37
<211> LENGTH: 1809
<212> TYPE: DNA
<213> ORGANISM: Acinetobacter sp.

<400> SEQUENCE: 37

atgagtgaaa ggatcaaaaa aatgaatgat caaaataaac ggattttttt acgtagccaa     60

gaatggtttg atgatcctga acatgctgac atgacagcac tctatgttga gcgttatatg    120

aattatggcc tgacccgtgc cgagctacaa tcaggccgcc cgattattgg tattgcacaa    180

actggcagtg atttaactcc atgtaaccgt caccacaaag aacttgctga acgggttaaa    240

gcaggtattc gagatgcggg aggtattccc atggaattcc ccgttcaccc gattgcagaa    300

caaacccgtc gccctactgc tgcacttgat agaaatttag cttacttagg cttagttgaa    360

atattgcatg gttatccgct tgatggtgtg gtgctaacca caggttgtga caaaactaca    420

cctgcttgtt taatggctgc cgcaacgaca gatataccag ccattgtgtt gtctggtgga    480

ccaatgctag atggtcattt taaaggtgag ttaattggtt ctgggactgt gctttggcat    540

gcaagaaatt tacttgccac gggtgaaatt gattatgaag ggttcatgga aatgaccact    600

tcagcatcgc cttcggtcgg acattgcaac accatgggca ctgcactttc tatgaatgcc    660

ttggcagaag ctttgggcat gtctttaccg acatgtgcaa gtattccagc gccgtatcgc    720

gaacgagggc aaatggccta tatgacaggc aaaagaattt gtgaaatggt tttagaagat    780

ttacgccctt ctaaaatcat gaacaaacaa tcatttgaaa atgccatcgc ggtagcttca    840

gcattagggg catcaagtaa ttgccctcct cacctcattg caattgcccg tcatatgggc    900

attgagctca gtttagaaga ctggcaacgc gttggggaga acattcctct cattgtgaac    960
```

-continued

```
tgtatgcctg cgggtaaata tttaggtgaa ggttttcacc gtgctggcgg tgttcctgct   1020

gttttgcatg aattacaaaa ggccagcgtt ttacatgaag gctgtgcatc agtcagcggt   1080

aaaacgatgg gagaaattgc taaaaatgct aaaacctcca atgtagatgt tatttttcca   1140

tatgaacaac cattaaaaca tggtgcaggt tttattgtgc ttagtggcaa tttcttcgac   1200

agcgccatta tgaaaatgtc tgttgtgggt gaagcattta agaaaaccta tttatctgac   1260

ccaaatgggg aaaatagctt tgaagcacgg gcaatcgttt ttgaagggcc agaggactac   1320

catgcacgaa ttaatgatcc agccttagac attgatgaac attgtatttt ggtcattcgt   1380

ggcgctggaa cagtgggcta tccaggtagt gcagaagttg taaatatggc tccacccgca   1440

gagttaatta aaaaaggcat cgattcactg ccttgcttag gagatggccg ccaaagtggt   1500

acgtctgcca gcccttctat tttaaatatg tcacccgaag cggcggtagg cggtggaatt   1560

gcattattaa agaccaatga ccgtttacgc attgatctca ataaacgctc cgtcaacgta   1620

ctcatttctg acgaagagtt agaacaacgc cgccgtgagt ggaaaccgac ggtctcttca   1680

tctcaaacac cttggcaaga aatgtatcgc aacatggtgg gtcaattatc cactggcggt   1740

tgtttggaac ctgcaacttt atatatgcga gtcataaatc aagacaacct tccaagacac   1800

tctcattaa                                                           1809
```

<210> SEQ ID NO 38
<211> LENGTH: 1782
<212> TYPE: DNA
<213> ORGANISM: Achromobacter xylosoxidans

<400> SEQUENCE: 38

```
atgagccaaa caccgcgtaa attacgcagc cagaagtggt ttgacgatcc tgcacatgcc     60

gatatgaccg ccatctatgt tgaacgctac ctgaactatg gcttaacccg ccaagaactg    120

caaagtggtc gcccgattat tggtattgcc caaaccggca gcgatttagc cccgtgtaat    180

cgccatcatt tagccttagc cgaacgcatt aaagcaggca ttagagatgc aggcggcatt    240

cctatggaat ttcccgttca tccgctggcc gaacaaggta gacgtcctac agcagcatta    300

gatcgcaatt tagcctattt aggcctggtg gaaattttac acggctatcc cctggacggt    360

gtggtgctga caaccggttg cgataaaaca acaccggcgt gtttaatggc agctgcaaca    420

gttgatattc cggcgatcgt gttatcaggt ggtccgatgt tagatggctg gcatgatggc    480

caaagagttg gcagtggtac cgtgatttgg catgcacgca atttaatggc agcaggcaaa    540

ctggattatg aaggcttcat gaccctggcg acagcctctt ctccgagtat tggacactgt    600

aataccatgg gcacagcctt aagcatgaat agtctggcag aagccctggg tatgtcttta    660

ccgacctgtg cgtctattcc agccccgtat agagaacgcg gtcaaatggc gtatgctact    720

ggtttacgca tttgcgatat ggtgcgcgaa gatttacgcc cgtcacatgt tttaacccgc    780

caagccttcg aaaatgccat tgttgttgcc tcagccttag gtgcaagctc taattgtccc    840

cctcatttaa ttgccatggc ccgtcatgcc ggtatcgact taagcctgga tgactggcaa    900

cgcttaggcg aagatgttcc gttactggtc aattgtgtgc ctgccggtga acatttaggt    960

gaaggatttc atcgcgcggg tggtgttcct gctgttttac atgaattagc tgccgcaggt   1020

cgtttacata tggattgtgc taccgtttct ggcaagacca tcggcgaaat tgcagctgcc   1080

gcaaaaacca acaacgcaga cgtgattcgc tcgtgtgatg ccccgttaaa acatagagcc   1140

ggctttattg tgttaagcgg caatttcttc gactccgcca tcatcaagat gtccgttgtg   1200
```

```
ggtgaagcct ttcgcagagc ctatttaagt gaacctggca gcgaaaatgc ctttgaagcc   1260

cgtgccatcg tgtttgaagg cccggaagac tatcatgccc gcattgaaga tccgaccctg   1320

aatattgatg aacactgcat tctggtgatt cgcggcgcag gtaccgttgg ttatcctggt   1380

agtgctgaag ttgtgaatat ggccccgccg agccatttat taaaacgcgg tattgattca   1440

ttaccttgcc tgggagatgg ccgccaaagt ggtacctcag ctagtccgtc tatcctgaat   1500

atgagccctg aagccgccgt tggaggaggt ttagcattat taagaaccgg tgatcgcatt   1560

cgcgtcgatc tgaatcaacg ctcagtcatt gcattagtcg accagaccga aatggaacgc   1620

cgcaaattag aaccaccgta tcaagcacct gaaagccaaa ccccgtggca agaactgtat   1680

cgccaattag tcggtcaact gtcaacaggc ggctgcctgg aaccagccac cttatattta   1740

aaagtcgtgg aaacccgtgg agatcctcgt catagccatt aa                      1782
```

<210> SEQ ID NO 39
<211> LENGTH: 451
<212> TYPE: PRT
<213> ORGANISM: Terriglobuds roseus

<400> SEQUENCE: 39

```
Met Asp Arg Arg Glu Leu Leu Lys Thr Ser Ala Leu Leu Met Ala Ala
1               5                   10                  15

Ala Pro Leu Ala Arg Ala Ala Asn Val Pro Glu Asp His Ala Asn Val
            20                  25                  30

Pro Arg Thr Asn Trp Ser Lys Asn Phe His Tyr Ser Thr Ser Arg Val
        35                  40                  45

Tyr Ala Pro Thr Thr Pro Glu Glu Val Pro Ala Ile Val Leu Glu Asn
    50                  55                  60

Gly His Leu Lys Gly Leu Gly Ser Arg His Cys Phe Asn Asn Ile Ala
65                  70                  75                  80

Asp Ser Gln Tyr Ala Gln Ile Ser Met Arg Glu Val Lys Gly Ile Gln
                85                  90                  95

Ile Asp Glu Ala Ala Gln Thr Val Thr Val Gly Ala Gly Ile Ala Tyr
            100                 105                 110

Gly Glu Leu Ala Pro Val Leu Asp Lys Ala Gly Phe Ala Leu Ala Asn
        115                 120                 125

Leu Ala Ser Leu Pro His Ile Ser Val Gly Gly Thr Ile Ala Thr Ala
    130                 135                 140

Thr His Gly Ser Gly Val Gly Asn Lys Asn Leu Ser Ser Ala Thr Arg
145                 150                 155                 160

Ala Ile Glu Ile Val Lys Ala Asp Gly Ser Ile Leu Arg Leu Ser Arg
                165                 170                 175

Asp Thr Asp Gly Glu Arg Phe Arg Met Ala Val Val His Leu Gly Ala
            180                 185                 190

Leu Gly Val Leu Thr Lys Val Thr Leu Asp Ile Val Pro Arg Phe Asp
        195                 200                 205

Met Ser Gln Val Val Tyr Arg Asn Leu Ser Phe Asp Gln Leu Glu His
    210                 215                 220

Asn Leu Asp Thr Ile Leu Ser Ser Gly Tyr Ser Val Ser Leu Phe Thr
225                 230                 235                 240

Asp Trp Gln Arg Asn Arg Val Asn Gln Val Trp Ile Lys Asp Lys Ala
                245                 250                 255

Thr Ala Asp Ala Pro Gln Lys Pro Leu Pro Pro Met Phe Tyr Gly Ala
            260                 265                 270
```

-continued

Thr Leu Gln Thr Ala Lys Leu His Pro Ile Asp Asp His Pro Ala Asp
275 280 285

Ala Cys Thr Glu Gln Met Gly Ser Val Gly Pro Trp Tyr Leu Arg Leu
290 295 300

Pro His Phe Lys Met Glu Phe Thr Pro Ser Ser Gly Glu Glu Leu Gln
305 310 315 320

Thr Glu Tyr Phe Val Ala Arg Lys Asp Gly Tyr Arg Ala Ile Arg Ala
325 330 335

Val Glu Lys Leu Arg Asp Lys Ile Thr Pro His Leu Phe Ile Thr Glu
340 345 350

Ile Arg Thr Ile Ala Ala Asp Asp Leu Pro Met Ser Met Ala Tyr Gln
355 360 365

Arg Asp Ser Met Ala Ile His Phe Thr Trp Lys Pro Glu Glu Pro Thr
370 375 380

Val Arg Lys Leu Leu Pro Glu Ile Glu Ala Ala Leu Ala Pro Phe Gly
385 390 395 400

Val Arg Pro His Trp Gly Lys Ile Phe Glu Ile Pro Pro Ser Tyr Leu
405 410 415

His Lys Gln Tyr Pro Ala Leu Pro Arg Phe Arg Ala Met Ala Gln Ala
420 425 430

Leu Asp Pro Gly Gly Lys Phe Arg Asn Ala Tyr Leu Asp Arg Asn Ile
435 440 445

Phe Gly Ala
450

<210> SEQ ID NO 40
<211> LENGTH: 450
<212> TYPE: PRT
<213> ORGANISM: Granulicella mallensis

<400> SEQUENCE: 40

Met Asp Lys Arg Asp Phe Leu Lys Gly Ser Ala Thr Thr Ala Val Ala
1 5 10 15

Leu Met Met Gly Leu Asn Glu Ser Lys Ala Phe Ala Asp Asp Ser Val
20 25 30

Pro Arg Thr Asn Trp Ser Gly Asn Tyr His Tyr Ser Thr Asn Lys Val
35 40 45

Leu Gln Pro Ala Ser Val Ala Glu Thr Gln Asp Ala Val Arg Ser Val
50 55 60

Ala Gly Val Arg Ala Leu Gly Thr Arg His Ser Phe Asn Gly Ile Ala
65 70 75 80

Asp Ser Gln Ile Ala Gln Ile Ser Thr Leu Lys Leu Lys Asp Val Ser
85 90 95

Leu Asp Ala Lys Ser Ser Thr Val Thr Val Gly Ala Gly Ile Arg Tyr
100 105 110

Gly Asp Leu Ala Val Gln Leu Asp Ala Lys Gly Phe Ala Leu His Asn
115 120 125

Leu Ala Ser Leu Pro His Ile Ser Val Gly Gly Ala Cys Ala Thr Ala
130 135 140

Thr His Gly Ser Gly Met Gly Asn Gly Asn Leu Ala Thr Ala Val Lys
145 150 155 160

Ala Val Glu Phe Val Ala Ala Asp Gly Ser Val His Thr Leu Ser Arg
165 170 175

Asp Arg Asp Gly Asp Arg Phe Ala Gly Ser Val Val Gly Leu Gly Ala
180 185 190

```
Leu Gly Val Val Thr His Leu Thr Leu Gln Val Gln Pro Arg Phe Glu
        195                 200                 205

Met Thr Gln Val Val Tyr Arg Asp Leu Pro Phe Ser Glu Leu Glu His
    210                 215                 220

His Leu Pro Glu Ile Met Gly Ala Gly Tyr Ser Val Ser Leu Phe Thr
225                 230                 235                 240

Asp Trp Gln Asn Gly Arg Ala Gly Glu Val Trp Ile Lys Arg Arg Val
                245                 250                 255

Asp Gln Gly Gly Ala Ser Ala Pro Pro Ala Arg Phe Phe Asn Ala Thr
            260                 265                 270

Leu Ala Thr Thr Lys Leu His Pro Ile Leu Asp His Pro Ala Glu Ala
        275                 280                 285

Cys Thr Asp Gln Leu Asn Thr Val Gly Pro Trp Tyr Glu Arg Leu Pro
    290                 295                 300

His Phe Lys Leu Asn Phe Thr Pro Ser Ser Gly Gln Glu Leu Gln Thr
305                 310                 315                 320

Glu Phe Phe Val Pro Phe Asp Arg Gly Tyr Asp Ala Ile Arg Ala Val
                325                 330                 335

Glu Thr Leu Arg Asp Val Ile Thr Pro His Leu Tyr Ile Thr Glu Leu
            340                 345                 350

Arg Ala Val Ala Ala Asp Asp Leu Trp Met Ser Met Ala Tyr Gln Arg
        355                 360                 365

Pro Ser Leu Ala Ile His Phe Thr Trp Lys Pro Glu Thr Asp Ala Val
    370                 375                 380

Leu Lys Leu Leu Pro Gln Ile Glu Ala Lys Leu Ala Pro Phe Gly Ala
385                 390                 395                 400

Arg Pro His Trp Ala Lys Val Phe Thr Met Lys Ser Ser His Val Ala
                405                 410                 415

Pro Leu Tyr Pro Arg Leu Lys Asp Phe Leu Val Leu Ala Lys Ser Phe
            420                 425                 430

Asp Pro Lys Gly Lys Phe Gln Asn Ala Phe Leu Gln Asp His Val Asp
        435                 440                 445

Ile Ala
    450


<210> SEQ ID NO 41
<211> LENGTH: 414
<212> TYPE: PRT
<213> ORGANISM: Streptomyces acidiscabies

<400> SEQUENCE: 41

Met Thr Ala Ser Val Thr Asn Trp Ala Gly Asn Ile Ser Phe Val Ala
1               5                   10                  15

Lys Asp Val Val Arg Pro Gly Gly Val Glu Ala Leu Arg Lys Val Val
            20                  25                  30

Ala Gly Asn Asp Arg Val Arg Val Leu Gly Ser Gly His Ser Phe Asn
        35                  40                  45

Arg Ile Ala Glu Pro Gly Ala Asp Gly Val Leu Val Ser Leu Asp Ala
    50                  55                  60

Leu Pro Gln Val Ile Asp Val Asp Thr Glu Arg Arg Thr Val Arg Val
65                  70                  75                  80

Gly Gly Gly Val Lys Tyr Ala Glu Leu Ala Arg His Val Asn Glu Ser
                85                  90                  95

Gly Leu Ala Leu Pro Asn Met Ala Ser Leu Pro His Ile Ser Val Ala
```

```
            100                 105                 110

Gly Ser Val Ala Thr Gly Thr His Gly Ser Gly Val Asn Asn Gly Pro
        115                 120                 125

Leu Ala Thr Pro Val Arg Glu Val Glu Leu Leu Thr Ala Asp Gly Ser
    130                 135                 140

Leu Val Thr Ile Gly Lys Asp Asp Ala Arg Phe Pro Gly Ala Val Thr
145                 150                 155                 160

Ser Leu Gly Ala Leu Gly Val Val Val Ala Leu Thr Leu Asp Leu Glu
                165                 170                 175

Pro Ala Tyr Gly Val Glu Gln Tyr Thr Phe Thr Glu Leu Pro Leu Glu
            180                 185                 190

Gly Leu Asp Phe Glu Ala Val Ala Ser Ala Ala Tyr Ser Val Ser Leu
        195                 200                 205

Phe Thr Asp Trp Arg Glu Ala Gly Phe Arg Gln Val Trp Val Lys Arg
    210                 215                 220

Arg Ile Asp Glu Pro Tyr Ala Gly Phe Pro Trp Ala Ala Pro Ala Thr
225                 230                 235                 240

Glu Lys Leu His Pro Val Pro Gly Met Pro Ala Glu Asn Cys Thr Asp
                245                 250                 255

Gln Phe Gly Ala Ala Gly Pro Trp His Glu Arg Leu Pro His Phe Lys
            260                 265                 270

Ala Glu Phe Thr Pro Ser Ser Gly Asp Glu Leu Gln Ser Glu Tyr Leu
        275                 280                 285

Leu Pro Arg Glu His Ala Leu Ala Ala Leu Asp Ala Val Gly Asn Val
    290                 295                 300

Arg Glu Thr Val Ser Thr Val Leu Gln Ile Cys Glu Val Arg Thr Ile
305                 310                 315                 320

Ala Ala Asp Thr Gln Trp Leu Ser Pro Ala Tyr Gly Arg Asp Ser Val
                325                 330                 335

Ala Leu His Phe Thr Trp Thr Asp Asp Met Asp Ala Val Leu Pro Ala
            340                 345                 350

Val Arg Ala Val Glu Ser Ala Leu Asp Gly Phe Gly Ala Arg Pro His
        355                 360                 365

Trp Gly Lys Val Phe Thr Thr Ala Pro Ala Ala Leu Arg Glu Arg Tyr
    370                 375                 380

Pro Arg Leu Asp Asp Phe Arg Thr Leu Arg Asp Glu Leu Asp Pro Ala
385                 390                 395                 400

Gly Lys Phe Thr Asn Ala Phe Val Arg Asp Val Leu Glu Gly
                405                 410


<210> SEQ ID NO 42
<211> LENGTH: 427
<212> TYPE: PRT
<213> ORGANISM: Actinomycetales

<400> SEQUENCE: 42

Met Thr Leu Glu Arg Asn Trp Ala Gly Thr His Thr Phe Ala Ala Pro
1               5                   10                  15

Arg Ile Val Asn Ala Thr Ser Ile Asp Glu Val Arg Ala Leu Val Ala
            20                  25                  30

Glu Ala Ala Arg Thr Gly Thr Arg Val Arg Ala Leu Gly Thr Arg His
        35                  40                  45

Ser Phe Thr Asp Leu Ala Asp Ser Asp Gly Thr Leu Ile Thr Val Leu
    50                  55                  60
```

```
Asp Ile Pro Ala Asp Pro Val Phe Asp Glu Ala Ala Gly Ser Val Thr
65                  70                  75                  80

Ile Gly Ala Gly Thr Arg Tyr Gly Ile Ala Ala Ala Trp Leu Ala Glu
                85                  90                  95

His Gly Leu Ala Phe His Asn Met Gly Ser Leu Pro His Ile Ser Val
            100                 105                 110

Gly Gly Ala Ile Ala Thr Gly Thr His Gly Ser Gly Asn Asp Asn Gly
        115                 120                 125

Ile Leu Ser Ser Ala Val Ser Gly Leu Glu Tyr Val Asp Ala Thr Gly
    130                 135                 140

Glu Leu Val His Val Arg Arg Gly Asp Pro Gly Phe Asp Gly Leu Val
145                 150                 155                 160

Val Gly Leu Gly Ala Tyr Gly Ile Val Val Arg Val Thr Val Asp Val
                165                 170                 175

Gln Pro Ala Tyr Arg Val Arg Gln Asp Val Tyr Arg Asp Val Pro Trp
            180                 185                 190

Asp Ala Val Leu Ala Asp Phe Glu Gly Val Thr Gly Gly Ala Tyr Ser
        195                 200                 205

Val Ser Ile Phe Thr Asn Trp Leu Gly Asp Thr Val Glu Gln Ile Trp
    210                 215                 220

Trp Lys Thr Arg Leu Val Ala Gly Asp Asp Glu Leu Pro Val Val Pro
225                 230                 235                 240

Glu Ser Trp Leu Gly Val Gln Arg Asp Ser Leu Thr Ala Gly Asn Leu
                245                 250                 255

Val Glu Thr Asp Pro Asp Asn Leu Thr Leu Gln Gly Gly Val Pro Gly
            260                 265                 270

Asp Trp Trp Glu Arg Leu Pro His Phe Arg Leu Glu Ser Thr Pro Ser
        275                 280                 285

Asn Gly Asp Glu Ile Gln Thr Glu Tyr Phe Ile Asp Arg Ala Asp Gly
    290                 295                 300

Pro Ala Ala Ile Thr Ala Leu Arg Ala Leu Gly Asp Arg Ile Ala Pro
305                 310                 315                 320

Leu Leu Leu Val Thr Glu Leu Arg Thr Ala Ala Pro Asp Lys Leu Trp
                325                 330                 335

Leu Ser Gly Ala Tyr His Arg Glu Met Leu Ala Val His Phe Thr Trp
            340                 345                 350

Arg Asn Leu Pro Glu Glu Val Arg Ala Val Leu Pro Ala Ile Glu Glu
        355                 360                 365

Ala Leu Ala Pro Phe Asp Ala Arg Pro His Trp Gly Lys Leu Asn Leu
    370                 375                 380

Leu Thr Ala Glu Arg Ile Ala Glu Val Val Pro Arg Leu Ala Asp Ala
385                 390                 395                 400

Arg Asp Leu Phe Glu Glu Leu Asp Pro Ala Gly Thr Phe Ser Asn Ala
                405                 410                 415

His Leu Glu Arg Ile Gly Val Arg Leu Pro Arg
            420                 425


<210> SEQ ID NO 43
<211> LENGTH: 419
<212> TYPE: PRT
<213> ORGANISM: Frankia sp.

<400> SEQUENCE: 43

Met Arg Asp Ala Ala Ala Ala Asn Trp Ala Gly Asn Val Arg Phe Gly
1               5                   10                  15
```

-continued

```
Ala Ala Arg Val Val Ala Pro Glu Ser Val Gly Glu Leu Gln Glu Ile
            20                  25                  30

Val Ala Gly Ser Arg Lys Ala Arg Ala Leu Gly Thr Gly His Ser Phe
        35                  40                  45

Ser Arg Ile Ala Asp Thr Asp Gly Thr Leu Ile Ala Thr Ala Arg Leu
    50                  55                  60

Pro Arg Arg Ile Gln Ile Asp Asp Gly Ser Val Thr Val Ser Gly Gly
65                  70                  75                  80

Ile Arg Tyr Gly Asp Leu Ala Arg Glu Leu Ala Pro Asn Gly Trp Ala
                85                  90                  95

Leu Arg Asn Leu Gly Ser Leu Pro His Ile Ser Val Ala Gly Ala Cys
            100                 105                 110

Ala Thr Gly Thr His Gly Ser Gly Asp Arg Asn Gly Ser Leu Ala Thr
        115                 120                 125

Ser Val Ala Ala Leu Glu Leu Val Thr Ala Ser Gly Glu Leu Val Ser
    130                 135                 140

Val Arg Arg Gly Asp Glu Asp Phe Asp Gly His Val Ile Ala Leu Gly
145                 150                 155                 160

Ala Leu Gly Val Thr Val Ala Val Thr Leu Asp Leu Val Pro Gly Phe
                165                 170                 175

Gln Val Arg Gln Leu Val Tyr Glu Gly Leu Thr Arg Asp Thr Leu Leu
            180                 185                 190

Glu Ser Val Gln Glu Ile Phe Ala Ala Ser Tyr Ser Val Ser Val Phe
        195                 200                 205

Thr Gly Trp Asp Pro Glu Ser Ser Gln Leu Trp Leu Lys Gln Arg Val
    210                 215                 220

Asp Gly Pro Gly Asp Asp Gly Glu Pro Pro Ala Glu Arg Phe Gly Ala
225                 230                 235                 240

Arg Leu Ala Thr Arg Pro Leu His Pro Val Pro Gly Ile Asp Pro Thr
                245                 250                 255

His Thr Thr Gln Gln Leu Gly Val Pro Gly Pro Trp His Glu Arg Leu
            260                 265                 270

Pro His Phe Arg Leu Asp Phe Thr Pro Ser Ala Gly Asp Glu Leu Gln
        275                 280                 285

Thr Glu Tyr Phe Val Ala Arg Glu His Ala Ala Ala Ala Ile Glu Ala
    290                 295                 300

Leu Phe Ala Ile Gly Ala Val Val Arg Pro Ala Leu Gln Ile Ser Glu
305                 310                 315                 320

Ile Arg Thr Val Ala Ala Asp Ala Leu Trp Leu Ser Pro Ala Tyr Arg
                325                 330                 335

Arg Asp Val Met Ala Leu His Phe Thr Trp Ile Ser Ala Glu Gly Thr
            340                 345                 350

Val Met Pro Ala Val Ala Ala Val Glu Arg Ala Leu Ala Pro Phe Asp
        355                 360                 365

Pro Val Pro His Trp Gly Lys Val Phe Ala Leu Pro Pro Ala Ala Val
    370                 375                 380

Arg Ala Gly Tyr Pro Arg Ala Ala Glu Phe Leu Ala Leu Ala Ala Arg
385                 390                 395                 400

Arg Asp Pro Glu Ala Val Phe Arg Asn Gln Tyr Leu Asp Ala Tyr Leu
                405                 410                 415

Pro Ala Ala
```

<210> SEQ ID NO 44
<211> LENGTH: 413
<212> TYPE: PRT
<213> ORGANISM: Propionibacteriacaeae

<400> SEQUENCE: 44

```
Met Thr Gln Arg Asn Trp Ala Gly Asn Val Ser Tyr Ser Ser Ser Arg
1               5                   10                  15

Val Ala Glu Pro Ala Ser Val Asp Asp Leu Thr Ala Leu Val Glu Ser
            20                  25                  30

Glu Pro Arg Val Arg Pro Leu Gly Ser Arg His Cys Phe Asn Asp Ile
        35                  40                  45

Ala Asp Thr Pro Gly Val His Val Ser Leu Ala Arg Leu Arg Gly Glu
    50                  55                  60

Glu Pro Arg Leu Thr Ala Pro Gly Thr Leu Arg Thr Pro Ala Trp Leu
65                  70                  75                  80

Arg Tyr Gly Asp Leu Val Pro Val Leu Arg Glu Ala Gly Ala Ala Leu
                85                  90                  95

Ala Asn Leu Ala Ser Leu Pro His Ile Ser Val Ala Gly Ala Val Gln
            100                 105                 110

Thr Gly Thr His Gly Ser Gly Asp Arg Ile Gly Thr Leu Ala Thr Gln
        115                 120                 125

Val Ser Ala Leu Glu Leu Val Thr Gly Thr Gly Glu Val Leu Arg Leu
    130                 135                 140

Glu Arg Gly Glu Pro Asp Phe Asp Gly Ala Val Val Gly Leu Gly Ala
145                 150                 155                 160

Leu Gly Val Leu Thr His Val Glu Leu Asp Val Ser Pro Ala Arg Asp
                165                 170                 175

Val Ala Gln His Val Tyr Glu Gly Val Arg Leu Asp Asp Val Leu Ala
            180                 185                 190

Asp Leu Gly Ala Val Thr Gly Ala Gly Asp Ser Val Ser Met Phe Thr
        195                 200                 205

His Trp Gln Asp Pro Ala Val Val Ser Gln Val Trp Val Lys Ser Gly
    210                 215                 220

Gly Asp Val Asp Asp Ala Ala Ile Arg Asp Ala Gly Gly Arg Pro Ala
225                 230                 235                 240

Asp Gly Pro Arg His Pro Ile Ala Gly Ile Asp Pro Thr Pro Cys Thr
                245                 250                 255

Pro Gln Leu Gly Glu Pro Gly Pro Trp Tyr Asp Arg Leu Pro His Phe
            260                 265                 270

Arg Leu Glu Phe Thr Pro Ser Val Gly Glu Glu Leu Gln Ser Glu Tyr
        275                 280                 285

Leu Val Asp Arg Asp Asp Ala Val Asp Ala Ile Arg Ala Val Gln Asp
    290                 295                 300

Leu Ala Pro Arg Ile Ala Pro Leu Leu Phe Val Cys Glu Ile Arg Thr
305                 310                 315                 320

Met Ala Ser Asp Gly Leu Trp Leu Ser Pro Ala Gln Gly Arg Asp Thr
                325                 330                 335

Val Gly Leu His Phe Thr Trp Arg Pro Asp Glu Ser Ala Val Arg Gln
            340                 345                 350

Leu Leu Pro Glu Ile Glu Arg Ala Leu Pro Ala Ser Ala Arg Pro His
        355                 360                 365

Trp Gly Lys Val Phe Thr Leu Pro Gly His Asp Val Ala Ala Arg Tyr
    370                 375                 380
```

-continued

```
Pro Arg Trp Ala Asp Phe Val Ala Leu Arg Arg Arg Leu Asp Pro Glu
385                 390                 395                 400

Arg Arg Phe Ala Asn Ala Tyr Leu Glu Arg Leu Gly Leu
                405                 410


<210> SEQ ID NO 45
<211> LENGTH: 420
<212> TYPE: PRT
<213> ORGANISM: Streptomyces sp.

<400> SEQUENCE: 45

Met Thr Pro Ala Glu Lys Asn Trp Ala Gly Asn Ile Thr Phe Gly Ala
1               5                   10                  15

Lys Arg Leu Cys Val Pro Arg Ser Val Arg Glu Leu Arg Glu Thr Val
            20                  25                  30

Ala Ala Ser Gly Ala Val Arg Pro Leu Gly Thr Arg His Ser Phe Asn
        35                  40                  45

Thr Val Ala Asp Thr Ser Gly Asp His Val Ser Leu Ala Gly Leu Pro
    50                  55                  60

Arg Val Val Asp Ile Asp Val Pro Gly Arg Ala Val Ser Leu Ser Ala
65                  70                  75                  80

Gly Leu Arg Phe Gly Glu Phe Ala Ala Glu Leu His Ala Arg Gly Leu
                85                  90                  95

Ala Leu Ala Asn Leu Gly Ser Leu Pro His Ile Ser Val Ala Gly Ala
            100                 105                 110

Val Ala Thr Gly Thr His Gly Ser Gly Val Gly Asn Arg Ser Leu Ala
        115                 120                 125

Gly Ala Val Arg Ala Leu Ser Leu Val Thr Ala Asp Gly Glu Thr Arg
    130                 135                 140

Thr Leu Arg Arg Thr Asp Glu Asp Phe Ala Gly Ala Val Val Ser Leu
145                 150                 155                 160

Gly Ala Leu Gly Val Val Thr Ser Leu Glu Leu Asp Leu Val Pro Ala
                165                 170                 175

Phe Glu Val Arg Gln Trp Val Tyr Glu Asp Leu Pro Glu Ala Thr Leu
            180                 185                 190

Ala Ala Arg Phe Asp Glu Val Met Ser Ala Ala Tyr Ser Val Ser Val
        195                 200                 205

Phe Thr Asp Trp Arg Pro Gly Pro Val Gly Gln Val Trp Leu Lys Gln
    210                 215                 220

Arg Val Gly Asp Glu Gly Ala Arg Ser Val Met Pro Ala Glu Trp Leu
225                 230                 235                 240

Gly Ala Arg Leu Ala Asp Gly Pro Arg His Pro Val Pro Gly Met Pro
                245                 250                 255

Ala Gly Asn Cys Thr Ala Gln Gln Gly Val Pro Gly Pro Trp His Glu
            260                 265                 270

Arg Leu Pro His Phe Arg Met Glu Phe Thr Pro Ser Asn Gly Asp Glu
        275                 280                 285

Leu Gln Ser Glu Tyr Phe Val Ala Arg Ala Asp Ala Val Ala Ala Tyr
    290                 295                 300

Glu Ala Leu Ala Arg Leu Arg Asp Arg Ile Ala Pro Val Leu Gln Val
305                 310                 315                 320

Ser Glu Leu Arg Thr Val Ala Ala Asp Asp Leu Trp Leu Ser Pro Ala
                325                 330                 335

His Gly Arg Asp Ser Val Ala Phe His Phe Thr Trp Val Pro Asp Ala
            340                 345                 350
```

-continued

```
Ala Ala Val Ala Pro Val Ala Gly Ala Ile Glu Glu Ala Leu Ala Pro
        355                 360                 365

Phe Gly Ala Arg Pro His Trp Gly Lys Val Phe Ser Thr Ala Pro Glu
    370                 375                 380

Val Leu Arg Thr Leu Tyr Pro Arg Tyr Ala Asp Phe Glu Glu Leu Val
385                 390                 395                 400

Gly Arg His Asp Pro Glu Gly Thr Phe Arg Asn Ala Phe Leu Asp Arg
                405                 410                 415

Tyr Phe Arg Arg
            420


<210> SEQ ID NO 46
<211> LENGTH: 419
<212> TYPE: PRT
<213> ORGANISM: Paenibacillus sp.

<400> SEQUENCE: 46

Met Gly Asp Lys Leu Asn Trp Ala Gly Asn Tyr Arg Tyr Arg Ser Met
1               5                   10                  15

Glu Leu Leu Glu Pro Lys Ser Leu Glu Glu Val Lys Asp Leu Val Val
            20                  25                  30

Ser Arg Thr Ser Ile Arg Val Leu Gly Ser Cys His Ser Phe Asn Gly
        35                  40                  45

Ile Ala Asp Thr Gly Gly Ser His Leu Ser Leu Arg Lys Met Asn Arg
    50                  55                  60

Val Ile Asp Leu Asp Arg Val Gln Arg Thr Val Thr Val Glu Gly Gly
65                  70                  75                  80

Ile Arg Tyr Gly Asp Leu Cys Arg Tyr Leu Asn Asp His Gly Tyr Ala
                85                  90                  95

Leu His Asn Leu Ala Ser Leu Pro His Ile Ser Val Ala Gly Ala Val
            100                 105                 110

Ala Thr Ala Thr His Gly Ser Gly Asp Leu Asn Ala Ser Leu Ala Ser
        115                 120                 125

Ser Val Arg Ala Ile Glu Leu Met Lys Ser Asp Gly Glu Val Thr Val
    130                 135                 140

Leu Thr Arg Gly Thr Asp Pro Glu Phe Asp Gly Ala Val Val Gly Leu
145                 150                 155                 160

Gly Gly Leu Gly Val Val Thr Lys Leu Lys Leu Asp Leu Val Pro Ser
                165                 170                 175

Phe Gln Val Ser Gln Thr Val Tyr Asp Arg Leu Pro Phe Ser Ala Leu
            180                 185                 190

Asp His Gly Ile Asp Glu Ile Leu Ser Ser Ala Tyr Ser Val Ser Leu
        195                 200                 205

Phe Thr Asp Trp Ala Glu Pro Ile Phe Asn Gln Val Trp Val Lys Arg
    210                 215                 220

Lys Val Gly Ile Asn Gly Glu Asp Glu Thr Ser Pro Asp Phe Phe Gly
225                 230                 235                 240

Ala Leu Pro Ala Pro Glu Lys Arg His Met Val Leu Gly Gln Ser Val
                245                 250                 255

Val Asn Cys Ser Glu Gln Met Gly Asp Pro Gly Pro Trp Tyr Glu Arg
            260                 265                 270

Leu Pro His Phe Arg Met Glu Phe Thr Pro Ser Ala Gly Asn Glu Leu
        275                 280                 285

Gln Ser Glu Tyr Phe Val Pro Arg Arg His Ala Val Glu Ala Met Arg
```

```
    290                 295                 300

Ala Leu Gly Lys Leu Arg Asp Arg Ile Ala Pro Leu Leu Phe Ile Ser
305                 310                 315                 320

Glu Ile Arg Thr Ile Ala Ser Asp Thr Phe Trp Met Ser Pro Cys Tyr
                325                 330                 335

Arg Gln Asp Ser Val Gly Leu His Phe Thr Trp Lys Pro Asp Trp Glu
            340                 345                 350

Arg Val Arg Gln Leu Leu Pro Leu Ile Glu Arg Glu Leu Glu Pro Phe
        355                 360                 365

Ala Ala Arg Pro His Trp Ala Lys Leu Phe Thr Met Glu Ser Glu Met
    370                 375                 380

Ile Gln Ala Arg Tyr Glu Arg Leu Ala Asp Phe Arg Gln Leu Leu Leu
385                 390                 395                 400

Arg Tyr Asp Pro Ile Gly Lys Phe Arg Asn Thr Phe Leu Asp His Tyr
                405                 410                 415

Ile Met His


<210> SEQ ID NO 47
<211> LENGTH: 1356
<212> TYPE: DNA
<213> ORGANISM: Terriglobuds roseus

<400> SEQUENCE: 47

atggatcgtc gtgaactgct gaaaacctct gcactgctga tggcagcagc accgttagca      60

cgtgcagcaa atgttccgga agatcatgca aatgttccgc gtaccaattg gagcaaaaac     120

ttccactata gcaccagccg cgtttatgca ccgactaccc cggaagaagt tccggcaatt     180

gttctggaaa atggtcatct gaaaggtctg ggttctcgtc actgcttcaa caacatcgcc     240

gatagccagt atgcgcagat cagcatgcgc gaagttaaag gcattcagat cgatgaagcc     300

gcacaaaccg ttaccgtggg tgcaggtatt gcgtatggtg aattagcacc ggtgctggat     360

aaagcgggtt ttgcactggc aaatttagca agtttaccgc atatcagcgt gggtggcacc     420

attgcaaccg caacacatgg ctctggcgtt ggtaacaaaa acctgtcttc tgcaacccgt     480

gcaattgaaa tcgtgaaagc ggatggcagc attctgcgtc tgtcgcgtga tactgatggt     540

gaacgttttc gtatggcggt ggttcatctg ggtgcattag gtgttttaac caaagttacc     600

ctggatatcg tgccgcgctt cgatatgtct caggtggtgt atcgcaacct gtcctttgat     660

cagctggaac acaacctgga taccattctg agctctggct atagcgttag cctgttcacc     720

gactggcagc gtaatcgtgt taatcaggtg tggatcaaag ataaagcgac cgcggatgca     780

ccgcaaaaac cgttacctcc gatgttttat ggtgcgaccc tgcaaaccgc aaaactgcat     840

ccgatcgatg atcatccggc agatgcatgt accgaacaaa tgggtagtgt tggtccgtgg     900

tatttacgtc tgccgcattt caaaatggag tttaccccga gcagcggtga agaattacag     960

accgaatact tcgtggcgcg caaagatggc tatcgcgcaa ttcgtgccgt ggaaaaactg    1020

cgcgataaaa ttaccccgca cctgtttatc accgaaatcc gcaccattgc agcagatgat    1080

ctgccgatga gcatggcata tcaacgtgac agtatggcga ttcattttac ctggaaaccg    1140

gaagaaccga ccgtgcgtaa attactgccg gaaatcgaag cagcactggc gccgtttggt    1200

gttcgtccgc attggggcaa aatttttgaa attccgccga gctatctgca taaacagtat    1260

ccggcactgc cgcgttttcg cgcaatggca caggcattag atcctggtgg caaatttcgt    1320

aatgcatatc tggatcgtaa catctttggc gcgtag                              1356
```

-continued

<210> SEQ ID NO 48
<211> LENGTH: 1353
<212> TYPE: DNA
<213> ORGANISM: Granulicella mallensis

<400> SEQUENCE: 48
atggacaaac gcgatttcct gaaaggtagc gcaaccaccg cagttgcact gatgatgggt 60
ctgaatgaaa gcaaagcgtt tgcggatgat agcgttccgc gtaccaattg gagcggcaac 120
taccattata gcaccaacaa agtgctgcag ccggcaagtg ttgcagaaac ccaagatgca 180
gttcgtagtg ttgcaggtgt tcgtgcatta ggtactcgtc atagctttaa cggcatcgcg 240
gatagccaga ttgcccagat tagtaccctg aaactgaaag atgtgagcct ggatgcgaaa 300
agctcgaccg tgaccgttgg tgcaggtatt cgttatggtg atctggcggt tcagctggat 360
gcgaaaggtt ttgctctgca taatctggca agtctgccgc atatttctgt tggtggtgca 420
tgtgcaactg cgacccatgg ttcaggtatg ggtaatggta atttagcaac cgcagttaaa 480
gcggtggaat ttgttgcggc ggatggtagc gtgcataccc tgtctcgtga tcgtgatggt 540
gatcgttttg cgggctctgt tgttggtctg ggtgcattag gtgttgttac ccatttaacc 600
ctgcaagttc agccacgttt cgaaatgacc caggtggtgt accgtgatct gccatttagt 660
gaactggaac atcatctgcc ggaaattatg ggtgccggtt atagcgtgtc cctgtttacc 720
gattggcaga atggtcgtgc aggtgaagtg tggatcaaac gtcgcgtgga tcaaggtggt 780
gcaagtgctc ctccagctcg ttttttttaat gcaaccttag caaccaccaa actgcacccg 840
atcctggatc atcctgctga agcatgtacc gatcagttaa ataccgtagg tccgtggtat 900
gaacgtttac cgcacttcaa actgaacttc accccgagca gtggccaaga attacagacc 960
gagtttttcg tgccgttcga tcgcggctat gacgccattc gtgccgttga aactttacgt 1020
gatgtgatta ccccgcacct gtatatcacc gaactgcgtg cagttgcagc tgatgattta 1080
tggatgagca tggcatatca acgtccgagt ctggcaatcc attttacctg gaaaccggaa 1140
accgatgcag tgctgaaatt actgccgcag attgaagcga aactggcccc gtttggtgct 1200
cgtccgcatt gggcaaaagt tttaccatg aaaagcagcc atgtggcacc gctgtatccg 1260
cgcctgaaag attttctggt tctggcaaaa tcctttgatc cgaaaggcaa attccaaaac 1320
gcgtttctgc aggaccatgt ggacatcgca tag 1353

<210> SEQ ID NO 49
<211> LENGTH: 1245
<212> TYPE: DNA
<213> ORGANISM: Streptomyces acidiscabies

<400> SEQUENCE: 49
atgaccgcat ctgtgaccaa ttgggcgggt aacatcagct ttgtggcgaa agatgttgtt 60
cgtccgggtg gtgttgaagc actgcgtaaa gttgttgcgg gtaatgatcg tgttcgtgtt 120
ctgggttctg gtcatagctt taaccgtatc gctgaaccgg gtgctgatgg tgttctggtt 180
agcctggatg cattaccgca agtgattgat gttgataccg aacgtcgtac cgtgcgtgtt 240
ggtggtggtg ttaaatacgc ggaactggct cgtcatgtga atgaatctgg tctggcactg 300
ccgaatatgg catctctgcc gcatatttct gttgcaggtt ctgttgcaac tggtacccat 360
ggttctggtg tgaataatgg cccgttagca accccggttc gtgaagttga attattaacc 420
gcggatggct ctctggtgac catcggtaaa gatgatgcgc gttttccggg tgcagttact 480
tctctgggtg cgctgggtgt tgttgttgca ctgaccttag atttagaacc ggcgtatggt 540

-continued gttgaacagt ataccttac cgaattaccg ctggaaggtc tggacttcga agcagttgcg 600
agtgcagcat attctgttag cctgttcacc gattggcgtg aagctggttt tcgccaagtt 660
tgggtgaaac gccgcattga tgaaccgtac gcgggctttc cgtgggcagc accggcaact 720
gaaaaattac atccggttcc gggtatgcca gcagaaaatt gtactgatca atttggtgca 780
gcaggtccat ggcatgaacg tttaccgcat tttaaagcgg aatttacccc gtctagcggt 840
gatgaattac agagcgaata tctgctgccg cgtgaacatg cactggcggc actggatgca 900
gtgggcaacg tgcgtgaaac cgtttctacc gtgctgcaga tttgcgaagt tcgtaccatt 960
gcagcagata cccagtggtt aagtccggct tatggtcgtg atagtgttgc attacatttt 1020
acttggaccg atgatatgga tgcagtttta cctgcagttc gtgccgttga aagcgcgctg 1080
gatggctttg gtgctcgccc gcattggggt aaagtgttta ccaccgcacc ggcagcatta 1140
cgtgaacgtt atccgcgtct ggatgatttt cgtaccctgc gtgatgaatt agatccggca 1200
ggcaaattta ctaatgcatt tgttcgtgat gttctggaag gttag 1245

<210> SEQ ID NO 50
<211> LENGTH: 1284
<212> TYPE: DNA
<213> ORGANISM: Actinomycetales

<400> SEQUENCE: 50
atgaccctgg aacgtaattg ggcaggtacc catacctttg cagcaccgcg tattgttaat 60
gcaaccagca tcgatgaagt tcgtgcgtta gtggcagaag cagcacgtac cggtacccgt 120
gttcgtgcat taggtactcg tcattctttt accgatctgg cagatagcga tggtaccctg 180
attaccgtgc tggatattcc ggcagatcca gttttcgatg aagcagcagg tagcgttacc 240
attggtgcag gtacccgtta tggtattgca gcagcatggt tagcagaaca tggtctggcg 300
tttcacaaca tgggtagcct gccgcatatt agcgttggtg gtgcaattgc aaccggtacc 360
catggtagtg gtaatgataa cggcattctg agtagcgcag ttagtggtct ggaatatgtt 420
gatgcgaccg gtgaactggt tcatgtgcgt cgtggtgatc ctggttttga tggtctggtt 480
gttggtttag gcgcgtatgg tattgtggtt cgtgtgacgg tggatgttca accggcatat 540
cgtgttcgcc aggatgtgta tcgtgatgtt ccgtgggatg cagttctggc agattttgaa 600
ggtgttacag gtggtgcgta tagcgttagc atctttacca actggctggg tgatacggtg 660
gaacagattt ggtggaaaac ccgtctggtt gcaggtgatg atgaactgcc ggtggttccg 720
gaaagctggc tgggtgttca acgtgattct ttaaccgcag gtaatctggt tgaaaccgat 780
ccggataatt taaccctgca aggtggtgtt ccgggtgatt ggtgggaacg tttaccgcat 840
tttcgtctgg aaagtacccc gtctaatggt gatgaaatcc agaccgaata cttcatcgat 900
cgcgcggatg gtccggcggc aattaccgca ctgcgtgcat taggtgatcg tattgctccg 960
ttactgttag ttaccgaatt acgtaccgca gctccagata aactgtggct gagtggcgca 1020
tatcatcgcg aaatgttagc ggtccatttt acctggcgta atttaccgga agaagtgcgt 1080
gcagttttac cagcgatcga agaagccctg gcgccgtttg atgctcgtcc gcattggggt 1140
aaactgaatc tgttaaccgc agaacgtatt gcagaagttg ttccgcgtct ggctgatgca 1200
cgtgatctgt ttgaagaact ggacccggct ggtacctttt ctaatgctca tctggaacgt 1260
attggtgttc gtttaccgcg ttag 1284

<210> SEQ ID NO 51

-continued

<211> LENGTH: 1260
<212> TYPE: DNA
<213> ORGANISM: Frankia sp.

<400> SEQUENCE: 51

```
atgcgtgatg cagcagcagc aaattgggca ggtaatgtgc gttttggtgc agcacgtgtt     60
gttgcaccgg aaagtgttgg tgaactgcag gaaattgttg caggtagccg taaagcacgt    120
gcattaggta ccggtcatag ctttagccgt attgcagata ccgatggtac cctgattgct    180
accgcacgtt taccacgtcg tattcagatc gatgatggca gcgttaccgt ttctggtggt    240
atccgttatg gcgatctggc ccgtgaatta gcaccgaatg gttgggcatt acgtaatctg    300
ggttctttac cgcacatttc agttgcaggt gcatgtgcaa ccggtaccca tggttcaggt    360
gatcgtaatg gtagtctggc aacctctgtt gcagcgttag aattagttac cgcgtctggt    420
gaattagtga gcgttcgtcg tggcgatgaa gatttcgatg gccatgtgat tgcgctgggt    480
gcactgggtg ttactgttgc agttaccctg gatttagttc cgggttttca ggttcgtcag    540
ctggtgtatg aaggtctgac ccgtgatacc ttactggaaa gtgtgcagga aatctttgct    600
gcgagctata gtgttagcgt gtttaccggt tgggacccgg aaagttctca actgtggctg    660
aaacagcgcg ttgatggtcc gggcgatgat ggtgaaccac cggcagaacg ttttggtgca    720
cgtttagcaa ctcgtccgtt acatccagtt ccgggtattg atccgactca tactactcaa    780
caattaggtg ttccaggtcc gtggcatgaa cgtttaccgc attttcgtct ggattttacc    840
ccttctgcag gtgatgaact gcaaaccgaa tacttcgtgg cccgcgaaca tgcagcggcg    900
gcgattgaag cactgtttgc gattggtgcg gttgttcgtc cggcattaca aattagcgaa    960
attcgtaccg ttgcagctga tgcattatgg ctgtctccgg catatcgtcg tgatgttatg   1020
gcgttacatt ttacctggat tagcgcagaa ggtaccgtta tgccagcagt tgcagcagtg   1080
gaacgtgcac tggcgccgtt tgatccggtt cctcattggg gtaaagtttt tgcgctgccg   1140
ccagcagcag ttcgtgctgg ttatcctcgt gcagcagaat tttagcatt agcagctcgt     1200
cgtgatccgg aagcagtttt tcgtaatcag tatttagatg catatttacc ggcagcatag   1260
```

<210> SEQ ID NO 52
<211> LENGTH: 1242
<212> TYPE: DNA
<213> ORGANISM: Propionibacteriacaeae

<400> SEQUENCE: 52

```
atgacccagc gtaattgggc gggtaatgtg agctatagta gcagccgtgt tgcagaacca     60
gcaagtgtgg atgatttaac cgcactggtt gaaagtgaac cgcgtgttcg tccgttaggt    120
agtcgtcatt gcttcaacga tatcgccgat accccaggtg ttcatgtttc tctggcacgt    180
ctgcgtggtg aagaaccgcg tttaacagca ccgggtacct tacgtactcc agcttggtta    240
cgttatggtg atttagttcc ggttctgcgt gaagcaggtg cagcattagc aaatttagca    300
tctctgccgc atattagcgt tgcaggtgca gttcaaaccg gtacccatgg ttcaggtgat    360
cgtattggca ctctggcaac ccaagttagc gccctggaat tagtgaccgg caccggtgaa    420
gttttacgct tagaacgtgg tgaacctgat tttgatggtg cggttgttgg tttaggtgcg    480
ttaggtgttc tgactcatgt ggaattagat gttagtccgg cgcgtgatgt tgcacagcac    540
gtgtatgaag gtgttcgtct ggatgatgtt ctggcggatt taggcgcggt tactggcgca    600
ggtgattcgg tgagcatgtt tacccattgg caagatccgg cagttgttag tcaggtttgg    660
gttaaaagtg gcggtgatgt ggatgatgca gcaattcgtg atgcaggtgg tcgtccggca    720
```

gatggtccgc gtcatccaat tgcaggtatt gatccgactc catgtactcc acaattaggt 780
gaaccaggtc cgtggtatga tcgtctgccg cattttcgtc tggaatttac cccgagtgtt 840
ggtgaagaac tgcaaagtga atatctggtt gatcgcgatg atgccgttga tgcaattcgt 900
gcggtgcagg atttagcccc gcgtattgcg ccgctgctgt ttgtttgcga aattcgtacc 960
atggcaagtg atggtttatg gctgagcccg gcacaaggtc gtgataccgt tggtctgcat 1020
tttacctggc gtcctgatga atctgcagtt cgtcaattat taccggaaat tgaacgtgct 1080
ttaccggcaa gtgctcgtcc gcattggggt aaagtgttta ccctgccggg ccatgatgtt 1140
gcagcacgtt atccgcgttg ggcagatttt gttgcattac gtcgtcgttt agatccggaa 1200
cgtcgtttcg cgaatgcata cctggaacgt ttaggtctgt ag 1242

<210> SEQ ID NO 53
<211> LENGTH: 1263
<212> TYPE: DNA
<213> ORGANISM: Streptomyces sp.

<400> SEQUENCE: 53
atgactccgg cggaaaaaaa ttgggcgggc aacatcacct ttggtgcaaa acgtctgtgt 60
gttccgcgtt ctgttcgtga actgcgtgaa accgttgcag catctggtgc agttcgtccg 120
ttaggtactc gtcatagctt taataccgtt gcagatacca gtggtgatca tgttagtctg 180
gcaggtttac cgcgtgttgt ggacatcgat gttccgggtc gtgcagtttc tctgtctgct 240
ggtctgcgtt ttggtgaatt tgcggctgaa ttacatgcac gtggtctggc gctggcaaat 300
ttaggttctc tgccgcatat tagcgttgca ggtgcagttg caaccggtac tcatggttct 360
ggtgttggta atcgttcttt agcaggtgca gttcgtgctt tatctctggt aaccgccgat 420
ggtgaaaccc gtaccttacg tcgtaccgat gaagattttg caggtgcagt ggtttctctg 480
ggtgcactgg gtgttgttac ttctctggaa ctggatttag ttccggcgtt cgaagtgcgt 540
cagtgggtgt acgaagatct gccggaagca actttagcag ctcgttttga tgaagttatg 600
tcagcagcgt atagcgtgtc cgtgttcacc gattggcgtc cgggtcctgt tggtcaagtt 660
tggctgaaac aacgtgttgg tgatgaaggt gctcgtagtg ttatgccagc agaatggtta 720
ggtgcacgtt tagcagatgg tccgcgtcat ccagttccag gtatgcctgc aggtaattgt 780
acagcacaac aaggtgttcc aggtccgtgg catgaacgtt taccgcattt tcgcatggaa 840
tttaccccgt ctaacggcga tgaactgcaa agcgaatatt ttgtggcgcg tgcagatgca 900
gttgcagcgt atgaagcatt agcacgtctg cgtgatcgta ttgcgccggt tctgcaagtt 960
agcgaattac gtaccgttgc agcagatgat ctgtggctga gtccggcaca tggtcgtgat 1020
agtgttgcgt ttcattttac ctgggttccg gatgcagcag cagttgcacc ggttgcaggt 1080
gctattgaag aagcattagc accgtttggt gcacgtccac attggggtaa agtttttagc 1140
accgcaccgg aagttttacg taccttatat ccgcgttatg ccgatttcga agaactggtg 1200
ggccgccatg atccggaagg cacctttcgt aatgcatttt tagatcgcta ctttcgtcgc 1260
tag 1263

<210> SEQ ID NO 54
<211> LENGTH: 1260
<212> TYPE: DNA
<213> ORGANISM: Paenibacillus sp.

<400> SEQUENCE: 54

-continued

```
atgggcgata aactgaattg ggcgggcaac tatcgttatc gcagcatgga actgctggaa      60

ccgaaaagcc tggaagaagt gaaagatctg gtggttagcc gtaccagcat tcgtgttctg     120

ggtagctgtc atagctttaa cggcattgcg gataccggtg gtagtcatct gagtctgcgc     180

aaaatgaacc gcgtgattga tctggatcgt gttcagcgta ccgttaccgt tgaaggtggt     240

attcgttacg gtgatctgtg ccgctatctg aacgatcatg gttatgccct gcataatctg     300

gcaagcttac cgcacatcag cgttgcaggt gcagttgcaa ccgcaaccca tggttctggt     360

gatctgaatg caagtctggc aagctctgtt cgtgcaattg aactgatgaa aagcgatggc     420

gaagttacgg ttctgacccg tggtaccgat ccggaatttg atggtgcagt tgttggtctg     480

ggtggtttag gtgttgtgac caaactgaaa ctggatctgg ttccgagctt tcaggtgtcg     540

cagaccgtgt atgatcgtct gccgtttagc gcactggatc atggcatcga tgaaattctg     600

agtagtgcat atagcgttag cctgttcacc gattgggcgg aaccgatctt taatcaggtg     660

tgggtgaaac gcaaagtggg cattaacggc gaagatgaaa ccagtccgga ttttttggc      720

gcattaccgg caccggaaaa acgccacatg gttctgggtc agagcgtggt gaattgcagc     780

gaacaaatgg gtgatcctgg tccgtggtat gaacgtttac cgcattttcg catggaattt     840

accccgagtg caggcaatga attacagagc gaatattttg tgccgcgtcg tcatgcggtt     900

gaagcaatgc gtgcgttagg taaactgcgt gatcgtattg caccactgct gttcatcagc     960

gaaatccgca ccattgcgag cgataccttc tggatgagcc cgtgttatcg tcaggattct    1020

gttggtctgc attttacctg gaaaccggat tgggaacgtg ttcgtcagtt attaccgctg    1080

attgaacgtg aactggaacc gtttgcggca cgtccgcatt gggcgaaact gtttaccatg    1140

gaaagcgaaa tgattcaggc gcgctatgaa cgtctggcgg attttcgtca gctgctgctg    1200

cgttatgatc cgattggcaa attccgtaac acctttctgg atcactacat catgcactaa    1260


<210> SEQ ID NO 55
<211> LENGTH: 205
<212> TYPE: PRT
<213> ORGANISM: Thermus thermophilus

<400> SEQUENCE: 55

Met Glu Ala Thr Leu Pro Val Leu Asp Ala Lys Thr Ala Ala Leu Lys
1               5                   10                  15

Arg Arg Ser Ile Arg Arg Tyr Arg Lys Asp Pro Val Pro Glu Gly Leu
            20                  25                  30

Leu Arg Glu Ile Leu Glu Ala Ala Leu Arg Ala Pro Ser Ala Trp Asn
        35                  40                  45

Leu Gln Pro Trp Arg Ile Val Val Val Arg Asp Pro Ala Thr Lys Arg
    50                  55                  60

Ala Leu Arg Glu Ala Ala Phe Gly Gln Ala His Val Glu Glu Ala Pro
65                  70                  75                  80

Val Val Leu Val Leu Tyr Ala Asp Leu Glu Asp Ala Leu Ala His Leu
                85                  90                  95

Asp Glu Val Ile His Pro Gly Val Gln Gly Glu Arg Arg Glu Ala Gln
            100                 105                 110

Lys Gln Ala Ile Gln Arg Ala Phe Ala Ala Met Gly Gln Glu Ala Arg
        115                 120                 125

Lys Ala Trp Ala Ser Gly Gln Ser Tyr Ile Leu Leu Gly Tyr Leu Leu
    130                 135                 140

Leu Leu Leu Glu Ala Tyr Gly Leu Gly Ser Val Pro Met Leu Gly Phe
145                 150                 155                 160
```

```
Asp Pro Glu Arg Val Lys Ala Ile Leu Gly Leu Pro Ser His Ala Ala
                165                 170                 175

Ile Pro Ala Leu Val Ala Leu Gly Tyr Pro Ala Glu Glu Gly Tyr Pro
            180                 185                 190

Ser His Arg Leu Pro Leu Glu Arg Val Val Leu Trp Arg
        195                 200                 205


<210> SEQ ID NO 56
<211> LENGTH: 618
<212> TYPE: DNA
<213> ORGANISM: Thermus thermophilus

<400> SEQUENCE: 56

atggaagcaa ccttaccggt gttagacgcg aaaaccgcag cactgaaacg tcgtagcatt      60

cgccgttatc gcaaagatcc agttccggaa ggtttactgc gcgaaattct ggaagcagca     120

ttacgtgcac cgtctgcatg gaatttacaa ccgtggcgta ttgtggtggt tcgtgatccg     180

gcaactaaac gtgcattacg tgaagcagca tttggtcaag cccatgtgga agaagcaccg     240

gttgttctgg ttctgtacgc agatctggaa gatgcactgg cacatctgga tgaagtgatt     300

catccgggcg ttcaaggtga acgtcgtgaa gcgcagaaac aagcaattca gcgtgcattt     360

gcagcaatgg gtcaggaagc tcgtaaagct tgggcaagcg gtcaaagtta tattctgctg     420

ggttatctgc tgctgctgct ggaagcatat ggtctgggtt ctgttccgat gctgggtttt     480

gatcctgaac gtgttaaagc gattctgggc ctgccgtcac atgcagcgat tccggcatta     540

gttgcactgg gttatccggc tgaagaaggt tatccgagtc atcgtttacc gctggaacgt     600

gttgttttat ggcgttga                                                   618


<210> SEQ ID NO 57
<211> LENGTH: 247
<212> TYPE: PRT
<213> ORGANISM: Agrobacterium sp.

<400> SEQUENCE: 57

Met Lys Asn Pro Phe Ser Leu Gln Gly Arg Lys Ala Leu Val Thr Gly
1               5                   10                  15

Ala Asn Thr Gly Leu Gly Gln Ala Ile Ala Val Gly Leu Ala Ala Ala
            20                  25                  30

Gly Ala Glu Val Val Cys Ala Ala Arg Arg Ala Pro Asp Glu Thr Leu
        35                  40                  45

Glu Met Ile Ala Ser Asp Gly Gly Lys Ala Ser Ala Leu Ser Ile Asp
    50                  55                  60

Phe Ala Asp Pro Leu Ala Ala Lys Asp Ser Phe Ala Gly Ala Gly Phe
65                  70                  75                  80

Asp Ile Leu Val Asn Asn Ala Gly Ile Ile Arg Arg Ala Asp Ser Val
                85                  90                  95

Glu Phe Ser Glu Leu Asp Trp Asp Glu Val Met Asp Val Asn Leu Lys
            100                 105                 110

Ala Leu Phe Phe Thr Thr Gln Ala Phe Ala Lys Glu Leu Leu Ala Lys
        115                 120                 125

Gly Arg Ser Gly Lys Val Val Asn Ile Ala Ser Leu Leu Ser Phe Gln
    130                 135                 140

Gly Gly Ile Arg Val Pro Ser Tyr Thr Ala Ala Lys His Gly Val Ala
145                 150                 155                 160

Gly Leu Thr Lys Leu Leu Ala Asn Glu Trp Ala Ala Lys Gly Ile Asn
```

-continued

```
                165                 170                 175

Val Asn Ala Ile Ala Pro Gly Tyr Ile Glu Thr Asn Asn Thr Glu Ala
            180                 185                 190

Leu Arg Ala Asp Ala Ala Arg Asn Lys Ala Ile Leu Glu Arg Ile Pro
        195                 200                 205

Ala Gly Arg Trp Gly Arg Ser Glu Asp Ile Ala Gly Ala Ala Val Phe
    210                 215                 220

Leu Ser Ser Ala Ala Ala Asp Tyr Val His Gly Ala Ile Leu Asn Val
225                 230                 235                 240

Asp Gly Gly Trp Leu Ala Arg
                245


<210> SEQ ID NO 58
<211> LENGTH: 198
<212> TYPE: PRT
<213> ORGANISM: Agrobacterium tumefaciens

<400> SEQUENCE: 58

Met Ile Ala Gly Val Gly Gly Glu Ala Arg Glu Leu Ala Leu Asp Leu
1               5                   10                  15

Ser Asp Pro Met Ala Ala Lys Asp Val Phe Ala Glu Gly Ala Tyr Asp
            20                  25                  30

Leu Leu Ile Asn Asn Ala Gly Ile Ile Arg Arg Ala Asp Ala Val Asp
        35                  40                  45

Phe Ser Glu Asp Asp Trp Asp Ala Val Met Asp Val Asn Leu Lys Ala
    50                  55                  60

Val Phe Phe Thr Ser Gln Ala Phe Ala Arg Ala Leu Met Ser Arg Asn
65                  70                  75                  80

Ala Ser Gly Lys Ile Val Asn Ile Ala Ser Leu Leu Ser Phe Gln Gly
                85                  90                  95

Gly Ile Arg Val Ala Ser Tyr Thr Ala Ala Lys His Gly Val Ala Gly
            100                 105                 110

Ile Thr Arg Leu Leu Ala Asn Glu Trp Ala Ser Arg Gly Ile Asn Val
        115                 120                 125

Asn Ala Ile Ala Pro Gly Tyr Ile Ala Thr Asn Asn Thr Glu Ala Leu
    130                 135                 140

Arg Ala Asp Glu Glu Arg Asn Ala Ala Ile Leu Ala Arg Ile Pro Ala
145                 150                 155                 160

Gly Arg Trp Gly Arg Ala Glu Asp Ile Ala Gly Thr Ala Val Tyr Leu
                165                 170                 175

Cys Ser Pro Ala Ala Asp Tyr Val His Gly Ala Ile Leu Asn Val Asp
            180                 185                 190

Gly Gly Trp Leu Ala Arg
        195


<210> SEQ ID NO 59
<211> LENGTH: 253
<212> TYPE: PRT
<213> ORGANISM: Escherichia coli

<400> SEQUENCE: 59

Met Ile Leu Ser Ala Phe Ser Leu Glu Gly Lys Val Ala Val Val Thr
1               5                   10                  15

Gly Cys Asp Thr Gly Leu Gly Gln Gly Met Ala Leu Gly Leu Ala Gln
            20                  25                  30

Ala Gly Cys Asp Ile Val Gly Ile Asn Ile Val Glu Pro Thr Glu Thr
```

-continued

```
        35                  40                  45

Ile Glu Gln Val Thr Ala Leu Gly Arg Arg Phe Leu Ser Leu Thr Ala
    50                  55                  60

Asp Leu Arg Lys Ile Asp Gly Ile Pro Ala Leu Leu Asp Arg Ala Val
65                  70                  75                  80

Ala Glu Phe Gly His Ile Asp Ile Leu Val Asn Asn Ala Gly Leu Ile
                85                  90                  95

Arg Arg Glu Asp Ala Leu Glu Phe Ser Glu Lys Asp Trp Asp Asp Val
            100                 105                 110

Met Asn Leu Asn Ile Lys Ser Val Phe Phe Met Ser Gln Ala Ala Ala
        115                 120                 125

Lys His Phe Ile Ala Gln Gly Asn Gly Gly Lys Ile Ile Asn Ile Ala
    130                 135                 140

Ser Met Leu Ser Phe Gln Gly Gly Ile Arg Val Pro Ser Tyr Thr Ala
145                 150                 155                 160

Ser Lys Ser Gly Val Met Gly Val Thr Arg Leu Met Ala Asn Glu Trp
                165                 170                 175

Ala Lys His Asn Ile Asn Val Asn Ala Ile Ala Pro Gly Tyr Met Ala
            180                 185                 190

Thr Asn Asn Thr Gln Gln Leu Arg Ala Asp Glu Gln Arg Ser Ala Glu
        195                 200                 205

Ile Leu Asp Arg Ile Pro Ala Gly Arg Trp Gly Leu Pro Ser Asp Leu
    210                 215                 220

Met Gly Pro Ile Val Phe Leu Ala Ser Ser Ala Ser Asp Tyr Val Asn
225                 230                 235                 240

Gly Tyr Thr Ile Ala Val Asp Gly Gly Trp Leu Ala Arg
                245                 250


<210> SEQ ID NO 60
<211> LENGTH: 254
<212> TYPE: PRT
<213> ORGANISM: Sphingomonas sp.

<400> SEQUENCE: 60

Met Pro Gly Met Thr Thr Pro Phe Asp Leu His Gly Lys Thr Ala Ile
1               5                   10                  15

Val Thr Gly Ala Asn Thr Gly Ile Gly Gln Ala Ile Ala Leu Ser Leu
            20                  25                  30

Ala Gln Ala Gly Ala Asp Ile Ala Ala Val Gly Arg Thr Pro Ala Gln
        35                  40                  45

Asp Thr Val Asp Gln Val Arg Ala Leu Gly Arg Arg Ala Asp Ile Ile
    50                  55                  60

Ser Ala Asp Leu Ser Thr Ile Glu Pro Val Gln Arg Val Leu Asp Glu
65                  70                  75                  80

Thr Leu Glu Lys Leu Gly Ala Leu Asp Ile Leu Val Asn Asn Ala Gly
                85                  90                  95

Ile Ile Arg Arg Ala Asp Ser Val Asp Phe Thr Glu Glu Asp Trp Asp
            100                 105                 110

Ala Val Ile Asp Thr Asn Leu Lys Thr Thr Phe Phe Leu Cys Gln Ala
        115                 120                 125

Ala Gly Arg His Met Leu Ala Gln Gly Ala Gly Lys Ile Ile Asn Ile
    130                 135                 140

Ala Ser Leu Leu Ser Phe Gln Gly Gly Ile Arg Val Pro Ser Tyr Thr
145                 150                 155                 160
```

-continued

```
Ala Ser Lys Ser Gly Val Ala Gly Leu Thr Lys Leu Leu Ala Asn Glu
                165                 170                 175

Trp Ala Ala Lys Gly Val Asn Val Asn Ala Ile Ala Pro Gly Tyr Ile
            180                 185                 190

Ala Thr Asn Asn Thr Ala Ala Leu Gln Ala Asp Glu Thr Arg Asn Arg
        195                 200                 205

Gln Ile Gln Glu Arg Ile Pro Ala Gly Arg Trp Gly Asp Pro Ala Asp
    210                 215                 220

Ile Gly Gly Ala Ala Val Phe Leu Ala Ser Ser Ala Ala Asp Tyr Ile
225                 230                 235                 240

His Gly His Thr Leu Ala Val Asp Gly Gly Trp Leu Ala Arg
                245                 250


<210> SEQ ID NO 61
<211> LENGTH: 246
<212> TYPE: PRT
<213> ORGANISM: Hoeflea phototrophica

<400> SEQUENCE: 61

Met Asn Pro Phe Ser Leu Glu Gly Lys Thr Ala Leu Val Thr Gly Ala
1               5                   10                  15

Asn Thr Gly Ile Gly Gln Ala Ile Ala Met Ala Leu Gly Arg Ala Gly
            20                  25                  30

Ala Asp Val Ile Cys Ala Gly Arg Ser Ser Cys Ala Glu Thr Val Ala
        35                  40                  45

Leu Ile Ala Gly Ser Lys Gly Lys Ala Arg Glu Leu Val Leu Asp Phe
    50                  55                  60

Ala Asp Pro Met Ala Ala Arg Asp Val Phe Ala Ala Glu Pro Val Asp
65                  70                  75                  80

Ile Leu Val Asn Asn Ala Gly Ile Ile Arg Arg Ala Asp Ala Val Asp
                85                  90                  95

Phe Thr Glu Ala Asp Trp Asp Glu Val Met Asp Val Asn Leu Lys Ala
            100                 105                 110

Val Phe Phe Thr Cys Gln Ala Phe Gly Lys Ala Val Leu Gly Arg Gly
        115                 120                 125

Gly Asn Gly Lys Ile Val Asn Ile Ala Ser Leu Leu Ser Phe Gln Gly
    130                 135                 140

Gly Ile Arg Val Pro Ser Tyr Thr Ala Ser Lys His Gly Val Ala Gly
145                 150                 155                 160

Ile Thr Lys Leu Leu Ala Asn Glu Trp Ala Ala Lys Gly Ile Asn Val
                165                 170                 175

Asn Ala Ile Ala Pro Gly Tyr Ile Glu Thr Asn Asn Thr Glu Ala Leu
            180                 185                 190

Arg Ala Asp Pro Val Arg Asn Lys Ala Ile Leu Glu Arg Ile Pro Ala
        195                 200                 205

Gly Arg Trp Gly Gln Ala Ser Asp Ile Gly Glu Ala Ala Val Phe Leu
    210                 215                 220

Ala Ser Pro Ala Ala Asn Tyr Ile His Gly Ala Val Leu Asn Val Asp
225                 230                 235                 240

Gly Gly Trp Leu Ala Arg
                245


<210> SEQ ID NO 62
<211> LENGTH: 744
<212> TYPE: DNA
<213> ORGANISM: Agrobacterium sp.
```

<400> SEQUENCE: 62
atgaagaatc ccttttcgct tcaggggcgt aaggcgctcg tcaccggcgc gaatacgggg 60
cttggccagg cgattgcggt tgggctcgcc gcggccggtg cggaggtggt ctgcgccgcc 120
cgccgcgcgc cggatgaaac gctggagatg atcgccagcg acggcggcaa ggccagcgca 180
ttgtccatcg attttgccga tccgctggcg gcgaaggaca gttttgccgg cgccggtttc 240
gatattctcg tcaacaatgc cggtatcatc cgccgtgccg attccgtcga gttctccgaa 300
ctcgactggg acgaggtgat ggacgtcaat ctcaaggcgc tgtttttcac cacccaggct 360
tttgcgaaag agctgctggc gaaaggccgg tccggcaagg tggtcaatat cgcttcgctc 420
ctttcctttc agggcggtat tcgcgtgccg tcctatacgg cggcgaaaca tggtgtcgcc 480
ggcctaacca aactcctggc gaatgaatgg gccgccaagg gcatcaatgt gaatgccatt 540
gcgcccggtt atatcgaaac caacaatacc gaggcgctac gcgccgatgc ggctcgtaac 600
aaggccattc tcgagcgcat cccggccggc cgctgggggc gctcggaaga catcgccggg 660
gcggcggttt tcctgtcatc tgcggcggcg gactatgtgc atggcgccat tctcaacgtc 720
gatggcggct ggctggcgcg ctga 744

<210> SEQ ID NO 63
<211> LENGTH: 597
<212> TYPE: DNA
<213> ORGANISM: Agrobacterium tumefaciens

<400> SEQUENCE: 63
atgatcgccg gcgtgggggg agaagcaagg gagctggcgc tcgatctgtc cgatcccatg 60
gcggcaaaag atgtttttgc tgaaggcgct tacgacctcc tcatcaacaa tgccggcatc 120
atccgccgtg ccgatgcagt cgatttctcc gaggatgact gggacgcggt gatggacgtg 180
aacctgaaag ccgtcttctt cacctcgcaa gcctttgcgc gggctctcat gtccagaaac 240
gcaagcggaa agatcgttaa cattgcatcc cttctgtcgt ttcaaggcgg cattcgcgtt 300
gcctcctaca cggccgccaa gcacggtgtg gcaggcatca ccagactgtt ggcaaacgaa 360
tgggcgtccc gcggcatcaa cgtcaatgcg atagcgcccg gttacattgc cacgaacaac 420
acggaagcgc ttcgagccga cgaggagcgc aacgcggcga tcctcgcacg cattccggct 480
ggccgctggg ggcgggcgga ggatattgcg ggtactgctg tctatctttg ttcgccggca 540
gccgattatg ttcatggcgc cattctaaac gtcgatggcg gttggctcgc gcgctga 597

<210> SEQ ID NO 64
<211> LENGTH: 762
<212> TYPE: DNA
<213> ORGANISM: Escherichia coli

<400> SEQUENCE: 64
atgattttaa gtgcattttc tctcgaaggt aaagttgcgg tcgtcactgg ttgtgatact 60
ggactgggtc aggggatggc gttggggctg gcgcaagcgg gctgtgacat tgttggcatt 120
aacatcgttg aaccgactga aaccatcgag caggtcacag cgctggggcg tcgtttttta 180
agcctgaccg ccgatctgcg aaagattgat ggtattccag cactgctgga tcgcgcggta 240
gcggagtttg gtcatattga tatcctggtg aataacgccg gattgattcg ccgcgaagat 300
gctctcgagt tcagcgaaaa ggactgggac gatgtcatga acctgaatat caagagcgta 360
ttcttcatgt ctcaggcagc ggcgaaacac tttatcgcgc aaggcaatgg cggcaagatt 420

```
atcaatatcg cgtcaatgct ctccttccag ggcgggatcc gtgtgccttc ttataccgca    480

tcaaaaagcg gcgtgatggg tgtgacgcga ttgatggcga acgaatgggc taaacacaac    540

attaatgtta atgcgatagc cccgggttac atggcgacca acaatactca acaactacgg    600

gcagatgaac aacgtagcgc ggaaattctc gaccgcattc cagctggtcg ttggggactg    660

ccgagtgacc tgatggggcc gatagtgttc cttgcctcca gcgcttcaga ttatgtgaat    720

ggttatacca ttgccgtgga tggcggttgg ctggcgcgtt aa                       762


<210> SEQ ID NO 65
<211> LENGTH: 765
<212> TYPE: DNA
<213> ORGANISM: Sphingomonas sp.

<400> SEQUENCE: 65

atgcccggca tgaccactcc tttcgatctt catggcaaga ccgcgatcgt caccggcgcc     60

aataccggca tcggccaggc cattgccctg tcgctcgcgc aggccggcgc ggatatcgcc    120

gccgtcggcc gcacgcccgc acaggacacg gtcgatcagg tccgcgcgct cggccgccgg    180

gcggacatta tctcggccga cctttcgacc atcgaaccgg tccagcgcgt cctcgacgaa    240

acgctggaaa agcttggtgc cttggacata ctggtcaaca atgccggcat catccgccgc    300

gccgacagcg tcgatttcac cgaggaggat tgggacgcgg tgatcgacac caatctcaag    360

accaccttct tcctctgtca ggccgccggt cgccacatgc ttgcccaagg cgctggcaag    420

atcatcaaca tcgcctcgct tctttccttc cagggcggca ttcgcgtgcc gagctacacc    480

gcgtccaaaa gcggcgtcgc gggcctgacc aagctgctcg ccaacgaatg ggcggccaag    540

ggcgtcaatg tgaacgccat cgcgccgggc tatatcgcca ccaacaacac cgccgcgctc    600

caggccgacg aaacccgcaa ccgccagatc caggagcgca tcccggctgg ccgctggggc    660

gaccccgccg acattggcgg cgcggccgtg ttcctggcgt ccagcgccgc cgattatatc    720

catggccaca cgctcgccgt cgacggcggc tggctcgcgc gctga                    765


<210> SEQ ID NO 66
<211> LENGTH: 741
<212> TYPE: DNA
<213> ORGANISM: Hoeflea phototrophica

<400> SEQUENCE: 66

atgaacccct tctcgcttga gggcaagacc gcccttgtga ccggtgccaa tacgggcatc     60

ggtcaggcca tcgccatggc gcttggccgc gccggggcgg acgtcatctg cgcgggacgc    120

tcgtcctgtg cggagaccgt tgccctcatc gctggcagca agggcaaggc gcgcgaactg    180

gtgctcgact tcgccgaccc gatggccgcc cgtgacgtgt tcgccgccga accggtggac    240

atcctcgtca acaacgcggg catcatccgg cgcgccgatg cagtggattt caccgaggcc    300

gactgggatg aggtgatgga cgtgaacctg aaggccgtgt tcttcacctg ccaggccttc    360

ggcaaggccg ttcttggccg tggaggaaac ggcaagatcg tcaacattgc ctcgctcctg    420

tcattccagg gtggtatccg ggtgccgtcc tacacggcct cgaagcatgg tgttgcaggc    480

atcaccaagc ttctggccaa cgaatgggcg gcgaagggca tcaatgtgaa tgccatcgcc    540

cccggttaca tcgaaacgaa caataccgaa gcactgcggg cggacccggt gcgcaacaag    600

gccatccttg agcgtatccc tgccggccgc tggggccagg cctcggacat cggcgaagcc    660

gccgtgttcc ttgcctctcc ggctgccaat tacatccatg gtgcagtgct gaatgttgac    720

ggaggctggc ttgcccgctg a                                              741
```

<210> SEQ ID NO 67
<211> LENGTH: 446
<212> TYPE: PRT
<213> ORGANISM: Escherichia coli

<400> SEQUENCE: 67

```
Met Ser Ser Gln Phe Thr Thr Pro Val Val Thr Glu Met Gln Val Ile
1               5                   10                  15

Pro Val Ala Gly His Asp Ser Met Leu Met Asn Leu Ser Gly Ala His
            20                  25                  30

Ala Pro Phe Phe Thr Arg Asn Ile Val Ile Ile Lys Asp Asn Ser Gly
        35                  40                  45

His Thr Gly Val Gly Glu Ile Pro Gly Gly Glu Lys Ile Arg Lys Thr
    50                  55                  60

Leu Glu Asp Ala Ile Pro Leu Val Val Gly Lys Thr Leu Gly Glu Tyr
65                  70                  75                  80

Lys Asn Val Leu Thr Leu Val Arg Asn Thr Phe Ala Asp Arg Asp Ala
                85                  90                  95

Gly Gly Arg Gly Leu Gln Thr Phe Asp Leu Arg Thr Thr Ile His Val
            100                 105                 110

Val Thr Gly Ile Glu Ala Ala Met Leu Asp Leu Leu Gly Gln His Leu
        115                 120                 125

Gly Val Asn Val Ala Ser Leu Leu Gly Asp Gly Gln Gln Arg Ser Glu
    130                 135                 140

Val Glu Met Leu Gly Tyr Leu Phe Phe Val Gly Asn Arg Lys Ala Thr
145                 150                 155                 160

Pro Leu Pro Tyr Gln Ser Gln Pro Asp Asp Ser Cys Asp Trp Tyr Arg
                165                 170                 175

Leu Arg His Glu Glu Ala Met Thr Pro Asp Ala Val Val Arg Leu Ala
            180                 185                 190

Glu Ala Ala Tyr Glu Lys Tyr Gly Phe Asn Asp Phe Lys Leu Lys Gly
        195                 200                 205

Gly Val Leu Ala Gly Glu Glu Glu Ala Glu Ser Ile Val Ala Leu Ala
    210                 215                 220

Gln Arg Phe Pro Gln Ala Arg Ile Thr Leu Asp Pro Asn Gly Ala Trp
225                 230                 235                 240

Ser Leu Asn Glu Ala Ile Lys Ile Gly Lys Tyr Leu Lys Gly Ser Leu
                245                 250                 255

Ala Tyr Ala Glu Asp Pro Cys Gly Ala Glu Gln Gly Phe Ser Gly Arg
            260                 265                 270

Glu Val Met Ala Glu Phe Arg Arg Ala Thr Gly Leu Pro Thr Ala Thr
        275                 280                 285

Asn Met Ile Ala Thr Asp Trp Arg Gln Met Gly His Thr Leu Ser Leu
    290                 295                 300

Gln Ser Val Asp Ile Pro Leu Ala Asp Pro His Phe Trp Thr Met Gln
305                 310                 315                 320

Gly Ser Val Arg Val Ala Gln Met Cys His Glu Phe Gly Leu Thr Trp
                325                 330                 335

Gly Ser His Ser Asn Asn His Phe Asp Ile Ser Leu Ala Met Phe Thr
            340                 345                 350

His Val Ala Ala Ala Ala Pro Gly Lys Ile Thr Ala Ile Asp Thr His
        355                 360                 365

Trp Ile Trp Gln Glu Gly Asn Gln Arg Leu Thr Lys Glu Pro Phe Glu
```

```
    370                 375                 380

Ile Lys Gly Gly Leu Val Gln Val Pro Glu Lys Pro Gly Leu Gly Val
385                 390                 395                 400

Glu Ile Asp Met Asp Gln Val Met Lys Ala His Glu Leu Tyr Gln Lys
                405                 410                 415

His Gly Leu Gly Ala Arg Asp Asp Ala Met Gly Met Gln Tyr Leu Ile
            420                 425                 430

Pro Gly Trp Thr Phe Asp Asn Lys Arg Pro Cys Met Val Arg
        435                 440                 445


<210> SEQ ID NO 68
<211> LENGTH: 446
<212> TYPE: PRT
<213> ORGANISM: Pseudomonas stutzeri

<400> SEQUENCE: 68

Met Thr Thr Ala Met Ser Gly Thr Pro Arg Ile Thr Glu Leu Thr Val
1               5                   10                  15

Val Pro Val Ala Gly Gln Asp Ser Met Leu Met Asn Leu Ser Gly Ala
            20                  25                  30

His Gly Pro Trp Phe Thr Arg Asn Ile Leu Ile Leu Lys Asp Ser Ala
        35                  40                  45

Gly His Val Gly Val Gly Glu Val Pro Gly Gly Glu Ala Ile Arg Gln
    50                  55                  60

Thr Leu Asp Asp Ala Arg Ala Leu Leu Val Gly Glu Pro Ile Gly Gln
65                  70                  75                  80

Tyr Asn Ala Leu Leu Gly Lys Val Arg Arg Ala Phe Ala Asp Arg Asp
                85                  90                  95

Ala Gly Gly Arg Gly Leu Gln Thr Phe Asp Leu Arg Ile Ala Ile His
            100                 105                 110

Ala Val Thr Ala Leu Glu Ser Ala Leu Leu Asp Leu Leu Gly Gln His
        115                 120                 125

Leu Glu Val Pro Val Ala Ala Leu Leu Gly Glu Gly Gln Gln Arg Asp
    130                 135                 140

Glu Val Glu Met Leu Gly Tyr Leu Phe Phe Ile Gly Asp Arg Asn Arg
145                 150                 155                 160

Thr Asp Leu Gly Tyr Arg Asp Glu Ser Asn Ser Asp Asp Ala Trp Phe
                165                 170                 175

Arg Val Arg Asn Glu Glu Ala Met Thr Pro Glu Arg Ile Val Arg Gln
            180                 185                 190

Ala Glu Ala Ala Tyr Glu Arg Tyr Gly Phe Lys Asp Phe Lys Leu Lys
        195                 200                 205

Gly Gly Val Leu Arg Gly Glu Glu Glu Val Glu Ala Ile Arg Ala Leu
    210                 215                 220

Ala Gln Arg Phe Pro Asp Ala Arg Val Thr Leu Asp Pro Asn Gly Ala
225                 230                 235                 240

Trp Ser Leu Asp Glu Ala Ser Gly Leu Cys Arg Asp Leu His Gly Val
                245                 250                 255

Leu Ala Tyr Ala Glu Asp Pro Cys Gly Ala Glu Asn Gly Tyr Ser Gly
            260                 265                 270

Arg Glu Val Met Ala Glu Phe Arg Arg Ala Thr Gly Leu Pro Thr Ala
        275                 280                 285

Thr Asn Met Ile Ala Thr Asp Trp Arg Gln Met Ser His Ala Val Cys
    290                 295                 300
```

-continued

```
Leu His Ser Val Asp Ile Pro Leu Ala Asp Pro His Phe Trp Thr Met
305                 310                 315                 320

Ala Gly Ser Val Arg Val Ala Gln Met Cys Ala Asp Phe Gly Leu Thr
                325                 330                 335

Trp Gly Ser His Ser Asn Asn His Phe Asp Ile Ser Leu Ala Met Phe
            340                 345                 350

Thr His Val Ala Ala Ala Ala Pro Gly Arg Val Thr Ala Ile Asp Thr
        355                 360                 365

His Trp Ile Trp Gln Asp Gly Gln His Leu Thr Arg Glu Pro Leu Lys
    370                 375                 380

Ile Val Ser Gly Lys Val Ala Val Pro Gln Lys Pro Gly Leu Gly Val
385                 390                 395                 400

Glu Leu Asp Trp Asp Ala Leu Glu Gln Ala His Ala His Tyr Gln Glu
                405                 410                 415

Lys Gly Leu Gly Ala Arg Asp Asp Ala Ile Ala Met Gln Tyr Leu Ile
            420                 425                 430

Pro Asn Trp Thr Phe Asn Asn Lys Lys Pro Cys Met Val Arg
        435                 440                 445


<210> SEQ ID NO 69
<211> LENGTH: 1341
<212> TYPE: DNA
<213> ORGANISM: Escherichia coli

<400> SEQUENCE: 69

atgagttctc aatttacgac gcctgttgtt actgaaatgc aggttatccc ggtggcgggt     60

catgacagta tgctgatgaa tctgagtggt gcacacgcac cgttctttac gcgtaatatt    120

gtgattatca aagataattc tggtcacact ggcgtagggg aaattcccgg cggcgagaaa    180

atccgtaaaa cgctggaaga tgcgattccg ctggtggtag gtaaaacgct gggtgaatac    240

aaaaacgttc tgacgctggt gcgtaatact tttgccgatc gtgatgctgg tgggcgcggt    300

ttgcagacat ttgacctacg taccactatt catgtagtta ccgggataga agcggcaatg    360

ctggatctgc tggggcagca tctgggggta aacgtggcat cgctgctggg cgatggtcaa    420

cagcgtagcg aagtcgaaat gctcggttat ctgttcttcg tcggtaatcg caaagccacg    480

ccgctgccgt atcaaagcca gccggatgac tcatgcgact ggtatcgcct gcgtcatgaa    540

gaagcgatga cgccggatgc ggtggtgcgc ctggcggaag cggcatatga aaaatatggc    600

ttcaacgatt tcaaactgaa gggcggtgta ctggccgggg aagaagaggc cgagtctatt    660

gtggcactgg cgcaacgctt cccgcaggcg cgtattacgc tcgatcctaa cggtgcctgg    720

tcgctgaacg aagcgattaa aatcggtaaa tacctgaaag gttcgctggc ttatgcagaa    780

gatccgtgtg gtgcggagca aggtttctcc gggcgtgaag tgatggcaga gttccgtcgc    840

gcgacaggtc taccgactgc aaccaatatg atcgccaccg actggcggca aatgggccat    900

acgctctccc tgcaatccgt tgatatcccg ctggcggatc cgcatttctg gacaatgcaa    960

ggttcggtac gtgtggcgca aatgtgccat gaatttggcc tgacctgggg ttcacactct   1020

aacaaccact tcgatatttc cctggcgatg tttacccatg ttgccgccgc tgcaccgggt   1080

aaaattactg ctattgatac gcactggatt tggcaggaag gcaatcagcg cctgaccaaa   1140

gaaccgtttg agatcaaagg cgggctggta caggtgccag aaaaaccggg gctgggtgta   1200

gaaatcgata tggatcaagt gatgaaagcc catgagctgt atcagaaaca cgggcttggc   1260

gcgcgtgacg atgcgatggg aatgcagtat ctgattcctg gctggacgtt cgataacaag   1320
```

-continued

```
cgcccgtgca tggtgcgtta a                                              1341


<210> SEQ ID NO 70
<211> LENGTH: 1341
<212> TYPE: DNA
<213> ORGANISM: Pseudomonas stutzeri

<400> SEQUENCE: 70

atgaccaccg ccatgtcggg cacgccccgc atcaccgaac tcaccgtcgt gcccgtcgcc      60

gggcaggaca gcatgctgat gaacctcagc ggcgcccatg ggccctggtt cacccgcaac     120

atcctcatcc tcaaggacag cgccggccac gtcggcgtcg gcgaagtgcc gggcggcgaa     180

gccatccgcc agaccctcga cgatgcccgt gccctgctgg tcggcgaacc gatcggccag     240

tacaacgcgc tgctcggcaa ggtgcgccgc gccttcgccg accgtgacgc cggcggccgc     300

ggcctgcaga ccttcgacct gcgcatcgcc attcacgccg tcaccgcgct ggagtcggcg     360

ctgctcgacc tgctcggcca gcacctcgag gtgccggtcg ccgccttgct cggcgaaggc     420

cagcagcgtg acgaagtgga aatgctcggc tacctgttct tcatcggcga tcgcaacagg     480

accgacctcg gctaccgcga cgaatccaac tccgacgacg cctggtttcg cgtgcgcaac     540

gaggaggcca tgacgccgga gcgcatcgtc cgccaggccg aggcggccta cgagcgctac     600

ggcttcaagg acttcaagct caagggcggc gtactgcgcg gcgaagagga agtcgaggcg     660

atccgcgccc tggcccagcg cttccccgac gcccgcgtga ctctggaccc caacggcgcc     720

tggtcgctgg acgaagccag cggcctgtgt cgcgacctgc acggcgtgct ggcctatgcc     780

gaagacccct gcggtgccga gaacggctat tccggccgcg aggtgatggc cgagttccgc     840

cgcgccaccg gtctgcccac cgcgaccaac atgatcgcca ccgactggcg acagatgagt     900

cacgcggtgt gcctgcactc ggtggacatc ccgctggccg acccgcactt ctggaccatg     960

gccggctctg tgcgcgtggc gcagatgtgc gccgacttcg gcctgacctg ggggttcgcac    1020

tcgaacaacc acttcgacat ctccctggcg atgttcaccc acgtggcggc cgccgcgccg    1080

ggtcgcgtca ccgccatcga cacccactgg atctggcagg acggccagca cctgacccgc    1140

gagccgctga agatcgtcag cggcaaggtt gcggtgccgc agaagccggg gctgggcgtc    1200

gagctggact gggatgccct ggagcaggcg catgcccact accaagagaa aggcctgggt    1260

gcccgcgatg acgccatcgc catgcagtac ctgatcccca actggacctt caacaacaag    1320

aagccgtgca tggtgcgctg a                                              1341


<210> SEQ ID NO 71
<211> LENGTH: 256
<212> TYPE: PRT
<213> ORGANISM: Gluconobacter oxydans

<400> SEQUENCE: 71

Met Ser His Pro Asp Leu Phe Ser Leu Ser Gly Ala Arg Ala Leu Val
1               5                   10                  15

Thr Gly Ala Ser Arg Gly Ile Gly Leu Thr Leu Ala Lys Gly Leu Ala
            20                  25                  30

Arg Tyr Gly Ala Glu Val Val Leu Asn Gly Arg Asn Ala Glu Ser Leu
        35                  40                  45

Asp Ser Ala Gln Ser Gly Phe Glu Ala Glu Gly Leu Lys Ala Ser Thr
    50                  55                  60

Ala Val Phe Asp Val Thr Asp Gln Asp Ala Val Ile Asp Gly Val Ala
65                  70                  75                  80
```

-continued

```
Ala Ile Glu Arg Asp Met Gly Pro Ile Asp Ile Leu Ile Asn Asn Ala
                85                  90                  95

Gly Ile Gln Arg Arg Ala Pro Leu Glu Glu Phe Ser Arg Lys Asp Trp
            100                 105                 110

Asp Asp Leu Met Ser Thr Asn Val Asn Ala Val Phe Phe Val Gly Gln
        115                 120                 125

Ala Val Ala Arg His Met Ile Pro Arg Gly Arg Gly Lys Ile Val Asn
    130                 135                 140

Ile Cys Ser Val Gln Ser Glu Leu Ala Arg Pro Gly Ile Ala Pro Tyr
145                 150                 155                 160

Thr Ala Thr Lys Gly Ala Val Lys Asn Leu Thr Lys Gly Met Ala Thr
                165                 170                 175

Asp Trp Gly Arg His Gly Leu Gln Ile Asn Gly Leu Ala Pro Gly Tyr
            180                 185                 190

Phe Ala Thr Glu Met Thr Glu Arg Leu Val Ala Asp Glu Glu Phe Thr
        195                 200                 205

Asp Trp Leu Cys Lys Arg Thr Pro Ala Gly Arg Trp Gly Gln Val Glu
    210                 215                 220

Glu Leu Val Gly Ala Ala Val Phe Leu Ser Ser Arg Ala Ser Ser Phe
225                 230                 235                 240

Val Asn Gly Gln Val Leu Met Val Asp Gly Gly Ile Thr Val Ser Leu
                245                 250                 255
```

<210> SEQ ID NO 72
<211> LENGTH: 771
<212> TYPE: DNA
<213> ORGANISM: Gluconobacter oxydans

<400> SEQUENCE: 72

```
atgtctcacc cggatctgtt tagcttaagt ggcgcacgcg cattagttac tggtgcctct      60

cgtggtattg gtttaaccct ggccaaaggt ttagcccgtt atggtgccga agtggtttta     120

aatggccgta atgccgaaag cctggattct gcccaaagtg gctttgaagc cgaaggctta     180

aaagcatcta ccgctgtgtt tgacgtgacc gatcaagatg cagtcattga cggcgtggca     240

gcaattgaac gcgatatggg tccgattgat atcctgatca acaatgcggg cattcaacgc     300

agagccccgt tagaagaatt ttctcgcaaa gactgggacg atctgatgag caccaacgtt     360

aacgccgtgt tctttgtggg acaagccgtt gccagacaca tgattcctag aggtcgcggt     420

aaaatcgtca acatctgttc agtgcagagc gaactggcaa gaccgggtat tgcaccttat     480

accgccacaa aaggagccgt caaaaatctg accaaaggta tggccaccga ttggggtcgt     540

catggtttac agattaatgg cttagcaccg ggctattttg ccaccgagat gaccgaacgc     600

ttagttgccg acgaagaatt taccgactgg ttatgcaaac gcacccctgc aggcagatgg     660

ggccaagttg aagaattagt aggcgcagcc gtgtttttaa gtagtagagc ctcaagcttc     720

gtgaatggcc aagtcctgat ggttgatggt ggaattactg tgagcctgta a              771
```

<210> SEQ ID NO 73
<211> LENGTH: 371
<212> TYPE: PRT
<213> ORGANISM: Escherichia coli K-12

<400> SEQUENCE: 73

```
Met His Arg Gln Ser Phe Phe Leu Val Pro Leu Ile Cys Leu Ser Ser
1               5                   10                  15

Ala Leu Trp Ala Ala Pro Ala Thr Val Asn Val Glu Val Leu Gln Asp
```

```
            20                  25                  30

Lys Leu Asp His Pro Trp Ala Leu Ala Phe Leu Pro Asp Asn His Gly
        35                  40                  45

Met Leu Ile Thr Leu Arg Gly Gly Glu Leu Arg His Trp Gln Ala Gly
    50                  55                  60

Lys Gly Leu Ser Ala Pro Leu Ser Gly Val Pro Asp Val Trp Ala His
65                  70                  75                  80

Gly Gln Gly Gly Leu Leu Asp Val Val Leu Ala Pro Asp Phe Ala Gln
                85                  90                  95

Ser Arg Arg Ile Trp Leu Ser Tyr Ser Glu Val Gly Asp Asp Gly Lys
            100                 105                 110

Ala Gly Thr Ala Val Gly Tyr Gly Arg Leu Ser Asp Asp Leu Ser Lys
        115                 120                 125

Val Thr Asp Phe Arg Thr Val Phe Arg Gln Met Pro Lys Leu Ser Thr
    130                 135                 140

Gly Asn His Phe Gly Gly Arg Leu Val Phe Asp Gly Lys Gly Tyr Leu
145                 150                 155                 160

Phe Ile Ala Leu Gly Glu Asn Asn Gln Arg Pro Thr Ala Gln Asp Leu
                165                 170                 175

Asp Lys Leu Gln Gly Lys Leu Val Arg Leu Thr Asp Gln Gly Glu Ile
            180                 185                 190

Pro Asp Asp Asn Pro Phe Ile Lys Glu Ser Gly Ala Arg Ala Glu Ile
        195                 200                 205

Trp Ser Tyr Gly Ile Arg Asn Pro Gln Gly Met Ala Met Asn Pro Trp
    210                 215                 220

Ser Asn Ala Leu Trp Leu Asn Glu His Gly Pro Arg Gly Gly Asp Glu
225                 230                 235                 240

Ile Asn Ile Pro Gln Lys Gly Lys Asn Tyr Gly Trp Pro Leu Ala Thr
                245                 250                 255

Trp Gly Ile Asn Tyr Ser Gly Phe Lys Ile Pro Glu Ala Lys Gly Glu
            260                 265                 270

Ile Val Ala Gly Thr Glu Gln Pro Val Phe Tyr Trp Lys Asp Ser Pro
        275                 280                 285

Ala Val Ser Gly Met Ala Phe Tyr Asn Ser Asp Lys Phe Pro Gln Trp
    290                 295                 300

Gln Gln Lys Leu Phe Ile Gly Ala Leu Lys Asp Lys Asp Val Ile Val
305                 310                 315                 320

Met Ser Val Asn Gly Asp Lys Val Thr Glu Asp Gly Arg Ile Leu Thr
                325                 330                 335

Asp Arg Gly Gln Arg Ile Arg Asp Val Arg Thr Gly Pro Asp Gly Tyr
            340                 345                 350

Leu Tyr Val Leu Thr Asp Glu Ser Ser Gly Glu Leu Leu Lys Val Ser
        355                 360                 365

Pro Arg Asn
    370
```

<210> SEQ ID NO 74
<211> LENGTH: 382
<212> TYPE: PRT
<213> ORGANISM: Pseudomonas

<400> SEQUENCE: 74

```
Met Leu Arg Gln Ala Ile Arg Thr Thr Leu Cys Gly Phe Val Ile Ala
1               5                   10                  15
```

-continued

```
Ala Ser Phe Gln Val Ala Ala Glu Thr Gln Arg Phe Pro Ser Glu Ala
            20                  25                  30

Gly Gln Val Thr Val Lys Glu Ile Ala Ala Gly Leu Glu Asn Pro Trp
        35                  40                  45

Gly Leu Ala Phe Leu Pro Asp Gly Glu His Met Leu Val Thr Glu Arg
    50                  55                  60

Pro Gly Arg Leu Arg Leu Val Gly Leu Asp Gly Ser Arg Ser Glu Pro
65                  70                  75                  80

Leu Ala Gly Val Pro Asp Val Phe Ala Arg Ala Gln Gly Gly Leu Leu
                85                  90                  95

Asp Val Arg Leu Ser Pro Ala Phe Glu Gln Asp Arg Leu Val Tyr Leu
            100                 105                 110

Ser Tyr Ala Glu Val Gly Glu Asp Gly Lys Ala Gly Thr Ala Val Gly
        115                 120                 125

Arg Gly Arg Leu Asn Asp Asp Arg Ser Arg Leu Glu Asn Phe Glu Val
    130                 135                 140

Ile Phe Arg Gln Leu Pro Lys Leu Ser Ser Gly Ile His Phe Gly Ser
145                 150                 155                 160

Arg Leu Val Phe Ala Gly Asn Gly His Leu Phe Val Ala Leu Gly Glu
                165                 170                 175

Asn Asn Gln Arg Ser Thr Ser Gln Asp Leu Asp Lys His Gln Gly Lys
            180                 185                 190

Val Val Arg Ile Gly Leu Asp Gly Ser Val Pro Asp Asp Asn Pro Phe
        195                 200                 205

Val Gly Arg Asp Gly Val Arg Pro Glu Ile Trp Ser Tyr Gly His Arg
    210                 215                 220

Asn Gln Gln Gly Ala Ala Leu Asn Pro Trp Ser Gly Val Leu Trp Thr
225                 230                 235                 240

His Glu His Gly Pro Arg Gly Gly Asp Glu Ile Asn Ile Pro Gln Ala
                245                 250                 255

Gly Lys Asn Tyr Gly Trp Pro Leu Ala Thr His Gly Ile Asn Tyr Ser
            260                 265                 270

Met Leu Pro Ile Pro Glu Ala Lys Gly Lys Thr Val Lys Gly Thr Glu
        275                 280                 285

Pro Pro His His Val Trp Asp Lys Ser Pro Gly Ile Ser Gly Met Ala
    290                 295                 300

Phe Tyr Asp Ala Glu Arg Phe Pro Ala Trp Gln His Ser Leu Phe Ile
305                 310                 315                 320

Gly Ala Leu Val Asp Leu Ser Leu Ile Arg Leu Gln Leu Asp Gly Asp
                325                 330                 335

Arg Ile Val Gly Glu Glu Arg Leu Leu Lys Asp Leu Asn Ala Arg Ile
            340                 345                 350

Arg Asp Val Arg Val Gly Pro Asp Gly Phe Leu Tyr Leu Leu Thr Asp
        355                 360                 365

Ala Ala Asp Gly Lys Leu Leu Gln Val Gly Leu Asp Ser Asn
    370                 375                 380


<210> SEQ ID NO 75
<211> LENGTH: 387
<212> TYPE: PRT
<213> ORGANISM: Achromobacter

<400> SEQUENCE: 75

Met Gln Ser Arg Thr Ala Ala Ser Thr Arg Ala Ile Pro Leu Ile Leu
1               5                   10                  15
```

-continued

Ser Leu Ala Met Ala Phe Ala Ala Ala Pro Ala Val Ala Gln Ala Ala
20 25 30

Gln Glu Pro Pro Ser Ala Pro Ala Arg Val Thr Pro Val Val Gly Gly
35 40 45

Leu Asp His Pro Trp Ser Met Ala Phe Leu Pro Asp Gly Gly Ile Leu
50 55 60

Ile Thr Glu Arg Pro Gly Asn Leu Arg Leu Leu Arg Thr Pro Gly Gly
65 70 75 80

Leu Ser Lys Pro Leu Ser Gly Val Pro Gln Val Ala Ala Arg Gly Gln
85 90 95

Gly Gly Leu Leu Asp Val Ala Leu Ser Pro Asp Phe Ala Thr Asp Arg
100 105 110

Tyr Val Tyr Leu Ala Tyr Ala Glu Ser Asp Gly Asp Lys Ser Gly Thr
115 120 125

Ala Val Gly Arg Gly Arg Leu Ala Asp Asp Ala Ser Gly Leu Glu Gly
130 135 140

Phe Lys Val Leu Phe Arg Gln Glu Pro Lys Leu Ser Ser Gly Gln His
145 150 155 160

Phe Gly Ser Arg Leu Val Phe Asp Gly Lys Gly Tyr Leu Tyr Ile Ala
165 170 175

Leu Gly Glu Asn Asn Gln Arg Pro Thr Ala Gln Asp Leu Asp Lys Leu
180 185 190

Gln Gly Lys Val Val Arg Leu Lys Thr Asp Gly Ser Val Pro Ala Asp
195 200 205

Asn Pro Phe Val Gly Lys Pro Gly Ala Arg Pro Glu Ile Trp Ser Tyr
210 215 220

Gly His Arg Asn Pro Gln Gly Met Ala Leu Asn Pro Trp Thr Gly Glu
225 230 235 240

Leu Trp Glu Asn Glu His Gly Pro Arg Gly Gly Asp Glu Ile Asn Val
245 250 255

Val Lys Pro Gly Lys Asn Tyr Gly Trp Pro Leu Ala Thr Tyr Gly Ile
260 265 270

Asn Tyr Ser Gly Phe Ala Ile Pro Glu Ala Lys Gly Glu Thr Leu Pro
275 280 285

Gly Met Glu Pro Pro Ile His Trp Trp Pro Lys Ser Pro Ala Ile Ser
290 295 300

Gly Met Ala Phe Tyr Asp Ala Asp Arg Phe Pro Ala Trp Arg Asn Ser
305 310 315 320

Leu Phe Ile Gly Ala Leu Gly Asn Gln Asn Leu Ile Arg Leu Thr Val
325 330 335

Asp Gly Asn Arg Val Val Glu Lys Glu Arg Leu Leu Val Asp Arg Lys
340 345 350

Arg Arg Ile Arg Asp Val Arg Gln Gly Pro Asp Gly Tyr Val Tyr Val
355 360 365

Leu Thr Asp Ala Ser Pro Gly Glu Leu Leu Arg Val Ala Pro Ala Glu
370 375 380

Thr Gly Gly
385

<210> SEQ ID NO 76
<211> LENGTH: 372
<212> TYPE: PRT
<213> ORGANISM: Pseudomonas

<400> SEQUENCE: 76

Met Asn Asn Pro Ile Arg Gly Leu Phe Cys Ala Leu Ala Leu Leu Ser
1 5 10 15

Ala Pro Met Leu Ala Pro Ser Ala Trp Ala Ser Ala Lys Val Glu Val
20 25 30

Leu Tyr Glu Gly Leu Glu His Pro Trp Ala Leu Ala Phe Leu Pro Asp
35 40 45

Ala Gln Gly Met Leu Ile Thr Glu Arg Arg Gly Ser Leu Arg Leu Leu
50 55 60

Asp Ala Gln Gly Lys Leu Ser Glu Pro Leu Ala Gly Val Pro Glu Val
65 70 75 80

Phe Ala Val Gly Gln Gly Gly Leu Leu Asp Val Val Leu Ser Pro Ser
85 90 95

Phe Ala Glu Asp Arg Leu Val Tyr Leu Ser Phe Ala Gln Ala Glu Gly
100 105 110

Asp Lys Ala Ala Thr Ser Val Gly Arg Gly Arg Leu Ser Glu Asp Leu
115 120 125

Arg Ser Leu Glu Asp Phe Lys Val Ile Phe Arg Gln Met Pro Ala Leu
130 135 140

Ser Ser Gly His His Phe Gly Ser Arg Leu Val Phe Asp Arg Asp Gly
145 150 155 160

Tyr Leu Phe Ile Ala Leu Gly Glu His Asn Gln Arg Pro Thr Ser Gln
165 170 175

Asp Leu Asp Lys Leu Gln Gly Lys Val Val Arg Leu Tyr Pro Asp Gly
180 185 190

Arg Ile Pro Asp Asp Asn Pro Phe Val Gly Arg Glu Gly Ala Arg Ala
195 200 205

Glu Ile Trp Ser Tyr Gly His Arg Asn Gln Gln Gly Ala Ala Leu Asn
210 215 220

Pro Trp Thr Gly Lys Leu Trp Thr His Glu His Gly Pro Arg Gly Gly
225 230 235 240

Asp Glu Val Asn Ile Pro Glu Ala Gly Lys Asn Tyr Gly Trp Pro Ile
245 250 255

Ala Thr His Gly Val Asn Tyr Ser Phe Leu Ala Ile Pro Glu Ala Glu
260 265 270

Gly Lys Glu Val Ala Gly Thr Glu Pro Pro His His Val Trp Lys Lys
275 280 285

Ser Pro Ala Ile Ser Gly Met Ala Phe Tyr Asp His Ala Arg Phe Pro
290 295 300

Ala Trp Gln His Ser Leu Phe Val Gly Ala Leu Ala Gly Ala Glu Leu
305 310 315 320

Ile Arg Leu Gln Leu Asn Gly Asp Lys Val Val Gly Glu Glu Arg Leu
325 330 335

Leu Gly Glu Arg Lys Ala Arg Ile Arg Asp Val Arg Val Gly Pro Asp
340 345 350

Gly Tyr Leu Tyr Leu Leu Thr Asp Ser Gly Lys Gly Gln Leu Leu Lys
355 360 365

Val Gly Leu Glu
370

<210> SEQ ID NO 77
<211> LENGTH: 381
<212> TYPE: PRT
<213> ORGANISM: Pseudomonas

<400> SEQUENCE: 77

```
Met Leu Arg Ala Pro Trp Leu Val Thr Leu Thr Ala Ala Ala Leu Leu
1               5                   10                  15

Pro Leu Trp Ala His Ala Ala Ala Glu Gln Arg Phe Pro Ser Glu Glu
            20                  25                  30

Gly Thr Leu Ile Val Asp Thr Leu Ala Asn Gly Leu Arg Asn Pro Trp
        35                  40                  45

Ala Leu Ala Phe Leu Pro Gly Gly Lys Asp Met Leu Val Thr Glu Arg
    50                  55                  60

Ala Gly Asn Leu Arg Leu Val Asn Ala Glu Gly Lys Val Gly Pro Ser
65                  70                  75                  80

Ile Ser Gly Val Pro Lys Val Trp Ala Glu Gly Gln Gly Gly Leu Leu
                85                  90                  95

Asp Val Ala Leu Ser Pro Glu Phe Gly Lys Asp Arg Thr Val Tyr Leu
            100                 105                 110

Ser Tyr Ala Glu Glu Gly Ser Asp Gly Lys Ala Gly Thr Ala Val Gly
        115                 120                 125

Arg Gly Gln Leu Ser Glu Asp Arg Ala Arg Leu Glu His Phe Thr Val
    130                 135                 140

Ile Phe Arg Gln Leu Pro Lys Leu Ser Val Gly Asn His Phe Gly Ser
145                 150                 155                 160

Arg Leu Val Phe Asp Arg Asn Gly Tyr Leu Phe Ile Ala Leu Gly Glu
                165                 170                 175

Asn Asn Gln Arg Pro Thr Ala Gln Asp Leu Asp Lys Leu Gln Gly Lys
            180                 185                 190

Val Val Arg Ile Leu Pro Asp Gly Glu Val Pro Lys Asp Asn Pro Phe
        195                 200                 205

Val Gly Lys Asp Asn Val Arg Pro Glu Ile Trp Ser Tyr Gly His Arg
    210                 215                 220

Asn Gln Gln Gly Ala Ala Leu Asn Pro Trp Thr Gly Gln Leu Trp Thr
225                 230                 235                 240

His Glu His Gly Pro Arg Gly Gly Asp Glu Ile Asn Ile Pro Lys Pro
                245                 250                 255

Gly Lys Asn Tyr Gly Trp Pro Ile Ala Thr His Gly Ile Asn Tyr Ser
            260                 265                 270

Leu Leu Pro Ile Pro Glu Ala Lys Gly Glu His Val Asp Gly Met Val
        275                 280                 285

Asp Pro His His Val Trp Glu Lys Ser Pro Gly Ile Ser Gly Met Ala
    290                 295                 300

Phe Tyr Asp Ser Pro Thr Phe Lys Ala Trp Asp His Asn Leu Phe Ile
305                 310                 315                 320

Gly Ala Leu Ala Thr Gln Glu Leu Ile Arg Leu Gln Leu Glu Gly Asp
                325                 330                 335

Lys Val Val His Glu Glu Arg Leu Leu Gly Asp Leu Lys Ala Arg Ile
            340                 345                 350

Arg Asp Val Arg Met Gly Pro Asp Gly Tyr Leu Tyr Val Leu Thr Asp
        355                 360                 365

Asp Lys Asp Gly Ala Leu Leu Lys Val Gly Leu Ala Asp
    370                 375                 380
```

<210> SEQ ID NO 78
<211> LENGTH: 375
<212> TYPE: PRT

<213> ORGANISM: Citrobacter

<400> SEQUENCE: 78

Met Arg Arg Ser Leu Ile Pro Leu Met Thr Leu Leu Ile Phe Pro Trp
1 5 10 15

Phe Ser Gln Ala Glu Thr Pro Ala Val Asn Val Glu Val Leu Gln Thr
20 25 30

Lys Leu Asp His Pro Trp Ala Leu Ala Phe Leu Pro Gly Asp Asn Gly
35 40 45

Met Leu Ile Thr Leu Arg Gly Gly Gln Leu Arg His Trp Gln Ala Asp
50 55 60

Lys Gly Leu Ser Asp Pro Ile Pro Gly Val Pro Thr Val Trp Ala Ser
65 70 75 80

Gly Gln Gly Gly Leu Leu Asp Val Ala Leu Ala Pro Asp Phe Ser Gln
85 90 95

Ser Arg Arg Val Trp Leu Ser Phe Ala Gln Ala Asp Ala Gln Gly Asn
100 105 110

Ala Gly Thr Val Val Gly Tyr Gly Arg Leu Ser Asp Asp Leu Ser Arg
115 120 125

Leu Glu Asn Phe Gln Thr Val Phe Arg Gln Met Pro Lys Leu Ser Thr
130 135 140

Gly Asn His Phe Gly Gly Arg Leu Val Phe Asp Gly Asn Gly Tyr Leu
145 150 155 160

Phe Ile Gly Leu Gly Glu Asn Asn Gln Arg Pro Thr Ala Gln Asp Leu
165 170 175

Asp Lys Leu Gln Gly Lys Val Val Arg Leu Thr Asp Gln Gly Lys Ile
180 185 190

Pro Pro Asp Asn Pro Phe Val Asn Gln Pro Gly Ala Arg Pro Glu Ile
195 200 205

Trp Ser Tyr Gly Ile Arg Asn Pro Gln Gly Met Ala Met Asn Pro Trp
210 215 220

Ser Asp Thr Leu Trp Leu Asn Glu His Gly Pro Arg Gly Gly Asp Glu
225 230 235 240

Ile Asn Ile Pro Glu Lys Gly Lys Asn Tyr Gly Trp Pro Leu Ala Thr
245 250 255

Trp Gly Ile Asn Tyr Ser Gly Phe Lys Ile Pro Glu Ala Gln Gly Glu
260 265 270

Lys Val Ala Gly Thr Glu Gln Pro Ile Phe Tyr Trp Gln Lys Ser Pro
275 280 285

Ala Val Ser Gly Met Ala Phe Tyr Asp His Asp Thr Phe Pro Gln Trp
290 295 300

Arg Gln Lys Leu Phe Leu Gly Ala Leu Lys Asp Gln Asn Val Ile Val
305 310 315 320

Met Asn Val Asn Gly Asn Thr Val Thr Glu Glu Gly Arg Ile Leu Gly
325 330 335

Glu Arg Lys Gln Arg Ile Arg Asp Val Arg Val Gly Pro Asp Gly Tyr
340 345 350

Leu Tyr Val Leu Thr Asp Glu Ser Asp Gly Glu Leu Leu Lys Val Ser
355 360 365

Pro Arg Ser Ala Gly Asn Pro
370 375

<210> SEQ ID NO 79
<211> LENGTH: 1059

<212> TYPE: DNA
<213> ORGANISM: Escherichia coli K-12

<400> SEQUENCE: 79
atggcaccag caaccgtgaa tgtggaagtt ctgcaggata aactggatca tccgtgggca 60
ctggcatttt taccggataa ccatggcatg ctgattaccc tgcgtggtgg tgaactgcgt 120
cattggcaag caggtaaagg tttaagcgca ccgttaagtg gtgttccgga tgtttgggca 180
catggtcaag gtggtctgtt agatgtggtt ttagcaccgg attttgcaca gtctcgtcgt 240
atttggctga gctacagcga agttggcgat gatggtaaag caggtaccgc agtgggttat 300
ggtcgtctga gcgatgatct gagcaaagtt accgattttc gtaccgtgtt tcgccaaatg 360
ccgaaactga gcaccggcaa ccattttggc ggtcgtctgg tttttgatgg taaaggttat 420
ctgtttatcg cgctgggcga aaacaatcag cgtccgaccg cacaggatct ggataaactg 480
cagggcaaac tggttcgtct gaccgatcaa ggcgaaattc cggatgataa tccgttcatc 540
aaagaaagcg gtgcgcgtgc ggaaatttgg agctatggta ttcgcaaccc gcagggtatg 600
gcaatgaatc cgtggagtaa tgcattatgg ctgaacgaac atggtccgcg tggtggtgat 660
gaaatcaata ttccgcagaa aggcaaaaac tacggctggc cgctggcaac ctggggtatc 720
aattatagcg gctttaaaat cccggaagcg aaaggcgaaa ttgtggcagg taccgaacag 780
ccggtgttct actggaaaga ttctccggcg gtttctggta tggcgtttta taatagcgac 840
aaattcccgc agtggcagca gaaactgttt attggtgcgc tgaaagataa agacgtgatc 900
gtgatgagcg tgaacggcga caaagtgacc gaagatggcc gcattctgac cgatcgtggt 960
cagcgtattc gtgatgtgcg taccggtcca gatggttacc tgtatgtgct gaccgatgaa 1020
agtagtggtg aattactgaa agtgagcccg cgcaattaa 1059

<210> SEQ ID NO 80
<211> LENGTH: 1080
<212> TYPE: DNA
<213> ORGANISM: Pseudomonas

<400> SEQUENCE: 80
atgacccagc gttttccgag tgaagcaggt caagttaccg tgaaagaaat tgcggcaggt 60
ctggaaaatc cgtggggtct ggcattttta ccggatggcg aacacatgct ggttaccgaa 120
cgtccaggtc gtttacgttt agttggtctg gatggttctc gtagtgaacc gttagcaggt 180
gttccggatg tttttgcacg tgcacaaggt ggtttactgg atgttcgttt aagcccggcg 240
tttgaacagg atcgtctggt ttatctgagc tacgcggaag ttggcgaaga tggtaaagcg 300
ggtaccgcag ttggtcgtgg tcgtctgaat gatgatcgtt ctcgtctgga aaactttgaa 360
gtgattttcc gccagctgcc gaaactgagt agcggcattc attttggtag tcgtctggtt 420
tttgcgggta acggccatct gtttgttgca ctgggtgaaa acaatcagcg ttctaccagc 480
caggatctgg acaaacatca gggcaaagtg gtgcgcatcg gcctggatgg ttctgttccg 540
gatgataacc cgtttgttgg tcgtgatggt gttcgtccgg aaatttggag ctatggtcat 600
cgtaatcagc aaggtgctgc attaaatccg tggagtggtg tgttatggac ccatgaacat 660
ggtccgcgtg gtggtgatga aatcaatatt ccgcaagcag gcaaaaacta cggctggccg 720
ctggcaactc atggcattaa ctacagcatg ctgccgattc cagaagcgaa aggcaaaacc 780
gtgaaaggta ccgaaccgcc acatcatgtt tgggataaat ctccgggtat tagcggtatg 840
gcgttttatg atgcggaacg ctttccggca tggcaacatt ctctgtttat tggtgcgctg 900
gttgatctga gcctgattcg tctgcagctg gatggtgatc gtattgtggg cgaagaacgt 960
ctgctgaaag atctgaatgc gcgtattcgc gatgtgcgtg ttggtccaga tggtttcctg 1020
tatctgctga ctgatgcagc tgatggtaaa ctgctgcagg ttggcctgga tagcaattaa 1080

<210> SEQ ID NO 81
<211> LENGTH: 1074
<212> TYPE: DNA
<213> ORGANISM: Achromobacter

<400> SEQUENCE: 81
atggcacaag aaccaccatc tgcaccagca cgtgttactc cagttgttgg cggtctggat 60
catccatgga gtatggcatt tttaccggat ggcggtattc tgattaccga acgtccgggt 120
aatttacgtc tgctgcgtac cccaggtggt ctgagtaaac cgttaagtgg tgttccgcaa 180
gttgcagcac gtggtcaagg tggtttactg gatgttgctt taagcccgga ttttgcaacc 240
gatcgctatg tgtatctggc ctatgccgaa tctgatggcg ataaatctgg taccgcagtt 300
ggtcgtggtc gtttagctga tgatgcaagt ggtctggaag gcttcaaagt gctgtttcgt 360
caagaaccga aactgagcag cggccagcat tttggctctc gtctggtttt cgatggtaaa 420
ggctatctgt atatcgcgct gggcgaaaac aatcaacgtc cgaccgcaca ggatctggat 480
aaattacagg gcaaagtggt gcgcctgaaa accgatggtt ctgttccggc agataacccg 540
tttgtgggta aaccaggtgc acgtccggaa atttggtctt atggtcatcg taatccgcag 600
ggtatggcgt taaatccgtg gactggtgaa ttatgggaaa acgaacatgg tccgcgtggt 660
ggcgacgaaa ttaatgttgt taaaccgggc aaaaactacg gttggccgct ggcgacctat 720
ggcatcaact atagcggttt cgcaattcca gaagcgaaag gcgaaacctt accgggtatg 780
gaaccaccga ttcattggtg gccgaaatct ccggcaatta gtggtatggc gttttatgat 840
gcagatcgct ttccggcgtg gcgtaattct ctgtttattg gtgcactggg taatcaaaac 900
ctgatccgcc tgaccgtgga tggcaatcgt gtggtggaaa aagaacgttt actggtggac 960
cgcaaacgcc gtattcgtga tgttcgtcaa ggtccggatg gctatgtgta tgttctgacc 1020
gatgcaagtc cgggtgaatt actgcgtgtt gcaccggctg aaactggtgg ttaa 1074

<210> SEQ ID NO 82
<211> LENGTH: 1047
<212> TYPE: DNA
<213> ORGANISM: Pseudomonas

<400> SEQUENCE: 82
atgagcgcga aagtggaagt gctgtatgaa ggcctggaac atccgtgggc attagcattt 60
ctgccggatg cacaaggtat gctgattacc gaacgtcgtg gtagtttacg tctgctggat 120
gcacagggta aactgagtga accgttagca ggtgttccgg aagtttttgc agttggtcaa 180
ggtggtctgc tggatgttgt tttaagcccg agctttgcag aagatcgtct ggtgtatctg 240
agctttgcac aggcggaagg cgataaagcc gcaacctctg ttggtcgtgg tcgtttaagt 300
gaagatctgc gtagtctgga agatttcaaa gtgatctttc gccagatgcc ggcactgtct 360
agtggtcatc attttggcag ccgtctggtg tttgatcgtg atggctatct gttcattgcc 420
ctgggcgaac ataatcaacg tccgacctct caggacctgg ataaactgca gggcaaagtg 480
gtgcgcttat atccggatgg tcgtattccg gatgataacc cgtttgttgg tcgtgaaggt 540
gcacgtgcgg aaatttggag ttatggtcat cgtaatcagc agggtgcagc attaaatccg 600
tggaccggta aactgtggac ccatgaacat ggtccgcgtg gtggtgatga agtgaatatt 660
ccggaagcag gcaaaaacta tggttggccg attgcgaccc atggtgtgaa ttacagcttt 720
ctggcgattc cggaagcaga aggcaaagaa gttgcaggta ccgaaccgcc gcatcatgtt 780
tggaaaaaaa gtccggcgat tagtggtatg gcgttctacg atcatgcgcg ttttccggca 840
tggcagcata gtctgtttgt tggtgcatta gcaggtgcag aactgattcg tctgcagctg 900
aatggcgata aagtggtggg tgaagaacgt ttactgggtg aacgtaaagc gcgtatccgc 960
gatgtgcgtg ttggtccaga tggttatctg tatttactga ccgatagcgg caaaggtcaa 1020
ctgctgaaag tgggcctgga atgataa 1047

<210> SEQ ID NO 83
<211> LENGTH: 1080
<212> TYPE: DNA
<213> ORGANISM: Pseudomonas

<400> SEQUENCE: 83
atggcagaac agcgttttcc gagcgaagaa ggtaccctga ttgtggatac cctggcaaat 60
ggtctgcgta atccatgggc actggcattt ttaccgggtg gtaaagatat gctggtgacc 120
gaacgtgcag gtaatttacg tctggtgaat gcggaaggta aagttggtcc gagcattagc 180
ggtgttccga aagtatgggc agaaggtcaa ggtggtctgc tggatgttgc attaagcccg 240
gaattcggca aagatcgtac cgtttatctg agctacgccg aagaaggtag cgatggcaaa 300
gcaggtactg cagttggtcg tggtcagtta tctgaagatc gtgcgcgttt agaacatttt 360
accgtgattt ttcgccagct gccgaaactg tctgtgggca accattttgg cagccgtctg 420
gtgtttgatc gtaacggcta cctgtttatt gcgctgggtg aaaacaacca acgtccgacc 480
gcacaggatc tggataaact gcagggtaaa gtggtgcgca ttctgccgga tggtgaagtt 540
ccgaaagata atccgtttgt tggtaaagat aatgtgcgtc cggaaatctg gagctacggt 600
catcgcaacc agcaaggtgc ggcattaaat ccgtggaccg gtcaactgtg gacccatgaa 660
catggtccgc gtggtggtga tgaaatcaat attccgaaac cgggtaaaaa ctatggttgg 720
ccgatcgcga cccatggcat caattattct ctgctgccga ttccagaagc aaaaggtgaa 780
catgtggatg gtatggttga tccgcatcat gtgtgggaaa aaagcccggg cattagcggt 840
atggcgttct acgatagccc gaccttcaaa gcgtgggatc ataacctgtt tattggcgca 900
ctggcaaccc aagaactgat tcgcctgcag ctggaaggtg ataaagtggt gcatgaagaa 960
cgtctgttag gtgatctgaa agcccgtatt cgtgatgttc gtatgggtcc ggatggttat 1020
ctgtatgtgc tgaccgacga caaagatggt gcgctgctga aagtgggtct ggcggattaa 1080

<210> SEQ ID NO 84
<211> LENGTH: 1071
<212> TYPE: DNA
<213> ORGANISM: Citrobacter

<400> SEQUENCE: 84
atggaaactc cggcggttaa cgtggaagtt ctgcagacca aactggatca tccgtgggca 60
ctggcatttt taccgggtga taatggtatg ctgattaccc tgcgtggtgg tcaactgcgt 120
cattggcaag cagataaagg cttaagcgat ccgattccgg gtgttccgac cgtttgggca 180
agtggtcaag gtggtttatt agatgttgca ttagcgccgg attttagtca gagtcgtcgt 240
gtttggctga gctttgcaca ggcagatgca caaggtaatg caggtaccgt tgtgggttat 300
ggtcgtctga gcgatgattt aagccgtctg gaaaactttc agaccgtgtt ccgtcagatg 360

-continued

```
ccgaaactga gcaccggcaa ccactttggt ggtcgtctgg tttttgatgg caacggttat    420

ctgtttattg gtctgggcga aaacaatcag cgtccgaccg cacaggatct ggataaactg    480

cagggtaaag ttgttcgtct gaccgatcag ggcaaaattc cgccggataa tccgtttgtg    540

aatcagccgg gtgcacgtcc ggaaatttgg agctatggta ttcgtaaccc gcagggtatg    600

gcgatgaatc cgtggagtga tacattatgg ctgaatgaac atggtccgcg tggtggtgat    660

gaaatcaata ttccggaaaa aggcaaaaac tacggctggc cgctggcaac ctggggcatt    720

aactatagcg gctttaaaat cccggaagcg cagggcgaaa aagtggcagg taccgaacaa    780

ccgatctttt actggcagaa aagtccggca gttagcggta tggcgtttta tgatcatgat    840

accttcccgc agtggcgtca gaaactgttt ttaggtgcac tgaaagatca gaacgtcatc    900

gtgatgaacg tgaacggcaa caccgtgacc gaagaaggcc gcattctggg cgaacgtaaa    960

cagcgcatcc gtgatgtccg tgttggtccg gatggttatc tgtatgtgct gaccgatgaa   1020

agtgatggtg aattactgaa agtgagcccg cgttctgcag gtaatccgta a            1071
```